United States Patent
Goldenberg et al.

(10) Patent No.: US 9,492,566 B2
(45) Date of Patent: *Nov. 15, 2016

(54) ANTIBODY-DRUG CONJUGATES AND USES THEREOF

(71) Applicant: Immunomedics, Inc., Morris Plains, NJ (US)

(72) Inventors: David M. Goldenberg, Mendham, NJ (US); Serengulam V. Govindan, Summit, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,772

(22) Filed: Sep. 3, 2015

(65) Prior Publication Data

US 2015/0366988 A1    Dec. 24, 2015

Related U.S. Application Data

(60) Continuation-in-part of application No. 14/204,698, filed on Mar. 11, 2014, now Pat. No. 9,226,973, which is a division of application No. 13/948,732, filed on Jul. 23, 2013, now Pat. No. 9,028,833.

(60) Provisional application No. 61/736,684, filed on Dec. 13, 2012, provisional application No. 61/749,548, filed on Jan. 7, 2013, provisional application No. 62/049,631, filed on Sep. 12, 2014.

(51) Int. Cl.

| | |
|---|---|
| *A61K 47/48* | (2006.01) |
| *A61K 31/4745* | (2006.01) |
| *A61K 39/395* | (2006.01) |
| *A61K 31/7068* | (2006.01) |
| *A61K 45/06* | (2006.01) |
| *A61K 31/337* | (2006.01) |
| *A61K 31/4184* | (2006.01) |
| *A61K 31/4375* | (2006.01) |
| *A61K 31/454* | (2006.01) |
| *A61K 31/513* | (2006.01) |
| *A61K 31/675* | (2006.01) |
| *A61K 31/7088* | (2006.01) |
| *A61K 31/713* | (2006.01) |
| *C07K 16/28* | (2006.01) |
| *C07K 16/30* | (2006.01) |
| *A61N 5/10* | (2006.01) |
| *A61K 39/00* | (2006.01) |

(52) U.S. Cl.
CPC ....... *A61K 47/48569* (2013.01); *A61K 31/337* (2013.01); *A61K 31/4184* (2013.01); *A61K 31/4375* (2013.01); *A61K 31/454* (2013.01); *A61K 31/4745* (2013.01); *A61K 31/513* (2013.01); *A61K 31/675* (2013.01); *A61K 31/7068* (2013.01); *A61K 31/7088* (2013.01); *A61K 31/713* (2013.01); *A61K 39/39558* (2013.01); *A61K 45/06* (2013.01); *A61K 47/48384* (2013.01); *C07K 16/2803* (2013.01); *C07K 16/2833* (2013.01); *C07K 16/2887* (2013.01); *C07K 16/30* (2013.01); *C07K 16/3007* (2013.01); *A61K 2039/505* (2013.01); *A61N 5/1001* (2013.01); *A61N 2005/1021* (2013.01); *C07K 2317/92* (2013.01); *C07K 2317/94* (2013.01)

(58) Field of Classification Search
CPC ...................................................... A61K 47/48
USPC .............. 424/181.1, 178.1; 530/391.1, 391.7
See application file for complete search history.

(56) References Cited

U.S. PATENT DOCUMENTS

| | | | |
|---|---|---|---|
| 4,036,945 | A | 7/1977 | Haber |
| 4,046,722 | A | 9/1977 | Rowland |
| 4,200,690 | A | 4/1980 | Root et al. |
| 4,331,647 | A | 5/1982 | Goldenberg |
| 4,359,457 | A | 11/1982 | Neville et al. |
| 4,699,784 | A | 10/1987 | Shih et al. |
| 4,704,692 | A | 11/1987 | Ladner |
| 4,816,567 | A | 3/1989 | Cabilly et al. |
| 4,824,659 | A | 4/1989 | Hawthorne |
| 4,916,213 | A | 4/1990 | Scannon et al. |

(Continued)

FOREIGN PATENT DOCUMENTS

| | | |
|---|---|---|
| EP | 0253202 | 1/1988 |
| EP | 0306943 | 3/1989 |

(Continued)

OTHER PUBLICATIONS

US 6,558,648, 05/2003, Griffiths et al. (withdrawn).
Clinical Trial NCT01631552 (version of Jun. 28, 2012).*

(Continued)

*Primary Examiner* — Yan Xiao
(74) *Attorney, Agent, or Firm* — Richard A. Nakashima

(57) ABSTRACT

The present invention relates to therapeutic immunoconjugates comprising SN-38 attached to an antibody or antigen-binding antibody fragment. The antibody may bind to Trop-2 or CEACAM5 and the immunoconjugate may be administered at a dosage of between 4 mg/kg and 16 mg/kg, preferably 4, 6, 8, 9, 10, 12, or 16 mg/kg. When administered at specified dosages and schedules, the immunoconjugate can reduce solid tumors in size, reduce or eliminate metastases and is effective to treat cancers resistant to standard therapies, such as radiation therapy, chemotherapy or immunotherapy. Surprisingly, the immunoconjugate is effective to treat cancers that are refractory to or relapsed from irinotecan.

22 Claims, 27 Drawing Sheets

(56) References Cited

U.S. PATENT DOCUMENTS

| | | |
|---|---|---|
| 4,918,163 A | 4/1990 | Young |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,112,954 A | 5/1992 | Abrams et al. |
| 5,122,368 A | 6/1992 | Greenfield et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,679,640 A | 10/1997 | Gaeta et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,708,146 A | 1/1998 | Willner et al. |
| 5,716,595 A | 2/1998 | Goldenberg |
| 5,736,119 A | 4/1998 | Goldenberg et al. |
| 5,750,105 A | 5/1998 | Newman et al. |
| 5,776,456 A | 7/1998 | Anderson et al. |
| 5,789,554 A | 8/1998 | Leung et al. |
| 5,792,845 A | 8/1998 | O'Reilly et al. |
| 5,795,967 A | 8/1998 | Aggarwal et al. |
| 5,798,554 A | 8/1998 | Grimaldi et al. |
| 5,817,307 A | 10/1998 | Cummins |
| 5,824,701 A | 10/1998 | Greenwald et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,056,973 A | 5/2000 | Allen et al. |
| 6,077,499 A | 6/2000 | Griffiths et al. |
| 6,096,289 A | 8/2000 | Goldenberg |
| 6,156,754 A | 12/2000 | Lerchen et al. |
| 6,165,440 A | 12/2000 | Esenaliev |
| 6,183,744 B1 | 2/2001 | Goldenberg |
| 6,187,287 B1 | 2/2001 | Leung et al. |
| 6,201,104 B1 | 3/2001 | MacDonald et al. |
| 6,214,345 B1 | 4/2001 | Firestone et al. |
| 6,254,868 B1 | 7/2001 | Leung et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |
| 6,530,944 B2 | 3/2003 | West et al. |
| 6,562,318 B1 | 5/2003 | Filler |
| 6,653,104 B2 | 11/2003 | Goldenberg |
| 6,716,821 B2 | 4/2004 | Zhao et al. |
| 7,018,809 B1 | 3/2006 | Carter |
| 7,074,403 B1 | 7/2006 | Goldenberg et al. |
| 7,122,636 B1 | 10/2006 | Hsei et al. |
| 7,151,164 B2 | 12/2006 | Hansen et al. |
| 7,238,785 B2 | 7/2007 | Govindan et al. |
| 7,312,318 B2 | 12/2007 | Hansen et al. |
| 7,387,779 B2 | 6/2008 | Kalluri |
| 7,585,491 B2 | 9/2009 | Govindan et al. |
| 7,591,994 B2 | 9/2009 | Govindan et al. |
| 7,772,373 B2 | 8/2010 | Hansen et al. |
| 7,820,161 B1 | 10/2010 | Curd et al. |
| 7,910,103 B2 | 3/2011 | Goldenberg |
| 7,931,903 B2 | 4/2011 | Hansen et al. |
| 7,999,083 B2 | 8/2011 | Govindan et al. |
| 8,080,250 B1 | 12/2011 | Govindan et al. |
| 8,119,101 B2 | 2/2012 | Byrd et al. |
| 8,268,317 B2 | 9/2012 | Govindan et al. |
| 8,268,319 B2 | 9/2012 | Govindan et al. |
| 8,309,094 B2 | 11/2012 | Gerber et al. |
| 8,420,086 B2 | 4/2013 | Govindan et al. |
| 8,425,912 B2 | 4/2013 | Govindan et al. |
| 8,586,049 B2 | 11/2013 | Gerber et al. |
| 8,871,908 B2 | 10/2014 | Liu et al. |
| 9,028,833 B2 * | 5/2015 | Govindan ............ A61K 31/454 424/178.1 |
| 2001/0034363 A1 | 10/2001 | Li et al. |
| 2002/0018749 A1 | 2/2002 | Hudson et al. |
| 2003/0103979 A1 | 6/2003 | Leung et al. |
| 2003/0133972 A1 | 7/2003 | Danthi et al. |
| 2004/0001838 A1 | 1/2004 | Zhao et al. |
| 2004/0076683 A1 | 4/2004 | Hoarau et al. |
| 2006/0142506 A1 | 6/2006 | Breitenkamp et al. |
| 2006/0193865 A1 | 8/2006 | Govindan et al. |
| 2007/0212350 A1 | 9/2007 | Govindan et al. |
| 2008/0166363 A1 | 7/2008 | Govindan et al. |
| 2011/0070156 A1 * | 3/2011 | Govindan ........ A61K 47/48384 424/1.49 |
| 2011/0160159 A1 | 6/2011 | Ryan |
| 2011/0256053 A1 | 10/2011 | Chang et al. |
| 2011/0274704 A1 | 11/2011 | Chang et al. |
| 2011/0305631 A1 | 12/2011 | Govindan et al. |
| 2012/0052076 A1 | 3/2012 | Alberti |
| 2012/0082617 A1 | 4/2012 | Govindan et al. |
| 2012/0328564 A1 | 12/2012 | Govindan et al. |
| 2013/0089872 A1 | 4/2013 | Nakamura et al. |
| 2013/0090458 A1 | 4/2013 | Govindan et al. |
| 2013/0122020 A1 | 5/2013 | Liu et al. |
| 2013/0177526 A1 | 7/2013 | Govindan et al. |
| 2013/0216561 A1 | 8/2013 | Govindan et al. |
| 2014/0004078 A1 | 1/2014 | Govindan et al. |

FOREIGN PATENT DOCUMENTS

| | | |
|---|---|---|
| EP | 0332865 | 9/1989 |
| EP | 0510949 | 10/1992 |
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 0074718 | 12/2000 |
| WO | 0076551 | 12/2000 |
| WO | 0124763 | 4/2001 |
| WO | 2004054622 | 7/2004 |
| WO | 2007123995 | 11/2007 |
| WO | 2010089782 | 8/2010 |

OTHER PUBLICATIONS

Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11(9):1936-47.

Bennouna et al., "Therapeutic strategies for colorectal cancer in Europe and the United States: focus on chemotherapy for advanced colorectal cancer" Int. J. Clin. Oncol. (2002) 7:236-244.

Burkard et al., "Validating cancer drug targets through chemical genetics", Biochim Biophys Acta. Dec. 2010;1806(2):251-7.

Burke et al., "Design, synthesis, and biological evaluation of antibody-drug conjugates comprised of potent camptothecin analogues", Bioconjug Chem. Jun. 2009;20(6):1242-50.

(56) References Cited

OTHER PUBLICATIONS

Burnham et al., "Invasion of HeLa cells by group B streptococcus requires the phosphoinositide-3-kinase signalling pathway and modulates phosphorylation of host-cell Akt and glycogen synthase kinase-3", Microbiology. Dec. 2007:153(Pt 12):4240-52.

Cao et al., "Bispecific Antibodies as Novel Bioconjugates" Bioconj. Chem. Nov.-Dec. 1998;9(6):635-44.

Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.

Carter et al., Chemotherapy of Cancer; 2nd Edition; John Wiley & Sons, New York, 1981; Appendix C.

Chari et al., "Immunoconjugates Containing Novel Maytansinoids: Promising Anticancer Drugs" Cancer Res. Jan. 1, 1992;52(1):127-31.

Feldmann et al., "Design of effective immunotherapy for human autoimmunity", Nature. Jun. 2, 2005;435(7042):612-9.

Fukuda et al., "Evaluation of novel platinum complexes, inhibitors of topoisomerase I and II in non-small cell lung aancer (NSCLC) sublines resistant to cisplatin", Anticancer Res. Mar.-Apr. 1995;15(2):393-8.

Garcia-Giron et al., "Phase II trial of fortnightly irinotecan (CPT-11) in the treatment of colorectal cancer patients resistant to previous fluoropyrimidine-based chemotherapy", Clin Transl Oncol. Jul. 2005;7(6):244-9.

Gomez-Manzano et al., "Delta-24 increases the expression and activity of topoisomerase I and enhances the antiglioma effect of irinotecan", Clin Cancer Res. Jan. 15, 2006;12(2):556-62.

Govindan et al., "Milatuzumab-SN-38 conjugates for the treatment of CD74+ cancers", Mol Cancer Ther. Jun. 2013;12(6):968-78.

Gueritte-Voegelein et al., "Relationships between the Structure of Taxol Analogues and Their Antimitotic Activity" J. Med. Chem. 1991, 34, 992-998.

Guillemard et al., "Taxane-Antibody Conjugates Afford Potent Cytotoxicity, Enhanced Solubility, and Tumor Target Selectivity" Cancer Res. 61, 694-699, Jan. 15, 2001.

Gura, T., "Systems for identifying new drugs are often faulty", Science. Nov. 7, 1997;278(5340):1041-2.

Hatzakis et al., "Synthesis and single enzyme activity of a clicked lipase-BSA hetero-dimer" Chem. Commun., 2006, 2012-2014.

He et al., "Synthesis and biological evaluation of bis and monocarbonate prodrugs of 10-hydroxycamptothecins", Bioorg Med Chem. Aug. 1, 2004;12(15):4003-8.

Heindel et al., "A Novel Heterobifunctional Linker for Formyl to Thiol Coupling" Bioconjugate Chem. 1991, 2, 427-430.

Horwitz et al., "Antiviral action of camptothecin", Antimicrob Agents Chemother. Nov. 1972;2(5):395-401.

Huang et al., "The Rana catesbeiana rcr Gene Encoding a Cytotoxic Ribonuclease" J. Biol. Chem. 273(11):6395-6401 (1998).

Kaiser, J., "Cancer. First pass at cancer genome reveals complex landscape", Science. Sep. 8, 2006;313(5792):1370.

King et al., "Monoclonal Antibody Conjugates of Doxorubicin Prepared with Branched Linkers: A Novel Method for ncreasing the Potency of Doxorubicin Immunoconjugates" Bioconjugate Chem. 1999, 10, 279-288.

Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.

Krontiris and Capizzi, Internal Medicine, Chapters 71-72, pp. 699-729; 4th Edition, Jay Stein (Ed.), Elsevier Science, 1994.

Kufe et al., Non-Intercalating Topoisomerase-Targeting Drugs, Holland-Frei Cancer Medicine, Hamilton (ON), BC Decker (2003).

Kufe et al., Topoisomerase Biology, 6th Ed., Holland-Frei Cancer Medicine, Hamilton (ON), BC Decker (2003).

Mahato et al., "Prodrugs for improving tumor targetability and efficiency", Adv Drug Deliv Rev. Jul. 18, 2011;63(8):659-70.

Matasumura et al., "Preclinical and clinical studies of NK012, an SN-38-incorporating polymeric micelles, which is designed based on EPR effect", Adv Drug Deliv Rev. Mar. 18, 2011;63(3):184-92.

Miller et al., "Development of Taxoids with Enhanced Toxicity and Solubility" Poster Presentation, 224th ACS Nat. Meeting, Aug. 18-22, 2002, Boston, MA.

Mine Safety and Health Administration (Special Hazards of Acetylene, Sep. 16, 2011).

Moon et al., "Antibody Conjugates of 7-Ethyl-10-hydroxycamptothecin (SN-38) for Targeted Cancer Chemotherapy" J. Med. Chem. 2008, 51, 6916-6926.

Newton et al., "Potent and specific antitumor effects of an anti-CD22-targeted cytotoxic ribonuclease: potential for the treatment of non-Hodgkin lymphoma" Blood, 97(2):528-35 (2001).

Paul, W., ed., Fundamental Immunology, 3rd Ed., Raven Press, New York, 1993, p. 292-295.

Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.

Reddy et al., "Elimination of Fc Receptor-Dependent Effector Functions of a Modified IgG4 Monoclonal Antibody to Human CD4", J. Immunol. 164:1925-1933 (2000).

Rowlinson-Busza et al., "Targeted delivery of biologic and other antineoplastic agents" Curr. Opin. Oncol. Dec. 1992;4(6):1142-1148.

Sharkey et al., "Epratuzumab-SN-38: a new antibody-drug conjugate for the therapy of hematologic malignancies", Mol Cancer Ther. Jan. 2012;11(1):224-34.

Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.

Shin et al., "The Processing and Fate of Antibodies and Their Radiolabels Bound to the Surface of Tumor Cells In Vitro: A Comparison of Nine Radiolabels" J. Nucl. Med. 1994; 35:899-908.

Shin et al., "In vitro and in vivo reactivity of an internalizing antibody, RS7, with human breast cancer", Cancer Res. Dec. 1, 1995;55(23 Suppl):5857s-5863s.

Stanford University Environmental Health and Safety (Information on Azide Compounds, Dec. 2, 2008).

Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).

Suzawa et al., "Enhanced tumor cell selectivity of adriamycin-monoclonal antibody conjugate via a poly(ethylene glycol)-based cleavable linker" J. Control. Release 79:229-242 (2002).

Talmadge et al., "Murine models to evaluate novel and conventional therapeutic strategies for cancer", Am J Pathol. Mar. 2007;170(3):793-804.

Thurber et al., "Antibody tumor penetration: transport opposed by systemic and antigen-mediated clearance", Adv Drug Deliv Rev. Sep. 2008;60(12):1421-34.

Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.

Van Noort and Amor, "Cell Biology of Autoimmune Disease", vol. 178, pp. 127-206; International Rev. of cytology, 1998.

Walker et al., "Synthesis of an Immunoconjugate of Camptothecin" Bioorg. Med. Chem. Lett. 12(2):217-219 (2002).

Beckman et al., "Antibody constructs in cancer therapy: protein engineering strategies to improve exposure in solid tumors", Cancer. Jan. 15, 2007;109(2)170-9.

Berenbaum, MC., "Synergy, additivism and antagonism in immunosuppression. A critical review", Clin Exp Immunol. Apr. 1977;28(1):1-18.

Berenbaum, MC., "What is synergy?", Pharmacol Rev. Jun. 1989;41(2):93-141.

Cespedes et al, "Mouse models in oncogenesis and cancer therapy", Clin Transl Oncol. May 2006;8(5):318-29.

Dennis, C., "Cancer: off by a whisker", Nature. Aug. 17, 2006;442(7104):739-41.

(56) References Cited

OTHER PUBLICATIONS

Foran, JM., "Antibody-based therapy of non-Hodgkin's lymphoma", Best Pract Res Clin Haematol. Sep. 2002;15(3):449-65.
Fujimori et al., "A modeling analysis of monoclonal antibody percolation through tumors: a binding-site barrier", J Nucl Med. Jul. 1990;31(7):1191-8.
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.
Mason et al., "Value of monoclonal anti-CD22 (p135) antibodies for the detection of normal and neoplastic B lymphoid cells", Blood. Mar. 1987;69(3):836-40.
Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).
Morrison et al., "Chimeric human antibody molecules: mouse antigen-binding domains with human constant region lomains", Proc Natl Acad Sci USA Nov. 1984;81(21):6851-5.
Murthy et al., "Lymphoma imaging with a new technetium-99m labelled antibody, LL2", Eur J Nucl Med. 1992;19(6):394-401.
ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human ymphoma", Cancer Res. 49(16):4568-77 (1989).
Perrota et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates", Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).
Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86(24):10029-33.
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79(6):1979-83 (1982).
Rudnick et al., "Affinity and avidity in antibody-based tumor targeting", Cancer Biother Radiopharm. Apr. 2009;24(2):155-61.
Saltzman et al., "Transport rates of proteins in porous materials with known microgeometry", Biophys. J. 55(1):163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sherwood et al., "Controlled antibody delivery systems", Biotechnology 10(11):1446-9 (1992).
Shih et al., "Internalization and intracellular processing of an anti-B-cell lymphoma monoclonal antibody, LL2", Int J cancer 56(4):538-45 (1994).
Singer et al., "Optimal humanization of 1B4, an anti-CD18 murine monoclonal antibody, is achieved by correct choice of human V-region framework sequences", J. lmmunol. 150(7):2844-57 (1993).
Stein et al., "Epitope specificity of the anti-(B cell lymphoma) monoclonal antibody, LL2", Cancer Immunol. Immunother. 37(5):293-8 (1993).
Tallarida, RJ., Drug Synergism and Dose Effect Analysis, Ed. Chapman & Hall, 2000, pp. 1-8; 10-13; 57-71.
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Tsang et al.,"Reactive oxygen species mediate doxorubicin induced p53-independent apoptosis", Life Sci. Sep. 5, 2003;73(16):2047-58.
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Wilson et al., "cDNA cloning of the B cell membrane protein CD22: a mediator of B-B cell interactions", J Exp Med. Jan. 1, 1991;173(1):137-46.
Wilson et al., "Genomic structure and chromosomal mapping of the human CD22 gene", J Immunol. Jun. 1, 1993;150(11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies for their capacity to induce cell-mediated lysis of malignant B cells", Cancer Res. Jul. 15, 1998;58(14):3051-8.
Bardia et al., "Therapy of refractory/relapsed metastatic triple-negative breast cancer (TNBC) with an anti-Trop-2-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31, Epub May 8, 2015.
Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II

(56) References Cited

OTHER PUBLICATIONS study", J Clin Oncol 33, 2015 (suppl; abstr 2505), Retrieved from http://meetinglibrary.asco.org/content/148390-156.
Goldenberg et al., "Trop-2 is a novel target for solid cancer therapy with sacituzumab govitecan (IMMU-132), an antibody-drug conjugate (ADC)", Oncotarget. Jun. 18, 2015. [Epub ahead of print].
Goldenberg et al., "Selective in vivo therapeutic efficacies of SN-38 conjugates of an anti-CEACAM5 antibody in preclinical models of human colon carcinoma", Presentation, ASCO 2009 Gastrointestinal Cancers Symposium, San Francisco, CA, Jan. 15-17, 2009.
Goldenberg, D.M., "Challenging the Dogmas: Clinical Efficacy of SN-38-Conjugated Antibodies in Solid Tumors", 26th EORTC-NCI-AACR Symposium on Molecular Targets and Cancer Therapeutics, Barcelona, Spain, Nov. 18-21, 2014.
Goldenberg, D.M., "SN-38 Conjugates for Therapy of Advanced Solid Cancers", 5th Annual World ADC Summit in San Diego, CA, Oct. 26-29, 2014.
Gorman, G. "Focused on Therapy: Cancer, Autoimmune & Other Serious Diseases", Presentation, Oppenheimer 23rd Annual Healthcare Conference, NYC, Dec. 12, 2012.
Govindan et al., "Optimal cleavable linker for antibody-SN-38 conjugates for cancer therapy: Impact of linker's stability on efficacy", Poster, AACR 103rd Annual Meeting, Chicago, IL, Mar. 31-Apr. 4, 2012.
Govindan et al., "Improving the Therapeutic Index in Cancer Therapy by Using Antibody-Drug Conjugates Designed with a Moderately Cytotoxic Drug", Mol Pharm. Nov. 25, 2014. [Epub ahead of print].
Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.
Govindan et al., "CEACAM5-targeted therapy of human colonic and pancreatic cancer xenografts with potent abetuzumab-SN-38 immunoconjugates", Clin Cancer Res. Oct. 1, 2009;15(19):6052-61.
Govindan et al., "Targeted therapy of human colonic, lung, and pancreatic cancer xenografts, growing in nude mice, with potent antibody conjugates of SN-38", Poster, AACR 100th Annual Meeting, Denver, CO, Apr. 18-22, 2009.
Govindan et al., "Efficacious therapies of two human pancreatic cancer xenografts and an aggressive human lymphoma xenograft with redesigned antibody-SN-38 conjugates", Poster, AACR 101st Annual Meeting, Washington, JC, Apr. 17-21, 2010.
Guarino et al., "Therapy of advanced metastatic lung cancer with an anti-Trop-2-SN-38 antibody-drug conjugate (ADC), sacituzumab govitecan (IMMU-132): Phase I/II clinical experience", J Clin Oncol 33, 2015 (suppl; abstr 2504), Retrieved from http://meetinglibrary.asco.org/content/148373-156.
Moon et al., "Cross-linker evaluation in the design of antibody-SN-38 conjugates for cancer therapy", Poster, AACR 101st Annual Meeting, Washington, DC, Apr. 17-21, 2010.
Karacay et al., "Combining antibody-targeted radiation (radioimmunotherapy) and antibody-SN-38 conjugates (ADC) mproves pancreatic cancer therapy", Poster, AACR 101st Annual Meeting, Washington, DC, Apr. 17-21, 2010.
Segal et al., "IMMU-130, an SN-38 antibody-drug conjugate (ADC) targeting CEACAM5, is therapeutically active in.metastatic colorectal cancer (mCRC): Initial clinical results of two Phase I studies", Presentation, AACR Annual Vleeting, San Diego, CA, Apr. 5-9, 2014.
Sharkey et al., "Enhanced Delivery of SN-38 to Human Tumor Xenografts with an Anti-Trop-2-SN-38 Antibody Conjugate (Sacituzumab Govitecan)", Clin Cancer Res. Jun. 23, 2015 pii: clincanres.0670.2015. [Epub ahead of print].
Starodub et al., "Phase I/II trial of IMMU-132 (isactuzumab govitecan), an anti-Trop-2-SN-38 antibody drug conjugate (ADC): Results in patients with metastatic gastrointestinal (GI) cancers", J Clin Oncol 33, 2015 (suppl 3; abstr 703), Retrieved from http://meetinglibrary.asco.org/content/140198-158.
Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.
Baum et al., "Initial clinical results with technetium-99m-labeled LL2 monoclonal antibody fragment in the radioimmunodetection of B-cell lymphomas", Cancer Feb. 1, 1994;73(3 Suppl):896-9.
Beers et al., The Merck Manual of Diagnosis and Therapy, Ch. 180, p. 1474-1476; 17th Ed., Whitehouse Station, NJ, Merck Research Labs (1999).
Belisle et al., "Epitope specificity of the anti-B-cell lymphoma monoclonal antibody, LL2", Proc Am Assoc Cancer Res 1993; 34:481, Abstr #2873.
Bendig, M., "Humanization of Rodent Monoclonal Antibodies by CDR Grafting", Academic Press Inc., New York, NY, vol. 8, (1995), pp. 83-93.
Bhat et al., "Human antilipid a monoclonal antibodies bind to human B cells and the i antigen on cord red blood cells", J Immunol. Nov. 1, 1993;151(9):5011-21.
Carter et al., "Humanization of an anti-p185HER2 antibody for human cancer therapy", Proc. Natl. Acad. Sci. USA 89(10):4285-9 (1992).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Coloma et al., "Design and production of novel tetravalent bispecific antibodies", Nat. Biotechnol. 15(2):159-63 (1997).
Dillon et al., "Use of Polymerase Chain Reaction for the Rapid Construction of Synthetic Genes", Methods in Mololecular Biology, vol. 15: PCR Protocols: Current Methods and Applications, White (Ed.), pp. 263-268, Humana 'ress, Inc. (1993).
Ellis et al., "Engineered anti-CD38 monoclonal antibodies for immunotherapy of multiple myeloma", J Immunol. Jul. 15, 1995;155(2):925-37.
Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).
Foy et al., "In vivo CD40-gp39 interactions are essential for thymus-dependent humoral immunity. II Prolonged suppression of the humoral immune response by an antibody to the ligand for CD40, gp39", J Exp Med. Nov. 1, 1993;178(5):1567-75.
French et al., "Response of B-cell lymphoma to a combination of bispecific antibodies and saporin", Leuk. Res. 20(7):607-17 (1996).
Ghetie et al., "Evaluation of ricin A chain-containing immunotoxins directed against CD19 and CD22 antigens on -iormal and malignant human B-cells as potential reagents for in vivo therapy", Cancer Res. 48(9):2610-7 (1988).
Goldenberg et al., "Targeting, dosimetry, and radioimmunotherapy of B-cell lymphomas with iodine-131-labeled LL2 monoclonal antibody", J Clin Oncol. Apr. 1992;9(4):548-64.
Goldenberg, D. M. "New Developments in Monoclonal Antibodies for Cancer Detection and Therapy", CA Cancer J. Clin. 44(1):43-64 (1994).
Goldenberg et al., "Epratuzumab (Humanized Anti-CD22 MAb) Conjugated with SN-38, a New Antibody-Drug.conjugate (ADC) for the Treatment of Hematologic Tumors: Preclinical Studies Alone and in Combination with Veltuzumab, a Humanized Anti-CD20 MAb", Blood (ASH Annual Meeting Abstracts) 2010 116: Abstract 3941.

(56) References Cited

OTHER PUBLICATIONS

Gondo et al., "HLA class II antigen associated invariant chain gene expression in malignant lymphoma", Br. J. Haematol. 67(4):413-7 (1987).
Green et al., "Antigen-specific human monoclonal antibodies from mice engineered with human Ig heavy and light chain YACs", Nature Genetics 7:13-21 (1994).
Gussow et al., "Humanization of monoclonal antibodies", Methods Enzymol. 1991;203:99-121.
Hansen et al., "Internalization and catabolism of radiolabelled antibodies to the MHC class-II invariant chain by B-cell lymphomas", Biochem. J. 1996, 320:293-300.
Hashida et al., "More useful maleimide compounds for the conjugation of Fab' to horseradish peroxidase through hiol groups in the hinge", J Appl Biochem. Feb.-Apr. 1984;6(1-2):56-63.
Hekman et al. "Initial experience with treatment of human B cell lymphoma with anti-CD19 monoclonal antibody", Cancer Immunol. Immunother. 1991;32(6):364-72.
Hess et al., "Specificity of effector T lymphocytes in autologous graft-versus-host disease: role of the major iistocompatibility complex class II invariant chain peptide", Blood 89(6):2203-9 (1997).
Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.
Imuran patient information leaflet, GlaxoSmithKline 7076598/5093, Oct. 2004.
Inaoki et al., "CD19-regulated signaling thresholds control peripheral tolerance and autoantibody production in B lymphocytes", J Exp Med. Dec. 1, 1997;186(11):1923-31.
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiener et al., "Stimulation of CD40 with purified soluble gp39 induces proinflammatory responses in human monocytes", J Immunol. Nov. 15, 1995;155(10):4917-25.
Kiesel et al., "Removal of cells from a malignant B-cell line from bone marrow with immunomagnetic beads and with complement and immunoglobulin switch variant mediated cytolysis", Leuk. Res. 11(12):1119-25 (1987).
Kohler et al., "Continuous cultures of fused cells secreting antibody of predefined specificity", Nature 256:495-7 (1975).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).
Leung et al., "Chimerization and humanization of a B-cell Lymphoma specific antibody, LL2", Proc Am Assoc Cancer Res 1993; 34:481, Abstr #2872.
Leung et al., "Chimerization of LL2, a Rapidly Internalizing Antibody Specific for B Cell Lymphoma", Hybridoma 13(6):469-476 (1994).
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52(8):1701-4 (1999).

Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L. "Immunotherapy for non-Hodgkin's lymphoma", Curr. Opin. Oncol. 8(5):353-9 (1996).
Losman et al., "Baboon anti-idiotype antibodies mimic a carcinoembryonic antigen epitope", Int J Cancer. Aug. 15, 1990;46(2):310-4.
Lundberg, B. "Preparation of drug-carrier emulsions stabilized with phosphatidylcholine-surfactant mixtures", J. Pharm. Sci. 83(1):72-5 (1994).
Lundberg et al., "Submicron lipid emulsions containing amphipathic polyethylene glycol for use as drug-carvers with prolonged circulation time", Int. J. Pharm. 134:119-127 (1996).
Alberti et al., "Biochemical characterization of Trop-2, a cell surface molecule expressed by human carcinomas: formal proof that the monoclonal antibodies T16 and MOv-16 recognize Trop-2", Hybridoma. Oct. 1992;11(5):539-45.
Basu et al., "The epithelial/carcinoma antigen EGP-1, recognized by monoclonal antibody RS7-3G11, is phosphorylated on serine 303", Int J Cancer. Aug. 9, 1995;62(4):472-9.
Bignotti et al., "Trop-2 protein overexpression is an independent marker for predicting disease recurrence in endometrioid endometrial carcinoma", BMC Clin Pathol. Nov. 14, 2012;12:22.
Chang et al., "Ranpimase (frog RNase) targeted with a humanized, internalizing, anti-Trop-2 antibody has potent cytotoxicity against diverse epithelial cancer cells", Mol Cancer Ther. Aug. 2010;9(8):2276-86.
Chen et al., "Increased expression of Trop2 correlates with poor survival in extranodal NK/T cell lymphoma, nasal type", Virchows Arch. Nov. 2013;463(5):713-9.
Cubas et al., "Trop2: a possible therapeutic target for late stage epithelial carcinomas", Biochim Biophys Acta. Dec. 2009;1796(2):309-14.
Fang et al., "Different effects of ERβ and TROP2 expression in Chinese patients with early-stage colon cancer", Tumour Biol. Dec. 2012;33(6):2227-35.
Farivar et al., "Nano—drug Delivery of Apoptosis Activator 2 to AGS Cells by Liposomes Conjugated with Anti-TROP2 Antibody", N Am J Med Sci. Nov. 2012;4(11):582-5.
Friedman et al., "BR96 sFv-PE40, a potent single-chain immunotoxin that selectively kills carcinoma cells", Cancer Res. Jan. 15, 1993;53(2):334-9.
Kapoor, S., "TROP2 expression and its evolving role in tumor pathogenesis in systemic tumors", Tumour Biol. Jun. 2013;34(3):1967-8.
Lin et al., "Significantly upregulated TACSTD2 and Cyclin D1 correlate with poor prognosis of invasive ductal breast cancer", Exp Mol Pathol. Feb. 2013;94(1):73-8.
Lin et al., "A novel human Fab antibody for Trop2 inhibits breast cancer growth in vitro and in vivo", Int J Cancer. Mar. 1, 2014;134(5):1239-49.
Lipinski et al., "Human trophoblast cell-surface antigens defined by monoclonal antibodies", Proc Natl Acad Sci U S A. Aug. 1981;78(8):5147-50.
Liu et al., "Overexpression of TROP2 predicts poor prognosis of patients with cervical cancer and promotes the Droliferation and invasion of cervical cancer cells by regulating ERK signaling pathway", PLoS One Sep. 27, 2013;8(9): g5864.
Liu et al., "Trop-2-targeting tetrakis-ranpimase has potent antitumor activity against triple-negative breast cancer", Mol Cancer. Mar. 10, 2014;13:53.
Ning et al., "TROP2 correlates with microvessel density and poor prognosis in hilar cholangiocarcinoma", J Gastrointest Surg. Feb. 2013;17(2):360-8.
Ning et al., "TROP2 expression and its correlation with tumor proliferation and angiogenesis in human gliomas", Neurol Sci. Oct. 2013;34(10):1745-50.

(56) References Cited

OTHER PUBLICATIONS

Pak et al., "Significance of EpCAM and TROP2 expression in non-small cell lung cancer", World J Surg Oncol. Apr. 6, 2012;10:53.

Ripani et al., "Human Trop-2 is a tumor-associated calcium signal transducer", Int J Cancer. May 29, 1998;76(5):671-6.

Sapra et al., "Long-term tumor regression induced by an antibody-drug conjugate that targets 5T4, an oncofetal antigen expressed on tumor-initiating cells", Mol Cancer Ther. Jan. 2013;12(1):38-47.

Shor et al., "Enhanced Antitumor Activity of an Anti-5T4 Antibody-Drug Conjugate in Combination with PI3K/mTOR Inhibitors or Taxanes", Clin Cancer Res. Jan. 15, 2016;22(2):383-94.

Shvartsur et al., "Trop2 and its overexpression in cancers: regulation and clinical/therapeutic implications", Genes Cancer. Mar. 2015;6(3-4):84-105.

Stein et al., "Murine monoclonal antibodies raised against human non-small cell carcinoma of the lung: specificity and tumor targeting", Cancer Res. Feb. 15, 1990;50(4):1330-6.

Stein et al., "Specificity and properties of MAb RS7-3G11 and the antigen defined by this pancarcinoma monoclonal antibody", Int J Cancer Dec. 2, 1993;55(6):938-46.

Stein et al., "Characterization of cluster 13: the epithelial/carcinoma antigen recognized by MAb RS7", Int J Cancer Suppl. 1994;8:98-102.

Stein et al., "Radioimmunotherapy of a human lung cancer xenograft with monoclonal antibody RS7: evaluation of (177)Lu and comparison of its efficacy with that of (90)Y and residualizing (131)I", J Nucl Med. Jun. 2001;42(6):967-74.

Stepan et al., "Expression of Trop2 cell surface glycoprotein in normal and tumor tissues: potential implications as a aancer therapeutic target", J Histochem Cytochem. Jul. 2011;59(7):701-10.

Stoyanova et al., "Regulated proteolysis of Trop2 drives epithelial hyperplasia and stem cell self-renewal via β-catenin signaling", Genes Dev. Oct. 15, 2012;26(20):2271-85.

Trerotola et al., "Letter to the editor: efficacy and safety of anti-Trop antibodies, R. Cubas, M. Li, C. Chen and Q. Yao, Biochim Biophys Acta 1796 (2009) 309-1", Biochim Biophys Acta. Apr. 2010;1805(2):119-20.

Tsukahara et al., "TROP2 expressed in the trunk of the ureteric duct regulates branching morphogenesis during kidney development", PLoS One. 2011;6(12):e28607.

Varughese et al., "Cervical carcinomas overexpress human trophoblast cell-surface marker (Trop-2) and are highly sensitive to immunotherapy with hRS7, a humanized monoclonal anti-Trop-2 antibody", Am J Obstet Gynecol. Dec. 2011;205(6):567.e1-7.

Vidmar et al., "Biochemical and preliminary X-ray characterization of the tumor-associated calcium signal transducer 2 (Trop2) ectodomain", Protein Expr Purif. Sep. 2013;91(1):69-76.

Wang et al., "Identification of Trop-2 as an oncogene and an attractive therapeutic target in colon cancers", Mol cancer Ther. Feb. 2008;7(2):280-5.

Wang et al., "Loss of Trop2 promotes carcinogenesis and features of epithelial to mesenchymal transition in squamous cell carcinoma", Mol Cancer Res. Dec. 2011;9(12):1686-95.

Wu et al., "Potential therapeutic target and independent prognostic marker of TROP2 in laryngeal squamous cell aarcinoma", Head Neck. Oct. 2013;35(10):1373-8.

* cited by examiner

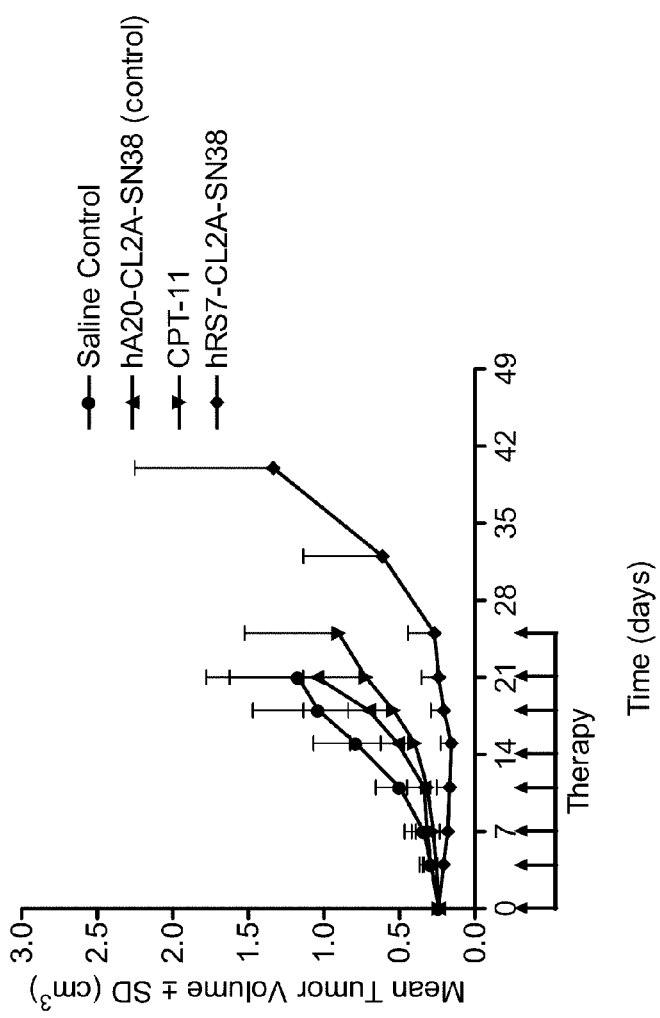

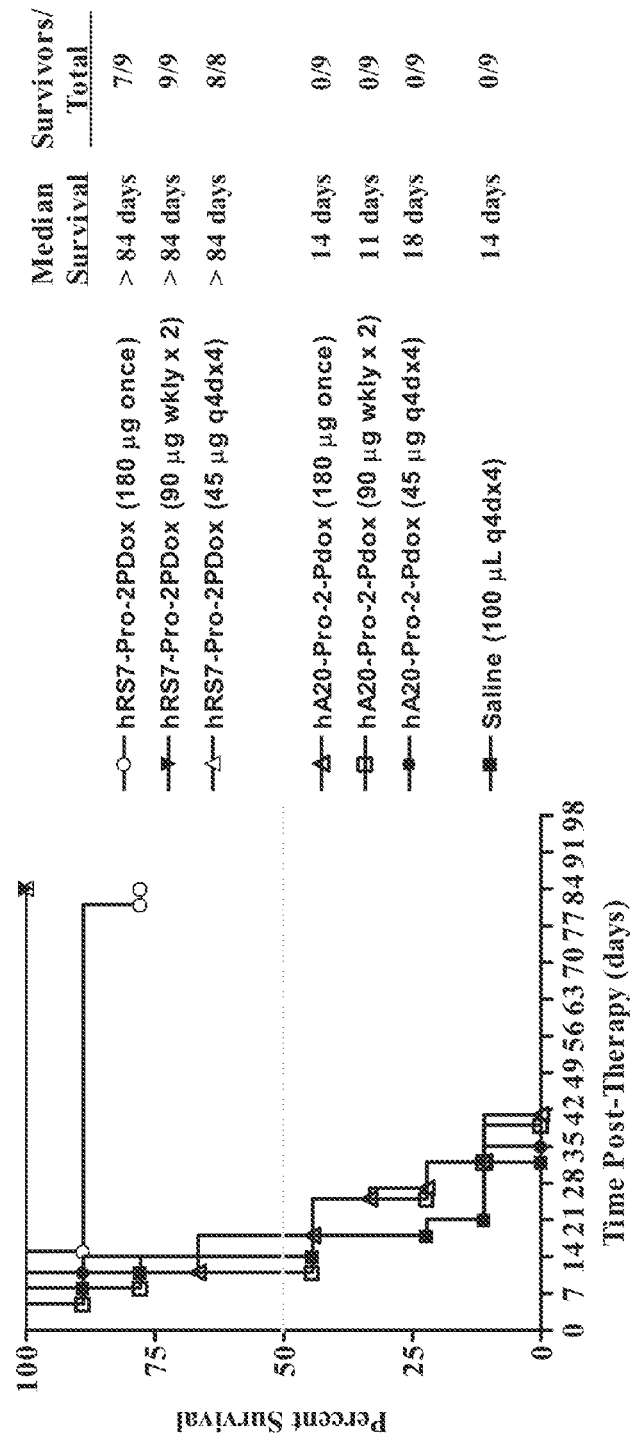

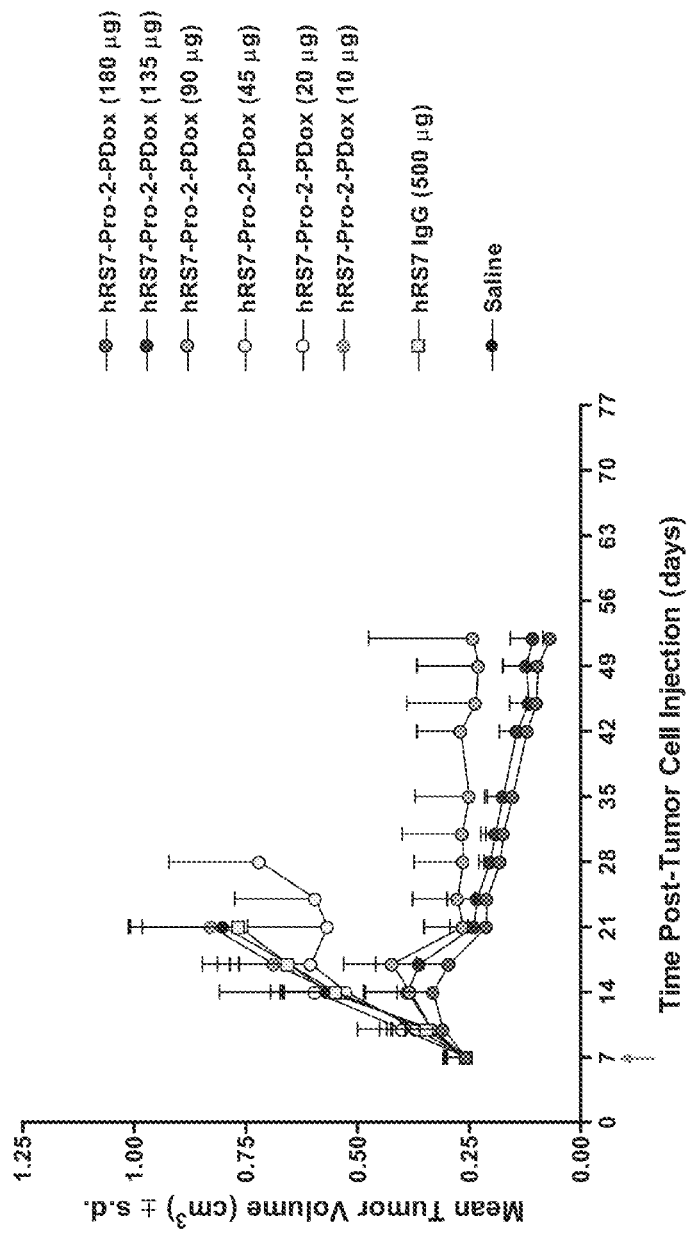

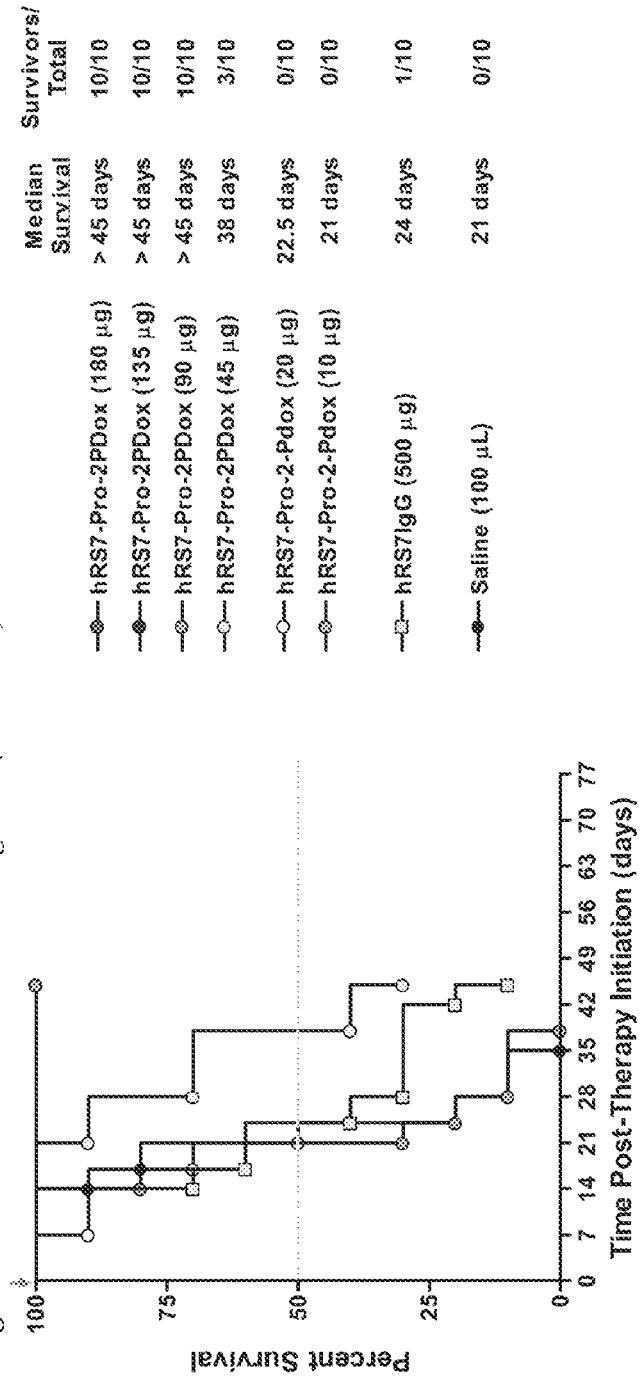

| AGENT | SN-38/IgG SUBSTITUTION RATION | FREE SN-38 (%) | HUMAN SERUM HALF-LIFE (h) | CELL BINDING: Kd (nM) (95% C.I.) | CYTOTOXICITY: IC50 (nM) (95% C.I.) |
|---|---|---|---|---|---|
| hRS7-CL2-SN-38 | 6.2 | 0.7 | 22.1 | 1.19 (0.89 to 1.49) | 4.12 (2.88 to 5.89) |
| hRS7-CL2A-SN-38 | 6.1 | 0.6 | 20.3 | 1.09 (0.97 to 1.21) | 4.24 (2.99 to 6.01) |

001
ANTIBODY-DRUG CONJUGATES AND USES THEREOF

RELATED APPLICATIONS

This application is a continuation-in-part of U.S. patent application Ser. No. 14/204,698, filed Mar. 11, 2014, which was a divisional of U.S. patent application Ser. No. 13/948,732 (now issued U.S. Pat. No. 9,028,833), filed Jul. 23, 2013, which claimed the benefit under 35 U.S.C. 119(e) of provisional U.S. patent application Ser. Nos. 61/736,684, filed Dec. 13, 2012, and 61/749,548, filed Jan. 7, 2013. This application claims the benefit under 35 U.S.C. 119(e) of provisional U.S. Patent Application Ser. No. 62/049,631, filed Sep. 12, 2014, the entire text of each priority application incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 2, 2015, is named IMM348US1_SL and is 49,315 bytes in size.

FIELD OF THE INVENTION

This invention relates to antibody-drug conjugates (ADCs) comprising one or more cytotoxic drug moieties conjugated to an antibody or antigen-binding antibody fragment. Preferably, the antibody is an anti-Trop-2 or anti-CEACAM5 antibody, conjugated to SN-38. More preferably, a linker such as CL2A may be used to attach the drug to the antibody or antibody fragment. However, other linkers and other known methods of conjugating drugs to antibodies may be utilized. Most preferably, the antibody or antigen-binding fragment thereof binds to a human antigen. The antibody or fragment may be attached to 1-12, 1-6, 1-5, 6-8 or 7-8 copies of drug moiety or drug-linker moiety per antibody or fragment. More preferably, the drug to antibody ratio may vary between 1.5:1 to 8:1. The ADCs are of use for therapy of cancers, such as breast, ovarian, cervical, endometrial, lung, prostate, colon, stomach, esophageal, bladder, renal, pancreatic, thyroid, epithelial and head-and-neck cancer. The ADC may be of particular use for treatment of cancers that are resistant to one or more standard anti-cancer therapies, such as triple-negative breast cancer, metastatic pancreatic cancer, metastatic gastrointestinal cancer or metastatic colorectal cancer. The ADCs may be used alone or as a combination therapy, along with one or more therapeutic modalities selected from the group consisting of surgery, radiation therapy, chemotherapy, immunomodulators, cytokines, chemotherapeutic agents, pro-apoptotic agents, anti-angiogenic agents, cytotoxic agents, drugs, toxins, radionuclides, RNAi, siRNA, a second antibody or antibody fragment, and an immunoconjugate. In preferred embodiments, the combination of ADC and other therapeutic modality exhibits a synergistic effect and is more effective to induce cancer cell death than either ADC or other therapeutic modality alone, or the sum of the effects of ADC and other therapeutic modality administered individually.

RELATED ART

For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed, but have had mixed success in the therapy of cancer in humans, and virtually no application in other diseases, such as infectious and autoimmune diseases. The toxic agent is most commonly a chemotherapeutic drug, although particle-emitting radionuclides, or bacterial or plant toxins, have also been conjugated to MAbs, especially for the therapy of cancer (Sharkey and Goldenberg, *CA Cancer J Clin.* 2006 July-August; 56(4):226-243) and, more recently, with radioimmunoconjugates for the preclinical therapy of certain infectious diseases (Dadachova and Casadevall, *Q J Nucl Med Mol Imaging* 2006; 50(3):193-204).

The advantages of using MAb-chemotherapeutic drug conjugates are that (a) the chemotherapeutic drug itself is structurally well defined; (b) the chemotherapeutic drug is linked to the MAb protein using very well-defined conjugation chemistries, often at specific sites remote from the MAbs' antigen binding regions; (c) MAb-chemotherapeutic drug conjugates can be made more reproducibly and usually with less immunogenicity than chemical conjugates involving MAbs and bacterial or plant toxins, and as such are more amenable to commercial development and regulatory approval; and (d) the MAb-chemotherapeutic drug conjugates are orders of magnitude less toxic systemically than radionuclide MAb conjugates, particularly to the radiation-sensitive bone marrow.

Camptothecin (CPT) and its derivatives are a class of potent antitumor agents. Irinotecan (also referred to as CPT-11) and topotecan are CPT analogs that are approved cancer therapeutics (Iyer and Ratain, *Cancer Chemother. Phamacol.* 42: S31-S43 (1998)). CPTs act by inhibiting topoisomerase I enzyme by stabilizing topoisomerase I-DNA complex (Liu, et al. in *The Camptothecins: Unfolding Their Anticancer Potential*, Liehr J. G., Giovanella, B. C. and Verschraegen (eds), NY Acad Sci., NY 922:1-10 (2000)). CPTs present specific issues in the preparation of conjugates. One issue is the insolubility of most CPT derivatives in aqueous buffers. Second, CPTs provide specific challenges for structural modification for conjugating to macromolecules. For instance, CPT itself contains only a tertiary hydroxyl group in ring-E. The hydroxyl functional group in the case of CPT must be coupled to a linker suitable for subsequent protein conjugation; and in potent CPT derivatives, such as SN-38, the active metabolite of the chemotherapeutic CPT-11, and other C-10-hydroxyl-containing derivatives such as topotecan and 10-hydroxy-CPT, the presence of a phenolic hydroxyl at the C-10 position complicates the necessary C-20-hydroxyl derivatization. Third, the lability under physiological conditions of the δ-lactone moiety of the E-ring of camptothecins results in greatly reduced antitumor potency. Therefore, the conjugation protocol is performed such that it is carried out at a pH of 7 or lower to avoid the lactone ring opening. However, conjugation of a bifunctional CPT possessing an amine-reactive group such as an active ester would typically require a pH of 8 or greater. Fourth, an intracellularly-cleavable moiety preferably is incorporated in the linker/spacer connecting the CPTs and the antibodies or other binding moieties.

A need exists for more effective methods of preparing and administering antibody-CPT conjugates, such as antibody-SN-38 conjugates. Preferably, the methods comprise optimized dosing and administration schedules that maximize efficacy and minimize toxicity of the antibody-CPT conjugates for therapeutic use in human patients.

SUMMARY

In various embodiments, the present invention concerns treatment of cancer with antibody-drug conjugates (ADCs). The ADC may be used alone or as a combination therapy with one or more other therapeutic modalities, such as surgery, radiation therapy, chemotherapy, immunomodulators, cytokines, chemotherapeutic agents, pro-apoptotic agents, anti-angiogenic agents, cytotoxic agents, drugs, toxins, radionuclides, RNAi, siRNA, a second antibody or antibody fragment, or an immunoconjugate. In preferred embodiments, the ADC may be of use for treatment of cancers for which standard therapies are not effective, such as metastatic pancreatic cancer, metastatic colorectal cancer or triple-negative breast cancer. More preferably, the combination of ADC and other therapeutic modality is more efficacious than either alone, or the sum of the effects of individual treatments.

In a specific embodiment, an anti-Trop-2 antibody may be a humanized RS7 antibody (see, e.g., U.S. Pat. No. 7,238,785, the Figures and Examples section of which are incorporated herein by reference), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6). However, as discussed below other anti-Trop-2 antibodies are known and may be used in the subject ADCs. A number of cytotoxic drugs of use for cancer treatment are well-known in the art and any such known drug may be conjugated to the antibody of interest. In a more preferred embodiment, the drug conjugated to the antibody is a camptothecin or anthracycline, most preferably SN-38 or a pro-drug form of 2-pyrrolinodoxorubicin (2-PDox) (see, e.g., U.S. patent application Ser. Nos. 14/175,089 and 14/204,698, the Figures and Examples section of each incorporated herein by reference).

In another preferred embodiment, therapeutic conjugates comprising an anti-CEACAM5 antibody (e.g., hMN-14, labretuzumab) and/or an anti-CEACAM6 antibody (e.g., hMN-3 or hMN-15) may be used to treat any of a variety of cancers that express CEACAM5 and/or CEACAM6, as disclosed in U.S. Pat. Nos. 7,541,440; 7,951,369; 5,874,540; 6,676,924 and 8,267,865, the Examples section of each incorporated herein by reference. Solid tumors that may be treated using anti-CEACAM5, anti-CEACAM6, or a combination of the two include but are not limited to breast, lung, pancreatic, esophageal, medullary thyroid, ovarian, colon, rectum, urinary bladder, mouth and stomach cancers. A majority of carcinomas, including gastrointestinal, respiratory, genitourinary and breast cancers express CEACAM5 and may be treated with the subject immunoconjugates. An hMN-14 antibody is a humanized antibody that comprises light chain variable region CDR sequences CDR1 (KASQDVGTSVA; SEQ ID NO:114), CDR2 (WTSTRHT; SEQ ID NO:97), and CDR3 (QQYSLYRS; SEQ ID NO:98), and the heavy chain variable region CDR sequences CDR1 (TYWMS; SEQ ID NO:99), CDR2 (EIHPDSSTINYAPSLKD; SEQ ID NO:100) and CDR3 (LYFGFPWFAY; SEQ ID NO:101). An hMN-3 antibody is a humanized antibody that comprises light chain variable region CDR sequences CDR1 (RSSQSIVHSNGNTYLE, SEQ ID NO:102), CDR2 (KVSNRFS, SEQ ID NO:103) and CDR3 (FQGSHVPPT, SEQ ID NO:104) and the heavy chain CDR sequences CDR1 (NYGMN, SEQ ID NO:105), CDR2 (WINTYTGEPTYADDFKG, SEQ ID NO:106) and CDR3 (KGWMDFNSSLDY, SEQ ID NO:107). An hMN-15 antibody is a humanized antibody that comprises light chain variable region CDR sequences SASSRVSYIH (SEQ ID NO:108); GTSTLAS (SEQ ID NO:109); and QQWSYNPPT (SEQ ID NO:110); and heavy chain variable region CDR sequences DYYMS (SEQ ID NO:111); FIANKANGHTTDYSPSVKG (SEQ ID NO:112); and DMGIRWNFDV (SEQ ID NO:113).

The antibody moiety may be a monoclonal antibody, an antigen-binding antibody fragment, a bispecific or other multivalent antibody, or other antibody-based molecule. The antibody can be of various isotypes, preferably human IgG1, IgG2, IgG3 or IgG4, more preferably comprising human IgG1 hinge and constant region sequences. The antibody or fragment thereof can be a chimeric, a humanized, or a human antibody, as well as variations thereof, such as half-IgG4 antibodies (referred to as "unibodies"), as described by van der Neut Kolfschoten et al. (*Science* 2007; 317:1554-1557). More preferably, the antibody or fragment thereof may be designed or selected to comprise human constant region sequences that belong to specific allotypes, which may result in reduced immunogenicity when the ADC is administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

The drug to be conjugated to the antibody or antibody fragment may be selected from the group consisting of an anthracycline, a camptothecin, a tubulin inhibitor, a maytansinoid, a calicheamycin, an auristatin, a nitrogen mustard, an ethylenimine derivative, an alkyl sulfonate, a nitrosourea, a triazene, a folic acid analog, a taxane, a COX-2 inhibitor, a pyrimidine analog, a purine analog, an antibiotic, an enzyme inhibitor, an epipodophyllotoxin, a platinum coordination complex, a vinca alkaloid, a substituted urea, a methyl hydrazine derivative, an adrenocortical suppressant, a hoinione antagonist, an antimetabolite, an alkylating agent, an antimitotic, an anti-angiogenic agent, a tyrosine kinase inhibitor, an mTOR inhibitor, a heat shock protein (HSP90) inhibitor, a proteosome inhibitor, an HDAC inhibitor, a pro-apoptotic agent, and a combination thereof.

Specific drugs of use may be selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyanomorpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839.

Preferred optimal dosing of the subject ADCs may include a dosage of between 4 mg/kg and 18 mg/kg, preferably given either weekly, twice weekly or every other week. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. Exemplary dosages of use may include 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Preferred dosages are 4, 6, 8, 9, 10, 12, 14, 16 or 18 mg/kg. More preferred dosages are 6-12, 6-8, 7-8, 8-10, 10-12 or 8-12 mg/ml. The person of ordinary skill will realize that a variety of factors, such as age, general health, specific organ function or weight, as well as effects of prior therapy on specific organ systems (e.g., bone marrow) may be considered in selecting an optimal dosage of ADC, and that the dosage and/or frequency of administration may be increased or decreased during the course of therapy. The dosage may be repeated as needed, with evidence of tumor shrinkage observed after as few as 4 to 8 doses. The optimized dosages and schedules of administration disclosed herein show unexpected superior efficacy and reduced toxicity in human subjects, which could not have been predicted from animal model studies. Surprisingly, the superior efficacy allows treatment of tumors that were previously found to be resistant to one or more standard anti-cancer therapies. More surprisingly, the treatment has been found effective in tumors that were previously resistant to camptothecins, such as irinotecan, the parent compound of SN-38.

The ADCs are of use for therapy of cancers, such as breast, ovarian, cervical, endometrial, lung, prostate, colon, stomach, esophageal, bladder, renal, pancreatic, thyroid, epithelial or head-and-neck cancer. The ADC may be of particular use for treatment of cancers that are resistant to one or more standard anti-cancer therapies, such as a metastatic colon cancer, triple-negative breast cancer, a HER+, ER+, progesterone+breast cancer, metastatic non-small-cell lung cancer (NSCLC), metastatic pancreatic cancer, metastatic renal cell carcinoma, metastatic gastric cancer, metastatic prostate cancer, or metastatic small-cell lung cancer.

BRIEF DESCRIPTION OF THE DRAWINGS

FIG. 2. Preclinical in vivo therapy of athymic nude mice, bearing BxPC3 human pancreatic carcinoma, with anti-TROP2-CL2A-SN-38 conjugates compared to controls.

FIG. 7. Effect of different dosing schedules of hRS7-pro-2-PDox on survival in nude mice with NCI-N87 human gastric carcinoma xenografts.

FIG. 9. Effect of different single doses of hRS7-pro-2-PDox on growth of human gastric carcinoma xenografts.

FIG. 10. Effect of different single doses of hRS7-pro-2-PDox on survival of mice bearing human gastric carcinoma xenografts.

DETAILED DESCRIPTION

Definitions

Figure 1:
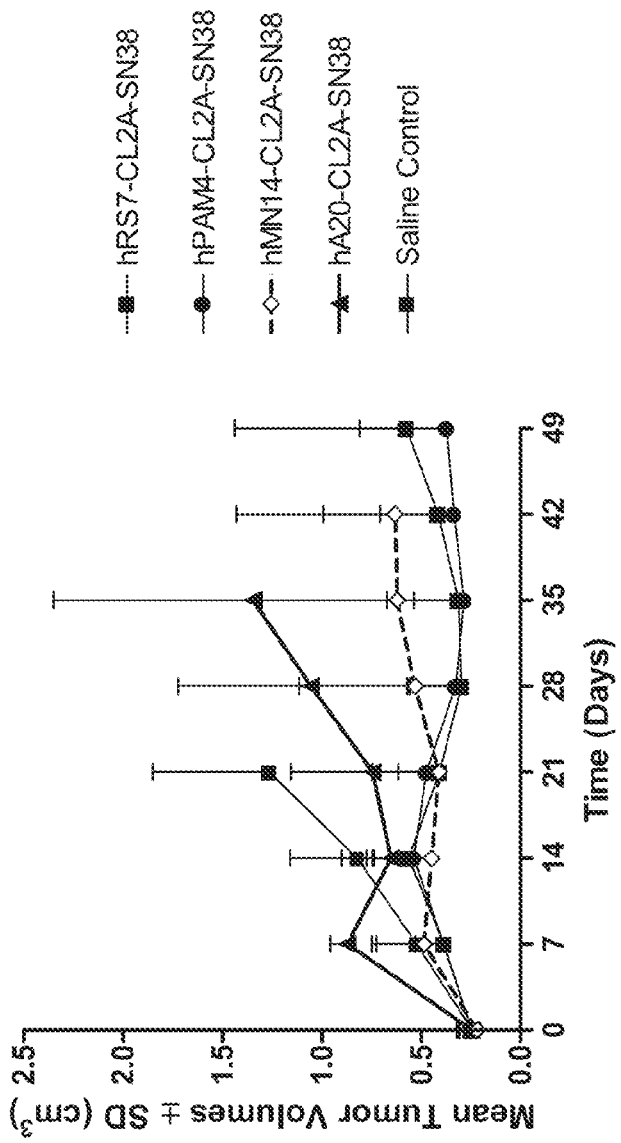
FIG. 1. Preclinical in vivo therapy of athymic nude mice, bearing Capan 1 human pancreatic carcinoma, with SN-38 conjugates of hRS7 (anti-Trop-2), hPAM4 (anti-MUC5ac), hMN-14 (anti-CEACAM5) or non-specific control hA20 (anti-CD20).
Figure 3C:
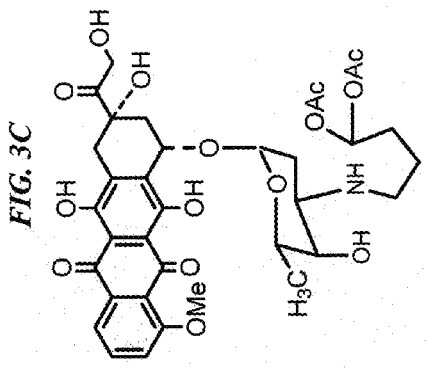
FIG. 3C. Structure of a prodrug form of 2-pyrrolinodoxorubicin,(pro-2-PDox). "Me" is a methyl group and "Ac" is an acetyl group.
Figure 3B:
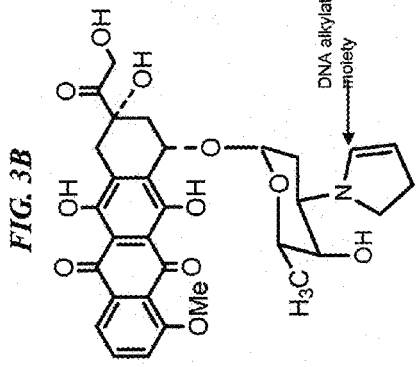
FIG. 3B. Structure of 2-pyrrolinodoxorubicin,(2-PDox). "Me" is a methyl group.
Figure 3A:
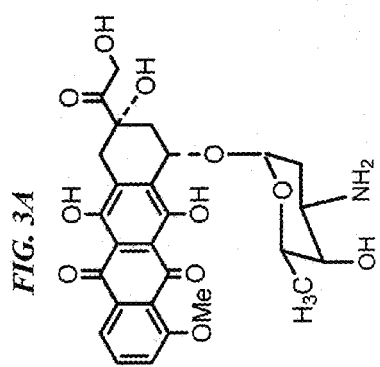
FIG. 3A. Structure of doxorubicin. "Me" is a methyl group.
Figure 3D:
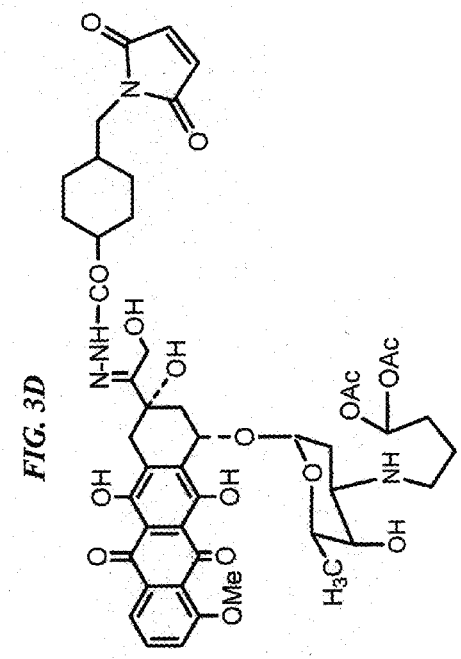
FIG. 3D. Structure of a maleimide-activated form of pro-2-PDox, for antibody coupling. "Me" is a methyl group and "Ac" is an acetyl group.

Unless otherwise specified, "a" or "an" means one or more.

As used herein, "about" means plus or minus 10%. For example, "about 100" would include any number between 90 and 110.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, Fab', Fab, Fv, sFv and the like. Antibody fragments may also include single domain antibodies and IgG4 half-molecules, as discussed below. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins").

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

A human antibody is, e.g., an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous murine heavy chain and light chain loci. The transgenic mice can synthesize human antibodies specific for particular antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, the Examples section of which are incorporated herein by reference.

A therapeutic agent is a compound, molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. Therapeutic agents of use are described in more detail below.

An immunoconjugate is an antibody, antibody fragment or fusion protein conjugated to at least one therapeutic and/or diagnostic agent.

A multispecific antibody is an antibody that can bind simultaneously to at least two targets that are of different structure, e.g., two different antigens, two different epitopes on the same antigen, or a hapten and/or an antigen or epitope. Multispecific, multivalent antibodies are constructs that have more than one binding site, and the binding sites are of different specificity.

A bispecific antibody is an antibody that can bind simultaneously to two different targets. Bispecific antibodies (bsAb) and bispecific antibody fragments (bsFab) may have at least one arm that specifically binds to, for example, a tumor-associated antigen and at least one other arm that specifically binds to a targetable conjugate that bears a therapeutic or diagnostic agent. A variety of bispecific fusion proteins can be produced using molecular engineering.

Anti-Trop-2 Antibodies

The subject ADCs may include an antibody or fragment thereof that binds to Trop-2. In a specific preferred embodiment, the anti-Trop-2 antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WIN- TYTGEPTYTDDFKG, SEQ ID NO:5) and CDR3 (GGF-GSSYWYFDV, SEQ ID NO:6).

The RS7 antibody was a murine IgG$_1$ raised against a crude membrane preparation of a human primary squamous cell lung carcinoma. (Stein et al., Cancer Res. 50: 1330, 1990) The RS7 antibody recognizes a 46-48 kDa glycoprotein, characterized as cluster 13. (Stein et al., Int. J. Cancer Supp. 8:98-102, 1994) The antigen was designated as EGP-1 (epithelial glycoprotein-1), but is also referred to as Trop-2.

Trop-2 is a type-I transmembrane protein and has been cloned from both human (Fornaro et al., Int J Cancer 1995; 62:610-8) and mouse cells (Sewedy et al., Int J Cancer 1998; 75:324-30). In addition to its role as a tumor-associated calcium signal transducer (Ripani et al., Int J Cancer 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5).

The growing interest in Trop-2 as a therapeutic target for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell (Fong et al., Modern Pathol 2008; 21:186-91) carcinomas. The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

Flow cytometry and immunohistochemical staining studies have shown that the RS7 MAb detects antigen on a variety of tumor types, with limited binding to normal human tissue (Stein et al., 1990). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., 1990; Stein et al., 1991).

Strong RS7 staining has been demonstrated in tumors from the lung, breast, bladder, ovary, uterus, stomach, and prostate. (Stein et al., Int. J. Cancer 55:938, 1993) The lung cancer cases comprised both squamous cell carcinomas and adenocarcinomas. (Stein et al., Int. J. Cancer 55:938, 1993) Both cell types stained strongly, indicating that the RS7 antibody does not distinguish between histologic classes of non-small-cell carcinoma of the lung.

The RS7 MAb is rapidly internalized into target cells (Stein et al., 1993). The internalization rate constant for RS7 MAb is intermediate between the internalization rate constants of two other rapidly internalizing MAbs, which have been demonstrated to be useful for immunotoxin production. (Id.) It is well documented that internalization of immunotoxin conjugates is a requirement for anti-tumor activity. (Pastan et al., Cell 47:641, 1986) Internalization of drug immunoconjugates has been described as a major factor in anti-tumor efficacy. (Yang et al., Proc. Nat'l Acad. Sci. USA 85: 1189, 1988) Thus, the RS7 antibody exhibits several important properties for therapeutic applications.

While the hRS7 antibody is preferred, other anti-Trop-2 antibodies are known and/or publicly available and in alternative embodiments may be utilized in the subject ADCs. While humanized or human antibodies are preferred for reduced immunogenicity, in alternative embodiments a chimeric antibody may be of use. As discussed below, methods of antibody humanization are well known in the art and may be utilized to convert an available murine or chimeric antibody into a humanized form.

Anti-Trop-2 antibodies are commercially available from a number of sources and include LS-C126418, LS-C178765, LS-C126416, LS-C126417 (LifeSpan BioSciences, Inc., Seattle, Wash.); 10428-MM01, 10428-MMO2, 10428-R001, 10428-R030 (Sino Biological Inc., Beijing, China); MR54 (eBioscience, San Diego, Calif.); sc-376181, sc-376746, Santa Cruz Biotechnology (Santa Cruz, Calif.); MM0588-49D6, (Novus Biologicals, Littleton, Colo.); ab79976, and ab89928 (ABCAM®, Cambridge, Mass.).

Other anti-Trop-2 antibodies have been disclosed in the patent literature. For example, U.S. Publ. No. 2013/0089872 discloses anti-Trop-2 antibodies K5-70 (Accession No. FERM BP-11251), K5-107 (Accession No. FERM BP-11252), K5-116-2-1 (Accession No. FERM BP-11253), T6-16 (Accession No. FERM BP-11346), and T5-86 (Accession No. FERM BP-11254), deposited with the International Patent Organism Depositary, Tsukuba, Japan. U.S. Pat. No. 5,840,854 disclosed the anti-Trop-2 monoclonal antibody BR110 (ATCC No. HBI 1698). U.S. Pat. No. 7,420,040 disclosed an anti-Trop-2 antibody produced by hybridoma cell line AR47A6.4.2, deposited with the IDAC (International Depository Authority of Canada, Winnipeg, Canada) as accession number 141205-05. U.S. Pat. No. 7,420,041 disclosed an anti-Trop-2 antibody produced by hybridoma cell line AR52A301.5, deposited with the IDAC as accession number 141205-03. U.S. Publ. No. 2013/0122020 disclosed anti-Trop-2 antibodies 3E9, 6G11, 7E6, 15E2, 18B1. Hybridomas encoding a representative antibody were deposited with the American Type Culture Collection (ATCC), Accession Nos. PTA-12871 and PTA-12872. U.S. Pat. No. 8,715,662 discloses anti-Trop-2 antibodies produced by hybridomas deposited at the AID-ICLC (Genoa, Italy) with deposit numbers PD 08019, PD 08020 and PD 08021. U.S. Patent Application Publ. No. 20120237518 discloses anti-Trop-2 antibodies 77220, KM4097 and KM4590. U.S. Pat. No. 8,309,094 (Wyeth) discloses antibodies A1 and A3, identified by sequence listing. The Examples section of each patent or patent application cited above in this paragraph is incorporated herein by reference. Non-patent publication Lipinski et al. (1981, Proc Natl. Acad Sci USA, 78:5147-50) disclosed anti-Trop-2 antibodies 162-25.3 and 162-46.2.

Numerous anti-Trop-2 antibodies are known in the art and/or publicly available. As discussed below, methods for preparing antibodies against known antigens were routine in the art. The sequence of the human Trop-2 protein was also known in the art (see, e.g., GenBank Accession No. CAA54801.1). Methods for producing humanized, human or chimeric antibodies were also known. The person of ordinary skill, reading the instant disclosure in light of general knowledge in the art, would have been able to make and use the genus of anti-Trop-2 antibodies in the subject ADCs.

Use of anti-Trop-2 antibodies has been disclosed for immunotherapeutics other than ADCs. The murine IgG2a antibody edrecolomab (PANOREX®) has been used for treatment of colorectal cancer, although the murine antibody is not well suited for human clinical use (Baeuerle & Gires, 2007, Br. J Cancer 96:417-423). Low-dose subcutaneous administration of ecrecolomab was reported to induce humoral immune responses against the vaccine antigen (Baeuerle & Gires, 2007). Adecatumumab (MT201), a fully human anti-Trop-2 antibody, has been used in metastatic breast cancer and early-stage prostate cancer and is reported to act through ADCC and CDC activity (Baeuerle & Gires, 2007). MT110, a single-chain anti-Trop-2/anti-CD3 bispecific antibody construct has reported efficacy against ovarian cancer (Baeuerle & Gires, 2007). Catumaxomab, a hybrid mouse/rat antibody with binding affinity for Trop-2, CD3 and Fc receptor, was reported to be active against ovarian cancer (Baeuerle & Gires, 2007). Proxinium, an immunotoxin comprising anti-Trop-2 single-chain antibody fused to *Pseudomonas* exotoxin, has been tested in head-and-neck and bladder cancer (Baeuerle & Gires, 2007). None of these studies contained any disclosure of the use of anti-Trop-2 antibody-drug conjugates.

Anti-CEA Antibodies

Certain embodiments may concern use of conjugated antibodies against CEACAM5 or CEACAM6. CEA (CEACAM5) is an oncofetal antigen commonly expressed in a number of epithelial cancers, most commonly those arising in the colon but also in the breast, lung, pancreas, thyroid (medullary type) and ovary (Goldenberg et al., J. Natl. Cancer Inst. 57: 11-22, 1976; Shively, et al., Crit. Rev. Oncol. Hematol. 2:355-399, 1985). The human CEA gene family is composed of 7 known genes belonging to the CEACAM subgroup. These subgroup members are mainly associated with the cell membrane and show a complex expression pattern in normal and cancerous tissues. The CEACAM5 gene, also known as CD66e, codes for the CEA protein (Beauchemin et al., Exp Cell Res 252:243, 1999). CEACAM5 was first described in 1965 as a gastrointestinal oncofetal antigen (Gold et al., J Exp Med 122:467-481, 1965), but is now known to be overexpressed in a majority of carcinomas, including those of the gastrointestinal tract, the respiratory and genitourinary systems, and breast cancer (Goldenberg et al., J Natl Cancer Inst. 57:11-22, 1976; Shively and Beatty, Crit Rev Oncol Hematol 2:355-99, 1985).

CEACAM6 (also called CD66c or NCA-90) is a nonspecific cross-reacting glycoprotein antigen that shares some, but not all, antigenic determinants with CEACAM5 (Kuroki et al., Biochem Biophys Res Comm 182:501-06, 1992). CEACAM6 is expressed on granulocytes and epithelia from various organs, and has a broader expression zone in proliferating cells of hyperplastic colonic polyps and adenomas, compared with normal mucosa, as well as by many human cancers (Scholzel et al., Am J Pathol 157:1051-52, 2000; Kuroki et al., Anticancer Res 19:5599-5606, 1999). Relatively high serum levels of CEACAM6 are found in patients with lung, pancreatic, breast, colorectal, and hepatocellular carcinomas. The amount of CEACAM6 does not correlate with the amount of CEACAM5 expressed (Kuroki et al., Anticancer Res 19:5599-5606, 1999).

Expression of CEACAM6 in colorectal cancer correlates inversely with cellular differentiation (Ilantzis et al., Neoplasia 4:151-63, 2002) and is an independent prognostic factor associated with a higher risk of relapse (Jantscheff et al., J Clin Oncol 21:3638-46, 2003). Both CEACAM5 and CEACAM6 have a role in cell adhesion, invasion and metastasis. CEACAM5 has been shown to be involved in both homophilic (CEA to CEA) and heterophilic (CEA binding to non-CEA molecules) interactions (Bechimol et al., Cell 57:327-34, 1989; Oikawa et al., Biochem Biophys Res Comm 164:39-45, 1989), suggesting to some that it is an intercellular adhesion molecule involved in cancer invasion and metastasis (Thomas et al., Cancer Lett 92:59-66, 1995). These reactions were completely inhibited by the Fab' fragment of an anti-CEACAM5 antibody (Oikawa et al., Biochem Biophys Res Comm 164:39-45, 1989). CEACAM6 also exhibits homotypic binding with other members of the CEA family and heterotypic interactions with integrin receptors (Stanners and Fuks, In: *Cell Adhesion and Communication by the CEA Family*, (Stanners ed.) Vol. 5, pp. 57-72, Harwood Academic Publ., Amsterdam, 1998). Antibodies that target the N-domain of CEACAM6 interfere with cell-cell interactions (Yamanka et al. Biochem Biophys Res Comm 219:842-47, 1996). Many breast, pancreatic, colonic and non-small-cell lung cancer (NSCLC) cell lines express CEACAM6 and anti-CEACAM6 antibody inhibits in vitro migration, invasion, and adhesion of antigen-positive cells (Blumenthal et al, Cancer Res 65:8809-17, 2005).

Anti-CEA antibodies are classified into different categories, depending on their cross-reactivity with antigens other than CEA. Anti-CEA antibody classification was described by Primus and Goldenberg, U.S. Pat. No. 4,818,709 (incorporated herein by reference from Col. 3, line 5 through Col. 26, line 49). The classification of anti-CEA antibodies is determined by their binding to CEA, meconium antigen (MA) and nonspecific crossreacting antigen (NCA). Class I anti-CEA antibodies bind to all three antigens. Class II antibodies bind to MA and CEA, but not to NCA. Class III antibodies bind only to CEA (U.S. Pat. No. 4,818,709). Examples of each class of anti-CEA antibody are known, such as MN-3, MN-15 and NP-1 (Class I); MN-2, NP-2 and NP-3 (Class II); and MN-14 and NP-4 (Class III) (U.S. Pat. No. 4,818,709; Blumenthal et al. BMC Cancer 7:2 (2007)).

The epitopic binding sites of various anti-CEA antibodies have also been identified. The MN-15 antibody binds to the A1B1 domain of CEA, the MN-3 antibody binds to the N-terminal domain of CEA and the MN-14 antibody binds to the A3B3 (CD66e) domain of CEA (Blumenthal et al. BMC Cancer 7:2 (2007)). There is no direct correlation between epitopic binding site and class of anti-CEA antibody. For example, MN-3 and MN-15 are both Class I anti-CEA antibodies, reactive with NCA, MA and CEA, but bind respectively to the N-terminal and A1B1 domains of CEA. Primus and Goldenberg (U.S. Pat. No. 4,818,709) reported a complicated pattern of cross-blocking activity between the different anti-CEA antibodies, with NP-1 (Class I) and NP-2 (Class II) cross-blocking binding to CEA of each other, but neither blocking binding of NP-3 (Class II). However, by definition Class I anti-CEA antibodies bind to both CEACAM5 and CEACAM6, while Class III anti-CEA antibodies bind only to CEACAM5.

Anti-CEA antibodies have been suggested for therapeutic treatment of a variety of cancers. For example, medullary thyroid cancer (MTC) confined to the thyroid gland is generally treated by total thyroidectomy and central lymph node dissection. However, disease recurs in approximately 50% of these patients. In addition, the prognosis of patients with unresectable disease or distant metastases is poor, less than 30% survive 10 years (Rossi et al., Amer. J. Surgery, 139:554 (1980); Samaan et al., J. Clin. Endocrinol. Metab., 67:801 (1988); Schroder et al., Cancer, 61:806 (1988)). These patients are left with few therapeutic choices (Principles and Practice of Oncology, DeVita, Hellman and Rosenberg (eds.), New York: JB Lippincott Co., pp. 1333-1435 (1989); Cancer et al., Current Problems Surgery, 22: 1 (1985)). The Class III anti-CEA antibody MN-14 has been reported to be effective for therapy of human medullary thyroid carcinoma in an animal xenograft model system, when used in conjunction with pro-apoptotic agents such as DTIC, CPT-11 and 5-fluorouracil (U.S. patent application Ser. No. 10/680,734, the Examples section of which is incorporated herein by reference). The Class III anti-CEA antibody reportedly sensitized cancer cells to therapy with chemotherapeutic agents and the combination of antibody and chemotherapeutic agent was reported to have synergistic effects on tumors compared with either antibody or chemotherapeutic agent alone (U.S. Ser. No. 10/680,734). Anti-CEA antibodies of different classes (such as MN-3, MN-14 and MN-15) have been proposed for use in treating a variety of tumors.

In a preferred embodiment, therapeutic conjugates comprising an anti-CEACAM5 antibody (e.g., hMN-14, labretuzumab) and/or an anti-CEACAM6 antibody (e.g., hMN-3 or hMN-15) may be used to treat any of a variety of cancers that express CEACAM5 and/or CEACAM6, as disclosed in U.S. Pat. Nos. 7,541,440; 7,951,369; 5,874,540; 6,676,924 and 8,267,865, the Examples section of each incorporated herein by reference. Solid tumors that may be treated using anti-CEACAM5, anti-CEACAM6, or a combination of the two include but are not limited to breast, lung, pancreatic, esophageal, medullary thyroid, ovarian, colon, rectum, urinary bladder, mouth and stomach cancers. A majority of carcinomas, including gastrointestinal, respiratory, genitourinary and breast cancers express CEACAM5 and may be treated with the subject immunoconjugates. An hMN-14 antibody is a humanized antibody that comprises light chain variable region CDR sequences CDR1 (KASQDVGTSVA; SEQ ID NO:114), CDR2 (WTSTRHT; SEQ ID NO:97), and CDR3 (QQYSLYRS; SEQ ID NO:98), and the heavy chain variable region CDR sequences CDR1 (TYWMS; SEQ ID NO:99), CDR2 (EIHPDSSTINYAPSLKD; SEQ ID NO:100) and CDR3 (LYFGFPWFAY; SEQ ID NO:101). An hMN-3 antibody is a humanized antibody that comprises light chain variable region CDR sequences CDR1 (RSSQSIVHSNGNTYLE, SEQ ID NO:102), CDR2 (KVSNRFS, SEQ ID NO:103) and CDR3 (FQGSHVPPT, SEQ ID NO:104) and the heavy chain CDR sequences CDR1 (NYGMN, SEQ ID NO:105), CDR2 (WINTYTGEPTYADDFKG, SEQ ID NO:106) and CDR3 (KGWMDFNSSLDY, SEQ ID NO:107). An hMN-15 antibody is a humanized antibody that comprises light chain variable region CDR sequences SASSRVSYIH (SEQ ID NO:108); GTSTLAS (SEQ ID NO:109); and QQWSYNPPT (SEQ ID NO:110); and heavy chain variable region CDR sequences DYYMS (SEQ ID NO:111); FIANKANGHTTDYSPSVKG (SEQ ID NO:112); and DMGIRWNFDV (SEQ ID NO:113).

Although use of MN-14, MN-15 or MN-3 is preferred, other antibodies against CEACAM5 or CEACAM6 are known in the art and may be utilized as immunoconjugates, such as SN-38 conjugates. Another exemplary antibody against CEACAM5 is the anti-CEACAM5 CC4 antibody (e.g., Zheng et al., 2011, PLoS One 6:e21146). Antibodies against CEACAM5 or CEACAM6 are available from numerous commercial sources, including LS-C6031, LS-B7292, LS-C338757 (LSBio, Seattle, Wash.); SAB1307198, GW22478, HPA019758 (Sigma-Aldrich, St. Louis, Mo.); sc-23928, sc-59872, sc-52390 (Santa Cruz Biotechnology, Santa Cruz, Calif.); and ab78029 (AB-CAM®, Cambridge, Mass.). Any such known anti-CEACAM5 or anti-CEACAM6 antibody may be used in the immunoconjugates disclosed herein.

Antibody Preparation

Techniques for preparing monoclonal antibodies against virtually any target antigen, such as Trop-2 or CEACAM5, are well known in the art. See, for example, Köhler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 6: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et aL, Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, *Comb. Chem. High Throughput Screen.* 8:117-26; Brekke and Loset, 2003, *Curr. Opin. Pharmacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the µ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Known Antibodies and Target Antigens

As discussed above, in preferred embodiments the ADCs are of use for treatment of cancer. In certain embodiments, the target cancer may express one or more target tumor-associated antigens (TAAs). Particular antibodies that may be of use for therapy of cancer include, but are not limited to, LL1 (anti-CD74), LL2 or RFB4 (anti-CD22), veltuzumab (hA20, anti-CD20), rituximab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as Trop-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,151,164), hA19 (U.S. Pat. No. 7,109,304), hIMMU-31 (U.S. Pat. No. 7,300,655), hLL1 (U.S. Pat. No. 7,312,318), hLL2 (U.S. Pat. No. 5,789,554), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Other useful tumor-associated antigens that may be targeted include carbonic anhydrase IX, B7, CCL19, CCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD47, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., AVASTIN®, fibronectin splice variant), ED-B fibronectin (e.g., L19), EGP-1 (Trop-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-β, HMGB-1, hypoxia inducible factor (HIF), HM1.24, HER-2/neu, histone H2B, histone H3, histone H4, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (P1GF), PSA (prostate-specific antigen), PSMA, PAM4 antigen, PD-1 receptor, PD-L1, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), Trop-2, VEGFR, RANTES, T101, as well as cancer stem cell antigens, complement factors C3, C3a, C3b, C5a, C5, and an oncogene product.

Cancer stem cells, which are ascribed to be more therapy-resistant precursor malignant cell populations (Hill and Penis, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3): 385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8). Another useful target for breast cancer therapy is the LIV-1 antigen described by Taylor et al. (*Biochem. J.* 2003; 375: 51-9).

Checkpoint inhibitor antibodies have been used in cancer therapy. Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response against tumor tissues. Exemplary checkpoint inhibitor antibodies against cytotoxic T-lymphocyte antigen 4 (CTLA4, also known as CD152), programmed cell death protein 1 (PD1, also known as CD279) and programmed cell death 1 ligand 1 (PD-L1, also known as CD274), may be used in combination with one or more other agents to enhance the effectiveness of immune response against disease cells, tissues or pathogens. Exemplary anti-PD1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.). Anti-PD1 antibodies are commercially available, for example from ABCAM (AB137132), BIOLEGEND® (EH12.2H7, RMP1-14) and AFFYMETRIX EBIOSCIENCE (J105, J116, MIH4). Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1). Exemplary anti-CTLA4 antibodies include ipilimumab (Bristol-Myers Squibb) and tremelimumab (PFIZER). Anti-PD1 antibodies are commercially available, for example from ABCAM (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, *J Transl Med* 11:89).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, and colon (e.g., Meyer-Siegler et al., 2004, *BMC Cancer* 12:34; Shachar & Haran, 2011, *Leuk Lymphoma* 52:1446-54). Milatuzumab (hLL1) is an exemplary anti-CD74 antibody of therapeutic use for treatment of MIF-mediated diseases.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.)

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including tumor-associated antigens, have been deposited at the ATCC and/or have published variable region sequences and are available for use in the claimed methods and compositions. See, e.g., U.S. Pat. Nos. 7,312,318; 7,282, 567; 7,151,164; 7,074,403; 7,060,802; 7,056,509; 7,049, 060; 7,045,132; 7,041,803; 7,041,802; 7,041,293; 7,038, 018; 7,037,498; 7,012,133; 7,001,598; 6,998,468; 6,994, 976; 6,994,852; 6,989,241; 6,974,863; 6,965,018; 6,964, 854; 6,962,981; 6,962,813; 6,956,107; 6,951,924; 6,949, 244; 6,946,129; 6,943,020; 6,939,547; 6,921,645; 6,921, 645; 6,921,533; 6,919,433; 6,919,078; 6,916,475; 6,905, 681; 6,899,879; 6,893,625; 6,887,468; 6,887,466; 6,884, 594; 6,881,405; 6,878,812; 6,875,580; 6,872,568; 6,867, 006; 6,864,062; 6,861,511; 6,861,227; 6,861,226; 6,838, 282; 6,835,549; 6,835,370; 6,824,780; 6,824,778; 6,812, 206; 6,793,924; 6,783,758; 6,770,450; 6,767,711; 6,764, 688; 6,764,681; 6,764,679; 6,743,898; 6,733,981; 6,730, 307; 6,720,155; 6,716,966; 6,709,653; 6,693,176; 6,692, 908; 6,689,607; 6,689,362; 6,689,355; 6,682,737; 6,682, 736; 6,682,734; 6,673,344; 6,653,104; 6,652,852; 6,635, 482; 6,630,144; 6,610,833; 6,610,294; 6,605,441; 6,605, 279; 6,596,852; 6,592,868; 6,576,745; 6,572; 856; 6,566, 076; 6,562,618; 6,545,130; 6,544,749; 6,534,058; 6,528, 625; 6,528,269; 6,521,227; 6,518,404; 6,511,665; 6,491, 915; 6,488,930; 6,482,598; 6,482,408; 6,479,247; 6,468, 531; 6,468,529; 6,465,173; 6,461,823; 6,458,356; 6,455, 044; 6,455,040, 6,451,310; 6,444,206, 6,441,143; 6,432, 404; 6,432,402; 6,419,928; 6,413,726, 6,406,694; 6,403, 770; 6,403,091; 6,395,276; 6,395,274; 6,387,350; 6,383, 759; 6,383,484; 6,376,654; 6,372,215; 6,359,126; 6,355, 481; 6,355,444; 6,355,245; 6,355,244; 6,346,246; 6,344, 198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Stickler et al., 2011). It has been reported that G1m1 antibodies contain allotypic sequences that tend to induce an immune response when administered to non-G1m1 (nG1m1) recipients, such as G1m3 patients (Stickler et al., 2011). Non-G1m1 allotype antibodies are not as immunogenic when administered to G1m1 patients (Stickler et al., 2011).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown below for the exemplary antibodies rituximab (SEQ ID NO:7) and veltuzumab (SEQ ID NO:8).

```
Rituximab heavy chain variable region sequence
                                        (SEQ ID NO: 7)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

```
-continued
Veltuzumab heavy chain variable region
                                        (SEQ ID NO: 8)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Krill allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CHI) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | |
|---|---|---|---|---|---|
| | Complete allotype | 214 (allotype) | 356/358 (allotype) | | 431 (allotype) |
| Rituximab | G1m17,1 | K 17 | D/L | 1 | A — |
| Veltuzumab | G1m3 | R 3 | E/M | — | A — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Nanobodies

Nanobodies are single-domain antibodies of about 12-15 kDa in size (about 110 amino acids in length). Nanobodies can selectively bind to target antigens, like full-size antibodies, and have similar affinities for antigens. However, because of their much smaller size, they may be capable of better penetration into solid tumors. The smaller size also contributes to the stability of the nanobody, which is more resistant to pH and temperature extremes than full size antibodies (Van Der Linden et al., 1999, Biochim Biophys Act 1431:37-46). Single-domain antibodies were originally developed following the discovery that camelids (camels, alpacas, llamas) possess fully functional antibodies without light chains (e.g., Hamsen et al., 2007, Appl Microbiol Biotechnol 77:13-22). The heavy-chain antibodies consist of a single variable domain ($V_{HH}$) and two constant domains ($C_H2$ and $C_H3$). Like antibodies, nanobodies may be developed and used as multivalent and/or bispecific constructs. Humanized forms of nanobodies are in commercial development that are targeted to a variety of target antigens, such as IL-6R, vWF, TNF, RSV, RANKL, IL-17A & F and IgE (e.g., ABLYNX, Ghent, Belgium), with potential clinical use in cancer and other disorders (e.g., Saerens et al., 2008, Curr Opin Pharmacol 8:600-8; Muyldermans, 2013, Ann Rev Biochem 82:775-97; Ibanez et al., 2011, J Infect Dis 203: 1063-72).

The plasma half-life of nanobodies is shorter than that of full-size antibodies, with elimination primarily by the renal route. Because they lack an Fc region, they do not exhibit complement dependent cytotoxicity.

Nanobodies may be produced by immunization of camels, llamas, alpacas or sharks with target antigen, following by isolation of mRNA, cloning into libraries and screening for antigen binding. Nanobody sequences may be humanized by standard techniques (e.g., Jones et al., 1986, Nature 321: 522, Riechmann et al., 1988, Nature 332: 323, Verhoeyen et al., 1988, Science 239: 1534, Carter et al., 1992, Proc. Nat'l Acad. Sci. USA 89: 4285, Sandhu, 1992, Crit. Rev. Biotech. 12: 437, Singer et al., 1993, J. Immun. 150: 2844). Humanization is relatively straight-forward because of the high homology between camelid and human FR sequences.

In various embodiments, the subject ADCs may comprise nanobodies for targeted delivery of conjugated drug to targeted cancer cells. Nanobodies of use are disclosed, for example, in U.S. Pat. Nos. 7,807,162; 7,939,277; 8,188,223; 8,217,140; 8,372,398; 8,557,965; 8,623,361 and 8,629,244, the Examples section of each incorporated herein by reference.)

Antibody Fragments

Antibody fragments are antigen binding portions of an antibody, such as F(ab')$_2$, Fab', F(ab)$_2$, Fab, Fv, sFv, scFv and the like. Antibody fragments which recognize specific epitopes can be generated by known techniques. F(ab')$_2$ fragments, for example, can be produced by pepsin digestion of the antibody molecule. These and other methods are described, for example, by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9: 132-137 (1991).

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007).

An antibody fragment can also be prepared by proteolytic hydrolysis of a full-length antibody or by expression in *E. coli* or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 kD fragment denoted F(6)$_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

General Techniques for Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci., USA,* 86: 3833 (1989)). Based on the V gene sequences, a humanized MAb can then be designed and constructed as described by Leung et al. (*Mol. Immunol.,* 32: 1413 (1995)).

cDNA can be prepared from any known hybridoma line or transfected cell line producing a murine MAb by general molecular cloning techniques (Sambrook et al., Molecular Cloning, A laboratory manual, $2^{nd}$ Ed (1989)). The Vκ sequence for the MAb may be amplified using the primers VK1BACK and VK1FOR (Orlandi et al., 1989) or the extended primer set described by Leung et al. (*BioTechniques,* 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.,* 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the $V_K$ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human MAb. Alternatively, the $V_K$ and $V_H$ expression cassettes can be excised and subcloned into a single expression vector, such as pdHL2, as described by Gillies et al. (*J. Immunol. Methods* 125:191 (1989) and also shown in Losman et al., *Cancer,* 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Bispecific and Multispecific Antibodies

In certain embodiments the ADC and one or more other therapeutic antibodies may be administered as separate antibodies, either sequentially or concurrently. In alternative embodiments, antibodies or antibody fragments may be administered as a single bispecific or multispecific antibody. Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv), as discussed above. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "DOCK-AND-LOCK™" (DNL™), discussed in more detail below, has been utilized to produce combinations of virtually any desired antibodies, antibody fragments and other effector molecules. Any of the techniques known in the art for making bispecific or multispecific antibodies may be utilized in the practice of the presently claimed methods.

DOCK-AND-LOCK™ (DNL™)

Bispecific or multispecific antibodies or other constructs may be produced using the DOCK-AND-LOCK™ technology (see, e.g., U.S. Pat. Nos. 7,550,143; 7,521,056; 7,534,866; 7,527,787 and 7,666,400, the Examples section of each incorporated herein by reference). Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell Biol. 2004; 5:959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has $\alpha$ and $\beta$ isoforms (Scott, Pharmacol. Ther. 1991; 50:123). Thus, the four isoforms of PKA regulatory subunits are RI$\alpha$, RI$\beta$, RII$\alpha$ and RII$\beta$. The R subunits have been isolated only as stable dimers and the dimerization domain has been shown to consist of the first 44 amino-terminal residues of RII$\alpha$ (Newlon et al., Nat. Struct. Biol. 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RII$\alpha$, the AD binds to a hydrophobic surface formed by the 23 amino-terminal residues (Colledge and Scott, Trends Cell Biol. 1999; 6:216). Thus, the dimerization domain and AKAP binding domain of human RII$\alpha$ are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL™ constructs of different stoichiometry may be produced and used (see, e.g., U.S. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL™ constructs, different AD or DDD sequences may be utilized. Exemplary DDD and AD sequences are provided below.

```
DDD1
                                        (SEQ ID NO: 9)
SHIQIPPGLTELLQGYTVEVLRQQPPDLVEFAVEYFTRLREARA

DDD2
                                        (SEQ ID NO: 10)
CGHIQIPPGLTELLQGYTVEVLRQQPPDLVEFAVEYFTRLREARA

AD1
                                        (SEQ ID NO: 11)
QIEYLAKQIVDNAIQQA

AD2
                                        (SEQ ID NO: 12)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                        (SEQ ID NO: 13)
SLRECELYVQKHNIQALLKDSIVQLCTARPERPMAFLREYFERLEKEEAK

DDD3C
                                        (SEQ ID NO: 14)
MSCGGSLRECELYVQKHNIQALLKDSIVQLCTARPERPMAFLREYFERLE
KEEAK

AD3
                                        (SEQ ID NO: 15)
CGFEELAWKIAKMIWSDVFQQGC
```

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                        (SEQ ID NO: 16)
SLRECELYVQKHNIQALLKDVSIVQLCTARPERPMAFLREYFEKLEKEEAK

PKA RIβ
                                        (SEQ ID NO: 17)
SLKGCELYVQLHGIQQVLKDCIVHLCISKPERPMKFLREHFEKLEKEENRQ
ILA

PKA RIIα
                                        (SEQ ID NO: 18)
SHIQIPPGLTELLQGYTVEVGQQPPDLVDFAVEYFTRLREARRQ

PKA RIIβ
                                        (SEQ ID NO: 19)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:9 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                        (SEQ ID NO: 9)
    SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:9 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:20 to SEQ ID NO:39 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 2

Conservative Amino Acid Substitutions in DDD1 (SEQ ID NO: 9).
Consensus sequence disclosed as SEQ ID NO: 94.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K |   | N |   |   |   |   | A |   | S | D |   |   | N | A |   | S |   | D |   | K |
|   | R |   |   |   |   |   |   |   |   |   |   |   |   |   |   |   |   |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E |   |   | D |   | L |   | D |   |   |   | S | K |   | K | D | L | K | L |
|   |   |   |   |   |   |   |   |   | I |   |   |   |   |   |   |   |   |   |   | I |   | I |
|   |   |   |   |   |   |   |   |   | V |   |   |   |   |   |   |   |   |   |   | V |   | V |

```
THIQIPPGLTELLQGYTVEVLRQQPPDLVEFAVEYFTRLREARA
(SEQ ID NO: 20)
SKIQIPPGLTELLQGYTVEVLRQQPPDLVEFAVEYFTRLREARA
(SEQ ID NO: 21)
SRIQIPPGLTELLQGYTVEVLRQQPPDLVEFAVEYFTRLREARA
(SEQ ID NO: 22)
SHINIPPGLTELLQGYTVEVLRQQPPDLVEFAVEYFTRLREARA
(SEQ ID NO: 23)
SHIQIPPALTELLQGYTVEVLRQQPPDLVEFAVEYFTRLREARA
(SEQ ID NO: 24)
SHIQIPPGLSELLQGYTVEVLRQQPPDLVEFAVEYFTRLREARA
(SEQ ID NO: 25)
SHIQIPPGLTDLLQGYTVEVLRQQPPDLVEFAVEYFTRLREARA
(SEQ ID NO: 26)
SHIQIPPGLTELLNGYTVEVLRQQPPDLVEFAVEYFTRLREARA
(SEQ ID NO: 27)
SHIQIPPGLTELLQAYTVEVLRQQPPDLVEFAVEYFTRLREARA
(SEQ ID NO: 28)
SHIQIPPGLTELLQGYSVEVLRQQPPDLVEFAVEYFTRLREARA
(SEQ ID NO: 29)
SHIQIPPGLTELLQGYTVDVLRQQPPDLVEFAVEYFTRLREARA
(SEQ ID NO: 30)
SHIQIPPGLTELLQGYTVEVLKQQPPDLVEFAVEYFTRLREARA
(SEQ ID NO: 31)
SHIQIPPGLTELLQGYTVEVLRNQPPDLVEFAVEYFTRLREARA
(SEQ ID NO: 32)
SHIQIPPGLTELLQGYTVEVLRQNPPDLVEFAVEYFTRLREARA
(SEQ ID NO: 33)
SHIQIPPGLTELLQGYTVEVLRQQPELVEFAVEYFTRLREARA
(SEQ ID NO: 34)
SHIQIPPGLTELLQGYTVEVLRQQPPDLVDFAVEYFTRLREARA
(SEQ ID NO: 35)
SHIQIPPGLTELLQGYTVEVLRQQPPDLVEFLVEYFTRLREARA
(SEQ ID NO: 36)
SHIQIPPGLTELLQGYTVEVLRQQPPDLVEFIVEYFTRLREARA
(SEQ ID NO: 37)
SHIQIPPGLTELLQGYTVEVLRQQPPDLVEFVVEYFTRLREARA
(SEQ ID NO: 38)
SHIQIPPGLTELLQGYTVEVLRQQPPDLVEFAVDYFTRLREARA
(SEQ ID NO: 39)
```

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:11), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:11 below. The skilled artisan will realize that in designing sequence variants of the AD sequence, one would desirably avoid changing any of the underlined residues, while conservative amino acid substitutions might be made for residues that are less critical for DDD binding. Table 3 shows potential conservative amino acid substitutions in the sequence of AKAP-IS (AD1, SEQ ID NO:19), similar to that shown for DDD1 (SEQ ID NO:16) in Table 2 above.

A limited number of such potential alternative AD moiety sequences are shown in SEQ ID NO:40 to SEQ ID NO:57 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

AKAP-IS
(SEQ ID NO: 11)
QIEYLAKQIVDNAIQQA

TABLE 3

Conservative Amino Acid Substitutions in AD1 (SEQ ID NO: 11). Consensus sequence disclosed as SEQ ID NO: 95.

| Q | I | E | Y | L | A | K | Q | I | V | D | N | A | I | Q | Q | A |
|---|---|---|---|---|---|---|---|---|---|---|---|---|---|---|---|---|
| N | L<br>V | D | F<br>T<br>S | I<br>V | | R | N | | | E | Q | | | N | N | L<br>I<br>V |

NIEYLAKQIVDNAIQQA (SEQ ID NO: 40)
QLEYLAKQIVDNAIQQA (SEQ ID NO: 41)
QVEYLAKQIVDNAIQQA (SEQ ID NO: 42)
QIDYLAKQIVDNAIQQA (SEQ ID NO: 43)
QIEFLAKQIVDNAIQQA (SEQ ID NO: 44)
QIETLAKQIVDNAIQQA (SEQ ID NO: 45)
QIESLAKQIVDNAIQQA (SEQ ID NO: 46)
QIEYIAKQIVDNAIQQA (SEQ ID NO: 47)
QIEYVAKQIVDNAIQQA (SEQ ID NO: 48)
QIEYLARQIVDNAIQQA (SEQ ID NO: 49)
QIEYLAKNIVDNAIQQA (SEQ ID NO: 50)
QIEYLAKQIVENAIQQA (SEQ ID NO: 51)
QIEYLAKQIVDQAIQQA (SEQ ID NO: 52)
QIEYLAKQIVDNAINQA (SEQ ID NO: 53)
QIEYLAKQIVDNAIQNA (SEQ ID NO: 54)
QIEYLAKQIVDNAIQQL (SEQ ID NO: 55)
QIEYLAKQIVDNAIQQI (SEQ ID NO: 56)
QIEYLAKQIVDNAIQQV (SEQ ID NO: 57)

Gold et al. (2006, Mol Cell 24:383-95) utilized crystallography and peptide screening to develop a SuperAKAP-IS sequence (SEQ ID NO:58), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:59-61. Substitutions relative to the AKAP-IS sequence are underlined. It is anticipated that, as with the AD2 sequence shown in SEQ ID NO:12, the AD moiety may also include the additional N-terminal residues cysteine and glycine and C-terminal residues glycine and cysteine.

SuperAKAP-IS (SEQ ID NO: 58)
QIEYVAKQIVDYAIHQA

Alternative AKAP sequences (SEQ ID NO: 59)
QIEYKAKQIVDHAIHQA (SEQ ID NO: 60)
QIEYHAKQIVDHAIHQA (SEQ ID NO: 61)
QIEYVAKQIVDHAIHQA FIG. 2 of Gold et al. disclosed additional DDD-binding sequences from a variety of AKAP proteins, shown below.

RII-Specific AKAPs
AKAP-KL
(SEQ ID NO: 62)
PLEYQAGLLVQNAIQQAI

AKAP79
(SEQ ID NO: 63)
LLIETASSLVKNAIQLSI

AKAP-Lbc
(SEQ ID NO: 64)
LIEEAASRIVDAVIEQVK

RI-Specific AKAPs
AKAPce
(SEQ ID NO: 65)
ALYQFADRFSELVISEAL

RIAD
(SEQ ID NO: 66)
LEQVANQLADQIIKEAT

PV38
(SEQ ID NO: 67)
FEELAWKIAKMIWSDVF

Dual-Specificity AKAPs
AKAP7
(SEQ ID NO: 68)
ELVRLSKRLVENAVLKAV

MAP2D
(SEQ ID NO: 69)
TAEEVSARIVQVVTAEAV

DAKAP1
(SEQ ID NO: 70)
QIKQAAFQLISQVILEAT

DAKAP2
(SEQ ID NO: 71)
LAWKIAKMIVSDVMQQ

Stokka et al. (2006, Biochem J 400:493-99) also developed peptide competitors of AKAP binding to PKA, shown in SEQ ID NO:72-74. The peptide antagonists were designated as Ht31 (SEQ ID NO:72), RIAD (SEQ ID NO:73) and PV-38 (SEQ ID NO:74). The Ht-31 peptide exhibited a geater affinity for the RH isoform of PKA, while the RIAD and PV-38 showed higher affinity for RI.

Ht31
(SEQ ID NO: 72)
DLIEEAASRIVDAVIEQVKAAGAY

RIAD
(SEQ ID NO: 73)
LEQYANQLADQIIKEATE

PV-38
(SEQ ID NO: 74)
FEELAWKIAKMIWSDVFQQC

Hundsrucker et al. (2006, Biochem J 396:297-306) developed still other peptide competitors for AKAP binding to PKA, with a binding constant as low as 0.4 nM to the DDD of the MI form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

| AKAP Peptide sequences | |
|---|---|
| | Peptide Sequence |
| AKAPIS | QIEYLAKQIVDNAIQQA (SEQ ID NO: 11) |
| AKAPIS-P | QIEYLAKQIPDNAIQQA (SEQ ID NO: 75) |
| Ht31 | KGADLIEEAASRIVDAVIEQVKAAG (SEQ ID NO: 76) |
| Ht31-P | KGADLIEEAASRIPDAPIEQVKAAG (SEQ ID NO: 77) |
| AKAP7δ-wt-pep | PEDAELVRLSKRLVENAVLKAVQQY (SEQ ID NO: 78) |
| AKAP7δ-L304T-pep | PEDAELVRTSKRLVENAVLKAVQQY (SEQ ID NO: 79) |
| AKAP7δ-L308D-pep | PEDAELVRLSKRDVENAVLKAVQQY (SEQ ID NO: 80) |
| AKAP7δ-P-pep | PEDAELVRLSKRLPENAVLKAVQQY (SEQ ID NO: 81) |
| AKAP7δ-PP-pep | PEDAELVRLSKRLPENAPLKAVQQY (SEQ ID NO: 82) |
| AKAP7δ-L314E-pep | PEDAELVRLSKRLVENAVEKAVQQY (SEQ ID NO: 83) |
| AKAP1-pep | EEGLDRNEEIKRAAFQIISQVISEA (SEQ ID NO: 84) |
| AKAP2-pep | LVDDPLEYQAGLLVQNAIQQAIAEQ (SEQ ID NO: 85) |
| AKAP5-pep | QYETLLIETASSLVKNAIQLSIEQL (SEQ ID NO: 86) |
| AKAP9-pep | LEKQYQEQLEEEVAKVIVSMSIAFA (SEQ ID NO: 87) |
| AKAP10-pep | NTDEAQEELAWKIAKMIVSDIMQQA (SEQ ID NO: 88) |
| AKAP11-pep | VNLDKKAVLAEKIVAEAIEKAEREL (SEQ ID NO: 89) |
| AKAP12-pep | NGILELETKSSKLVQNIIQTAVDQF (SEQ ID NO: 90) |
| AKAP14-pep | TQDKNYEDELTQVALALVEDVINYA (SEQ ID NO: 91) |
| Rab32-pep | ETSAKDNINIEEAARFLVEKILVNH (SEQ ID NO: 92) |

Residues that were highly conserved among the AD domains of different AKAP proteins are indicated below by underlining with reference to the AKAP IS sequence (SEQ ID NO:11). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
(SEQ ID NO: 11)
QIEYLAKQIVDNAIQQA

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PICA RIIα DDD sequence of SEQ ID NO:9. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 9)
SH*IQI*PPGLT*ELLQGY*TV*EVLRQQP*PDLVEFAVE*YF*TR*LR*EARA

A modified set of conservative amino acid substitutions for the DDD1 (SEQ ID NO:9) sequence, based on the data of Carr et al. (2001) is shown in Table 5. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 2 and Table 3.

improved pharmacokinetics, stability and anti-lymphoma activity in vivo (Rossi et al., 2013, Bioconjug Chem 24:63-71).

$C_k$-conjugated DNL™ constructs may be prepared as disclosed in Provisional U.S. Patent Application Ser. Nos. 61/654,310, 61/662,086, 61/673,553, and 61/682,531. Briefly, $C_k$-AD2-IgG, was generated by recombinant engineering, whereby the AD2 peptide was fused to the C-terminal end of the kappa light chain. Because the natural C-terminus of $C_K$ is a cysteine residue, which forms a disulfide bridge to $C_H1$, a 16-amino acid residue "hinge" linker was used to space the AD2 from the $C_K$-$V_H1$ disulfide bridge. The mammalian expression vectors for $C_k$-AD2-IgG-veltuzumab and $C_k$-AD2-IgG-epratuzumab were constructed using the pdHL2 vector, which was used previously for expression of the homologous $C_H3$-AD2-IgG modules. A 2208-bp nucleotide sequence was synthesized comprising the pdHL2 vector sequence ranging from the Bam HI restriction site within the $V_K/C_K$ intron to the Xho I restriction site 3' of the $C_k$ intron, with the insertion of the coding sequence for the hinge linker (EFPKPSTPPGSSGGAP, SEQ ID NO:93) and AD2, in frame at the 3' end of the coding sequence for $C_K$. This synthetic sequence was inserted into the IgG-pdHL2 expression vectors for veltuzumab and epratuzumab via Bam HI and Xho I restriction sites. Generation of production clones with SpESFX-10 were performed as described for the $C_H3$-AD2-IgG modules. $C_k$-AD2-IgG-veltuzumab and $C_k$-AD2-IgG-epratuzumab were produced by stably-transfected production clones in batch roller bottle culture, and purified from the supernatant

TABLE 5

Conservative Amino Acid Substitutions in DDD1 (SEQ ID NO: 9).
Consensus sequence disclosed as SEQ ID NO: 96.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   | N |   |   |   |   |   |   | S |   |   |   |   |   |   |   | I |   |   |   |   |
|   |   |   |   |   |   |   |   |   |   |   |   |   |   |   |   |   | L |   |   |   |   |
|   |   |   |   |   |   |   |   |   |   |   |   |   |   |   |   |   | A |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N |   |   |   |   |   |   |   |   |   | I |   |   |   |   |   |   |   |   |   |   |   |
|   |   |   |   |   |   |   |   |   |   | L |   |   |   |   |   |   |   |   |   |   |   |
|   |   |   |   |   |   |   |   |   |   | A |   |   |   |   |   |   |   |   |   |   |   |

The skilled artisan will realize that these and other amino acid substitutions in the DDD or AD amino acid sequences may be utilized to produce alternative species within the genus of AD or DDD moieties, using techniques that are standard in the field and only routine experimentation.

Alternative DNL™ Structures

In certain alternative embodiments, DNL™ constructs may be formed using alternatively constructed antibodies or antibody fragments, in which an AD moiety may be attached at the C-terminal end of the kappa light chain ($C_k$), instead of the C-terminal end of the Fc on the heavy chain. The alternatively formed DNL™ constructs may be prepared as disclosed in Provisional U.S. Patent Application Ser. Nos. 61/654,310, filed Jun. 1, 2012, 61/662,086, filed Jun. 20, 2012, 61/673,553, filed Jul. 19, 2012, and 61/682,531, filed Aug. 13, 2012, the entire text of each incorporated herein by reference. The light chain conjugated DNL™ constructs exhibit enhanced Fc-effector function activity in vitro and fluid in a single step using MabSelect (GE Healthcare) Protein A affinity chromatography.

Following the same DNL™ process described previously for 22-(20)-(20) (Rossi et al., 2009, Blood 113:6161-71), $C_k$-AD2-IgG-epratuzumab was conjugated with $C_H1$-DDD2-Fab-veltuzumab, a Fab-based module derived from veltuzumab, to generate the bsHexAb 22*-(20)-(20), where the 22* indicates the $C_k$-AD2 module of epratuzumab and each (20) symbolizes a stabilized dimer of veltuzumab Fab. The properties of 22*-(20)-(20) were compared with those of 22-(20)-(20), the homologous Fc-bsHexAb comprising $C_H3$-AD2-IgG-epratuzumab, which has similar composition and molecular size, but a different architecture.

Following the same DNL™ process described previously for 20-2b (Rossi et al., 2009, *Blood* 114:3864-71), $C_k$-AD2-IgG-veltuzumab, was conjugated with IFNα2b-DDD2, a module of IFNα2b with a DDD2 peptide fused at its C-terminal end, to generate 20*-2b, which comprises veltuzumab with a dimeric IFNα2b fused to each light chain.

The properties of 20*-2b were compared with those of 20-2b, which is the homologous Fc-IgG-IFNα.

Each of the bsHexAbs and IgG-IFNα were isolated from the DNL™ reaction mixture by MabSelect affinity chromatography. The two $C_k$-derived prototypes, an anti-CD22/CD20 bispecific hexavalent antibody, comprising epratuzumab (anti-CD22) and four Fabs of veltuzumab (anti-CD20), and a CD20-targeting immunocytokine, comprising veltuzumab and four molecules of interferon-α2b, displayed enhanced Fc-effector functions in vitro, as well as improved pharmacokinetics, stability and anti-lymphoma activity in vivo, compared to their Fc-derived counterparts.

Amino Acid Substitutions

In alternative embodiments, the disclosed methods and compositions may involve production and use of proteins or peptides with one or more substituted amino acid residues. For example, the DDD and/or AD sequences used to make DNL™ constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Pre-Targeting

Bispecific or multispecific antibodies may be of use in pretargeting techniques. In this case, one or more therapeutic agent may be conjugated to a targetable construct that comprises one or more haptens. The hapten is recognized by at least one arm of a bispecific or multispecific antibody that also binds to a tumor-associated antigen or other disease-associated antigen. In this case, the therapeutic agent binds indirectly to the antibodies, via the binding of the targetable construct. This process is referred to as pretargeting.

Pre-targeting is a multistep process originally developed to resolve the slow blood clearance of directly targeting antibodies, which contributes to undesirable toxicity to normal tissues such as bone marrow. With pre-targeting, a therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med.

28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256, 395; Stickney et al., Cancer Res. 51:6650, 1991; Yuan et al., Cancer Res. 51:3119, 1991; U.S. Pat. Nos. 6,077,499; 7,011, 812; 7,300,644; 7,074,405; 6,962,702; 7,387,772; 7,052, 872; 7,138,103; 6,090,381; 6,472,511; 6,962,702; and 6,962, 702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues and one or more haptens for binding, e.g., to a bispecific antibody. Exemplary haptens may include In-DTPA (indium-diethylene triamine pentaacetic acid) or HSG (histamine succinyl glycine). The targetable construct may also comprise one or more chelating moieties, such as DOTA (1,4,7,10-tetraazacyclododecane1,4,7,10-tetraacetic acid), NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties. Chelating moieties may be used, for example, to bind to a therapeutic and or diagnostic radionuclide, paramagnetic ion or contrast agent.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Immunoconjugates

In certain embodiments, a cytotoxic drug or other therapeutic or diagnostic agent may be covalently attached to an antibody or antibody fragment to form an immunoconjugate. In some embodiments, a drug or other agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio) propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the ADC is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetylmannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or Vx domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

Other Therapeutic Agents

A wide variety of therapeutic reagents can be administered concurrently or sequentially with the subject ADCs. Alternatively, such agents may be conjugated to the antibodies of the invention, for example, drugs, toxins, oligonucleotides, immunomodulators, hormones, hormone antagonists, enzymes, enzyme inhibitors, radionuclides, angiogenesis inhibitors, etc. The therapeutic agents recited here are those agents that also are useful for administration separately with an ADC as described above. Therapeutic agents include, for example, cytotoxic drugs such as vinca alkaloids, anthracyclines such as doxorubicin, 2-PDox or pro-2-PDox, gemcitabine, epipodophyllotoxins, taxanes, antimetabolites, alkylating agents, antibiotics, SN-38, COX-2 inhibitors, antimitotics, anti-angiogenic and pro-apoptotic agents, particularly doxorubicin, methotrexate, taxol, CPT-11, camptothecans, proteosome inhibitors, mTOR inhibitors, HDAC inhibitors, tyrosine kinase inhibitors, and others. Other useful anti-cancer cytotoxic drugs for administering concurrently or sequentially, or for the preparation of ADCs include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins, hormones, and the like. Suitable cytotoxic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable cytotoxic agents, such as experimental drugs, are known to those of skill in the art. In a preferred embodiment, conjugates of camptothecins and related compounds, such as SN-38, may be conjugated to hRS7 or other anti-Trop-2 antibodies. In another preferred embodiment, gemcitabine is administered to the subject in conjunction with SN-38-hRS7 and/or $^{90}$Y-hPAM4.

A toxin can be of animal, plant or microbial origin. Toxins of use include ricin, abrin, ribonuclease (RNase), DNase I, Staphylococcal enterotoxin-A, pokeweed antiviral protein, onconase, gelonin, diphtheria toxin, Pseudomonas exotoxin, and Pseudomonas endotoxin. See, for example, Pastan et al., Cell 47:641 (1986), Goldenberg, C A—A Cancer Journal for Clinicians 44:43 (1994), Sharkey and Goldenberg, C A—A Cancer Journal for Clinicians 56:226 (2006). Additional toxins suitable for use are known to those of skill in the art and are disclosed in U.S. Pat. No. 6,077,499, the Examples section of which is incorporated herein by reference.

As used herein, the term "immunomodulator" includes a cytokine, a lymphokine, a monokine, a stem cell growth factor, a lymphotoxin, a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-α, TGF-β, insulin-like growth factor (ILGF), erythropoietin, thrombopoietin, tumor necrosis factor (TNF), TNF-α, TNF-β, a mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, interferon-λ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 and IL-25, LIF, kit-ligand, FLT-3, angiostatin, thrombospondin, endostatin, lymphotoxin, and the like.

Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{32}$P, $^{33}$P, $^{47}$Sc, $^{111}$Ag, $^{67}$Ga, $^{142}$Pr, $^{153}$Sm, $^{161}$Tb, $^{166}$D, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Fm-255 and Th-227. Decay energies of useful alpha-particle-emitting radionuclides are preferably 2,000-10,000 keV, more preferably 3,000-8,000 keV, and most preferably 4,000-7,000 keV.

For example, $^{90}$Y, which emits an energetic beta particle, can be coupled to an antibody, antibody fragment or fusion protein, using diethylenetriaminepentaacetic acid (DTPA), or more preferably using DOTA. Methods of conjugating $^{90}$Y to antibodies or targetable constructs are known in the art and any such known methods may be used. (See, e.g., U.S. Pat. No. 7,259,249, the Examples section of which is incorporated herein by reference. See also Linden et al., Clin Cancer Res. 11:5215-22, 2005; Sharkey et al., J Nucl Med. 46:620-33, 2005; Sharkey et al., J Nucl Med. 44:2000-18, 2003.)

Additional potential therapeutic radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

In another embodiment, a radiosensitizer can be used in combination with a naked or conjugated antibody or antibody fragment. For example, the radiosensitizer can be used in combination with a radiolabeled antibody or antibody fragment. The addition of the radiosensitizer can result in enhanced efficacy when compared to treatment with the radiolabeled antibody or antibody fragment alone. Radiosensitizers are described in D. M. Goldenberg (ed.), CANCER THERAPY WITH RADIOLABELED ANTIBODIES, CRC Press (1995). Other typical radionsensitizers of interest for use with this technology include gemcitabine, 5-fluorouracil, and cisplatin, and have been used in combination with external irradiation in the therapy of diverse cancers.

Antibodies or fragments thereof that have a boron addend-loaded carrier for thermal neutron activation therapy will normally be affected in similar ways. However, it will be advantageous to wait until non-targeted immuno conjugate clears before neutron irradiation is performed. Clearance can be accelerated using an anti-idiotypic antibody that binds to the anti-cancer antibody. See U.S. Pat. No. 4,624,846 for a description of this general principle. For example, boron addends such as carboranes, can be attached to antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody. After administration of the antibody conjugate, a boron addend is activated by thermal neutron irradiation and converted to radioactive atoms which decay by alpha-emission to produce highly toxic, short-range effects.

Formulation and Administration

Suitable routes of administration of ADCs include, without limitation, oral, parenteral, rectal, transmucosal, intestinal administration, intramedullary, intrathecal, direct intraventricular, intravenous, intravitreal, intracavitary, intraperitoneal, or intratumoral injections. The preferred routes of administration are parenteral, more preferably intravenous. Alternatively, one may administer the compound in a local rather than systemic manner, for example, via injection of the compound directly into a solid or hematological tumor.

ADCs can be formulated according to known methods to prepare pharmaceutically useful compositions, whereby the ADC is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

In a preferred embodiment, the ADC is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino)ethanesulfonic acid (MES); 3-(N-morpholino)propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The ADC can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the ADC. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an ADC from such a matrix depends upon the molecular weight of the ADC, the amount of ADC within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered ADC for humans will vary depending upon such factors as the patient's age, weight, height, sex, general medical condition and previous medical history. As discussed above, dosages of antibody-SN-38 conjugates may vary from 3 to 18, more preferably 4 to 16, more preferably 6 to 12, more preferably 8 to 10 mg/kg. The dosage may be repeated as needed, for example, once per week for 2-10 weeks, once per week for 8 weeks, or once per week for 4 weeks. It may also be given less frequently, such as every other week for several months, or monthly or quarterly for many months, as needed in a maintenance therapy. The dosage is preferably administered multiple times, once a week. A minimum dosage schedule of 4 weeks, more preferably 8 weeks, more preferably 16 weeks or longer may be used, with the dose frequency dependent on toxic side-effects and recovery therefrom, mostly related to hematological toxicities. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v)

three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 2, 4, 6, 8, 10, or 12 times or more.

Alternatively, an ADC may be administered as one dosage every 2 or 3 weeks, repeated for a total of at least 3 dosages. Or, twice per week for 4-6 weeks. The dosage may be administered once every other week or even less frequently, so the patient can recover from any drug-related toxicities. Alternatively, the dosage schedule may be decreased, namely every 2 or 3 weeks for 2-3 months. The dosing schedule can optionally be repeated at other intervals and dosage may be given through various parenteral routes, with appropriate adjustment of the dose and schedule.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. In preferred embodiments, the method of the invention is used to inhibit growth, progression, and/or metastasis of cancers, in particular those listed above.

Kits

Various embodiments may concern kits containing components suitable for treating cancer tissue in a patient. Exemplary kits may contain at least one ADC as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, an antibody or antigen binding fragment thereof may be provided in the form of a prefilled syringe or autoinjection pen containing a sterile, liquid formulation or lyophilized preparation of antibody (e.g., Kivitz et al., Clin. Ther. 2006, 28:1619-29).

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions for use of the kit.

EXAMPLES

The examples below are illustrative of embodiments of the current invention and are not limiting to the scope of the claims.

Example 1

Targeted Therapy of GI Cancers with IMMU-132 (Isactuzumab Govitecan), an Anti-Trop-2-SN-38 Antibody Drug Conjugate (ADC)

Trop-2 is a tumor-associated glycoprotein highly prevalent in many epithelial cancers. Its elevated expression has been linked to more aggressive disease and a poor prognosis. A humanized mAb binding to the extracellular domain of Trop-2 was conjugated to SN-38 (IMMU-132; average drug:mAb ratio=7.6), the active principle of CPT-11. After potent activity in human tumor xenografts, a Phase I/II trial was initiated in patients (pts) with diverse solid tumors, including GI cancers.

Methods: Patients with metastatic cancers were enrolled after failing standard therapy, starting at a dose of 8.0 mg/kg given on days 1 and 8 of a 3-week cycle. The MTD was determined to be 12 mg/kg; dose levels of 8 and 10 mg/kg were chosen for Phase II testing.

Results: Sixty patients with advanced GI cancers were enrolled in a Phase I/II trial. In 29 CRC patients (9 treated at 10 mg/kg, 20 at 8 mg/kg), 1 had a PR (partial response) and 14 had SD (stable disease) as the best response by RECIST, with a time to progression (TTP) of 50+wks for the PR (−65%) and a median of 21+ wks for the SD patients (5 continuing). Thirteen CRC patients had KRAS mutations, 7 showing SD with a median TTP of 19.1+ wks (range, 12.0-34.0; 3 continuing). Of 15 pancreatic cancer patients that were treated (5 at 8, 7 at 10, and 3 at 12 mg/kg), 7 had SD as best response for a median TTP of 15.0 wks. Among 11 patients with esophageal cancer (9 started at 8, 1 at 10, and 1 at 18 mg/kg), 8 had CT assessment, showing 1 PR with a TTP of 30+ wks, and 4 with SD of 17.4+, 21.9, 26.3, and 29.9 wks. Of 5 gastric cancer patients (2 at 8 and 3 at 10 mg/kg), only 3 have had CT assessment, all with SD (1 with 19% target lesion reduction and an ongoing TTP of 29+ wks).

Neutropenia was the principal dose-limiting toxicity, with fatigue, diarrhea, nausea, and vomiting as other commonly reported toxicities. However, the toxicity profile from 75 patients in the full trial showed only 17.3% and 2.7% Grade 3 and Grade 4 neutropenia, respectively, and just 6.7% Grade 3 diarrhea.

Conclusions: IMMU-132 showed a high therapeutic index in patients with diverse relapsed metastatic GI cancers. It has a moderately-toxic drug conjugated to an internalizing, cancer-selective mAb, which can be given repeatedly over many months once weekly×2 in a 21-day cycle.

Example 2

Anti-CEACAM5-SN-38 Antibody Drug Conjugate (IMMU-130) Activity in Metastatic Colorectal Cancer (mCRC)

IMMU-130 is a CEACAM5-targeted ADC, labetuzumab-SN-38, with the drug being the active form of the topoisomerase I inhibitor, CPT-11, and substituted at 7-8 moles/mole of IgG. This agent is in Phase I/II clinical trials in patients with relapsed mCRC.

Methods: Experiments were conducted in female athymic nude mice, 4 weeks or older, bearing s.c. LS174T human colon carcinoma xenografts of (~0.2 cm³ size), or 2 weeks after lung metastases were generated by i.v. injection of GW-39 human colon carcinoma cells. Untreated controls, including a non-targeting ADC, were included. Biodistribution was examined in the s.c model using single 12.5 mg/kg dose of the ADC or unconjugated labetuzumab, each spiked with $^{111}$In-labeled substrate. Tolerability studies were conducted in white New Zealand rabbits.

Results: In the metastatic model (n=8), fractionated dosing of 2 cycles of a 21-day cycle therapy, with a fixed total dose of 50 mg/kg of ADC, showed that twice-weekly×2 weeks and once weekly×2 weeks schedules doubled median survival vs. untreated mice, and was better than the once for 2 weeks schedule (P<0.0474; log-rank). Pre-dosing with as much as twice the dose of labetuzumab as the ADC dose, in the metastatic model (n=10), did not affect median survival (P>0.15). Therapy experiments in the s.c. model revealed that the linker in IMMU-130, liberating 50% of drug in ~20 h, was superior to the conjugate with an ultrastable linker (n=5), that the ADC was better than an MTD of 5FU/leucovorin chemotherapy (n=10; P<0.0001), and that the ADC could be combined with bevacizumab for improved efficacy (n=8-10; P<0.031). Significantly better efficacy for the specific ADC vs. nonspecific ADC was observed. Pharmacokinetics in mice indicated ~25% longer half-life for MAb vs. ADC, but with minimal impact on tumor uptake. A tolerability study in rabbits showed the NOAEL to be the human equivalent dose of 40-60 mg/kg, given as two doses.

Conclusions: Preclinical data showed an excellent therapeutic window for this ADC, which appears to be translated into the clinical experience thus far. The potential for combination therapy is also indicated.

Example 3

Production and Use of anti-Trop-2-SN-38 Antibody-Drug Conjugate

The humanized RS7 (hRS7) anti-Trop-2 antibody was produced as described in U.S. Pat. No. 7,238,785, the Figures and Examples section of which are incorporated herein by reference. SN-38 attached to a CL2A linker was produced and conjugated to hRS7 (anti-Trop-2), hPAM4 (anti-MUC5ac), hA20 (anti-CD20) or hMN-14 (anti-CEACAM5) antibodies according to U.S. Pat. No. 7,999,083 (Example 10 and 12 of which are incorporated herein by reference). The conjugation protocol resulted in a ratio of about 6 SN-38 molecules attached per antibody molecule.

Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. FIG. 1 shows a Capan 1 pancreatic tumor model, wherein specific CL2A-SN-38 conjugates of hRS7 (anti-Trop-2), hPAM4 (anti-MUC-5ac), and hMN-14 (anti-CEACAM5) antibodies showed better efficacies than control hA20-CL2A-SN-38 conjugate (anti-CD20) and untreated control. Similarly in a BXPC3 model of human pancreatic cancer, the specific hRS7-CL2A-SN showed better therapeutic efficacy than control treatments (FIG. 2).

Example 4

Efficacy of Anti-Trop-2 Antibody Conjugated to a Prodrug Form of 2-Pyrrolinodoxorubicin (2-PDox)

A prodrug form of 2-PDox (referred to as pro-2-PDox) was prepared and conjugated to antibodies as disclosed in U.S. patent application Ser. No. 14/175,089 (Example 1 of which is incorporated herein by reference). The structures of doxorubicin, 2-PDox, pro-2-PDox and a maleimide activated form of pro-2-PDox that is suitable for conjugation to sulthydryl groups on antibodies or other proteins are shown in FIG. 3. Unless otherwise stated below, the number of drug moieties per antibody molecule was in the range of about 6.5 to about 7.5.

In vitro cell-binding studies—Retention of antibody binding was confirmed by cell binding assays comparing binding of the conjugated to the unconjugated antibody (Chari, 2008, Acc Chem Res 41:98-107). The potency of the conjugate was tested in a 4-day MTS assay using appropriate target cells. The anti-Trop-2 ADC (hRS7-pro-2-PDox) exhibited $IC_{50}$ values of 0.35-1.09 nM in gastric (NCI-N87), pancreatic (Capan-1), and breast (MDA-MB-468) human cancer cell lines, with free drug exhibiting 0.02-0.07 nM potency in the same cell lines. In additional studies, hRS7-pro-2-PDox was observed to be cytotoxic to MDA-MB-468, AG S, NCI-N87 and Capan-1 solid tumor cell lines (not shown).

No significant difference in binding of the antibody moiety to NCI-N87 gastric carcinoma cells was observed between unconjugated hRS7 and pro-2-PDox-hRS7 conjugated to 6 molecules of pro-2-PDox per antibody (not shown). It is concluded that conjugation of pro-2-PDox to antibodies does not affect antibody-antigen binding activity.

Serum stability—Serum stability of anti-Trop-2 ADC (hRS7-pro-2-PDox) was determined by incubation in human serum at a concentration of 0.2 mg/mL at 37° C. The incubate was analyzed by HPLC using butyl hydrophobic interaction chromatography (HIC). The analysis showed that there was no release of free drug from the conjugate, suggesting high serum stability of the conjugate. When the same experiment was repeated with hRS7-doxorubicin conjugate, containing the same cleavable linker as hRS7-pro-2-PDox, and where the free drug was independently verified to be released with a half-life of 96 h, clear formation of a peak corresponding to free doxorubicin was seen on HIC HPLC.

Surprisingly, it was determined that the pro-2-PDox conjugate was held tightly to the antibody because it cross-linked the peptide chains of the antibody together. The cross-linking stabilizes the attachment of the drug to the antibody so that the drug is only released intracellularly after the antibody is metabolized. The cross-linking assists in minimizing toxicity, for example cardiotoxicity, that would result from release of free drug in circulation. Previous use of 2-PDox peptide conjugates failed because the drug cross-linked the peptide to other proteins or peptides in vivo. With the present anti-Trop-2 ADC, the pro-2-PDox is attached to interchain disulfide thiol groups while in the prodrug form. The prodrug protection is rapidly removed in vivo soon after injection and the resulting 2-PDox portion of the conjugate cross-links the peptide chains of the antibody, forming intramolecular cross-linking within the antibody molecule. This both stabilizes the ADC and prevents cross-linking to other molecules in circulation.

In vivo preclinical studies—Tumor size was determined by caliper measurements of length (L) and width (W) with tumor volume calculated as $(L \times W^2)/2$. Tumors were measured and mice weighed twice a week. Mice were euthanized if their tumors reached >1 cm³ in size, lost greater than 15% of their starting body weight, or otherwise became moribund. Statistical analysis for the tumor growth data was based on area under the curve (AUC) and survival time. Profiles of individual tumor growth were obtained through linear curve modeling. An f-test was employed to determine equality of variance between groups prior to statistical analysis of growth curves. A two-tailed t-test was used to assess statistical significance between all the various treatment groups and non-specific controls. For the saline control analysis a one-tailed t-test was used to assess significance. Survival studies were analyzed using Kaplan-Meier plots (log-rank analysis), using the Prism GraphPad Software (v4.03) software package (Advanced Graphics Software, Inc.; Encinitas, Calif.). All doses in preclinical experiments are expressed in antibody amounts. In terms of drug, 100 µg of antibody (5 mg/kg) in a 20-g mouse, for example, carries 1.4 µg-2.8 µg (0.14-0.17 mg/kg) of pro-2-PDox equivalent dose when using an ADC with 3-6 drugs/IgG.

Figure 4:
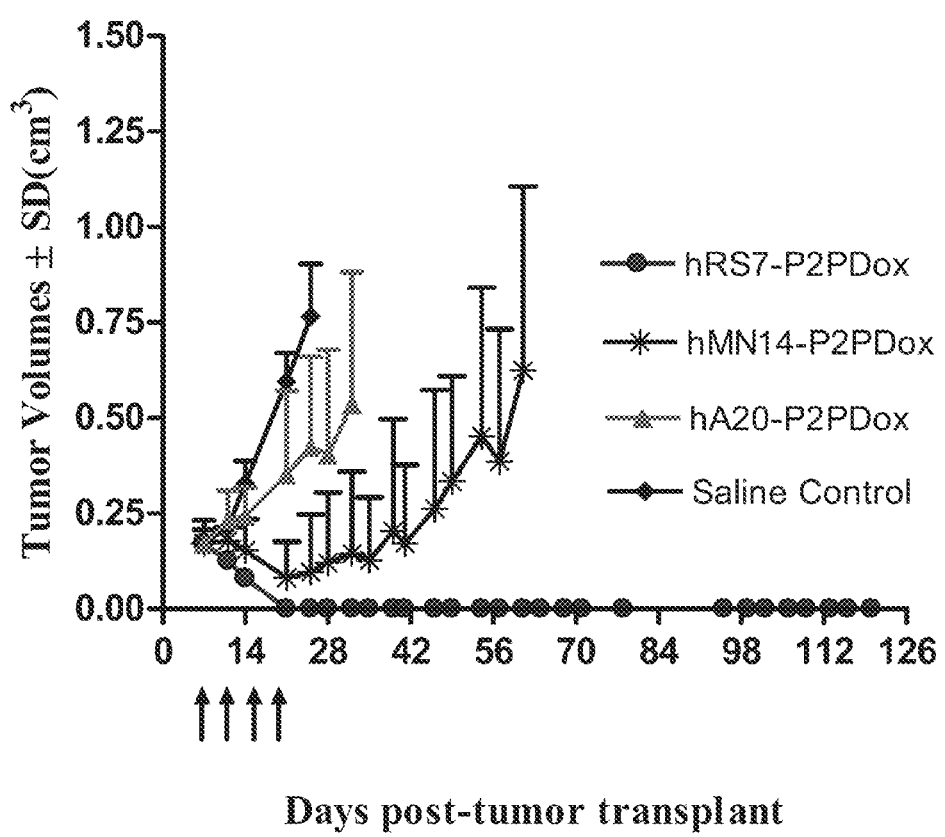
FIG. 4. Therapy in nude mice bearing s.c. human tumor xenografts using 2.25 mg/kg protein dose (0.064 mg/kg of drug dose) of MAb-pro-2-PDox conjugates twice weekly×2 weeks in nude mice with Capan-1 human pancreatic adenocarcinoma xenografts (n=5).

A single i.v. dose of ≥300 µg [~10 µg of pro-2-PDox] of the anti-Trop-2 ADC was lethal, but 4 doses of 45 µg given in 2 weeks were tolerated by all animals. Using this dosing regimen, we examined the therapeutic effect of anti-Trop-2 hRS7-pro-2-PDox in 2 human tumor xenograft models, Capan-1 (pancreatic cancer) and NCI-N87 (gastric cancer). Therapy began 7 days after tumor transplantation in nude mice. In the established, 7-day-old, Capan-1 model, 100% of established tumors quickly regressed, with no evidence of re-growth (FIG. 4). This result was reproduced in a repeat experiment (not shown). The anti-Trop-2 conjugate of pro-2-PDox was much more effective than the same drug conjugated to an antibody (hMN-14) against CEACAM5, which is also expressed in pancreatic cancer, or an antibody against CD20 (hA20), which is not. All treatments were superior to the saline control.

Figure 5A:
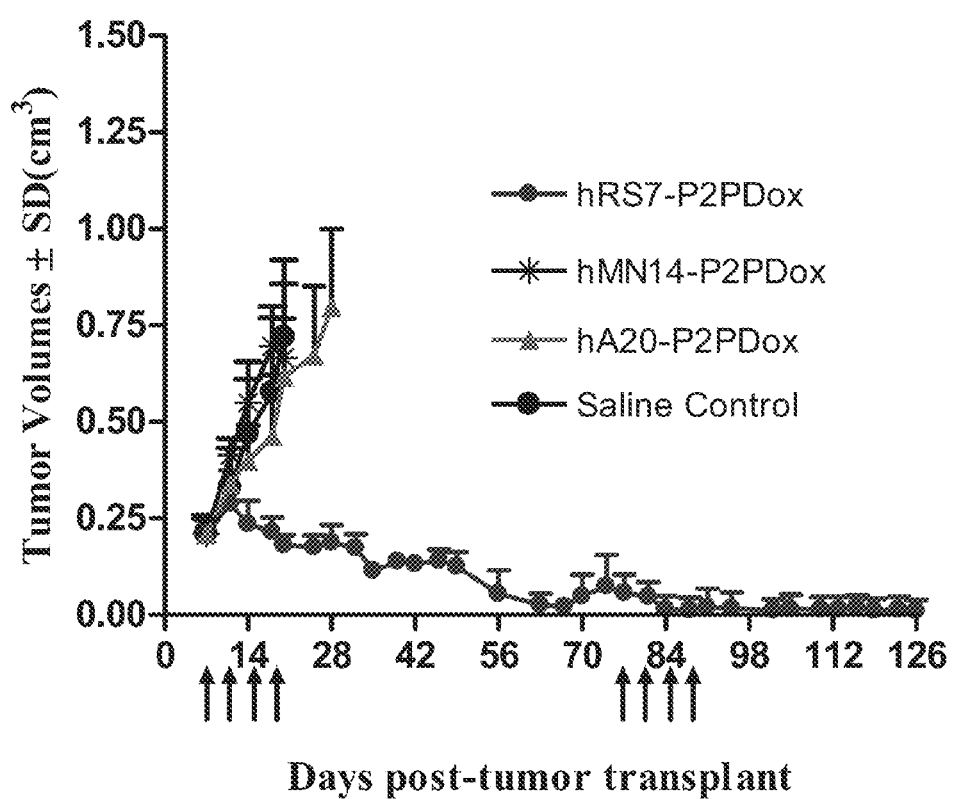
FIG. 5A. Therapy in nude mice bearing s.c. human tumor xenografts using 2.25 mg/kg protein dose (0.064 mg/kg of drug dose) of MAb-pro-2-PDox conjugates twice weekly×2 weeks in nude mice (n=7) with NCI-N87 human gastric carcinoma xenografts.
Figure 5B:
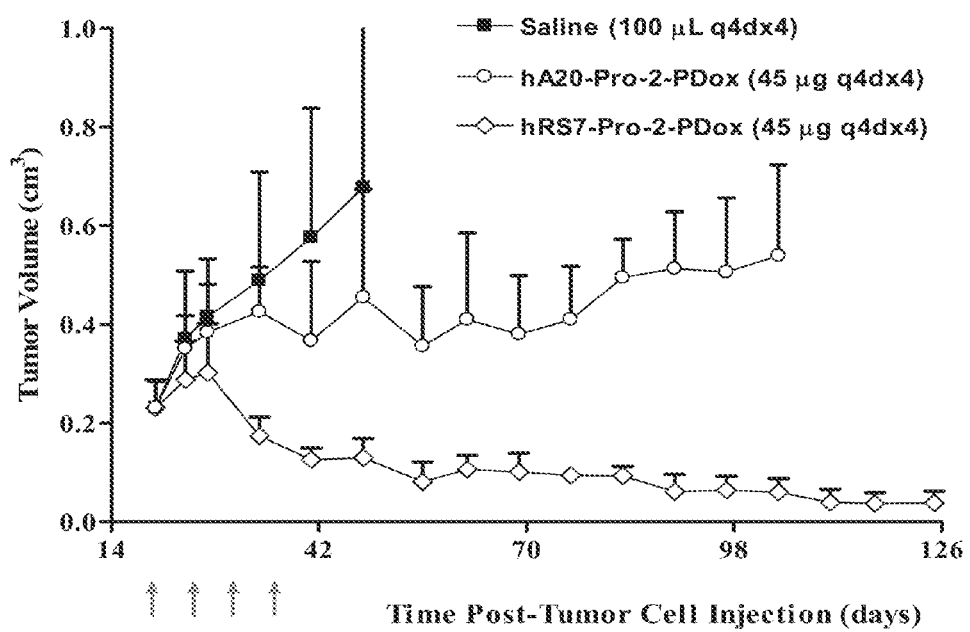
FIG. 5B. Therapy in nude mice bearing s.c. human tumor xenografts using 2.25 mg/kg protein dose (0.064 mg/kg of drug dose) of MAb-pro-2-PDox conjugates twice weekly×2 weeks in nude mice (n=7) with MDA-MB-468 human breast carcinoma xenografts.
Figure 5C:
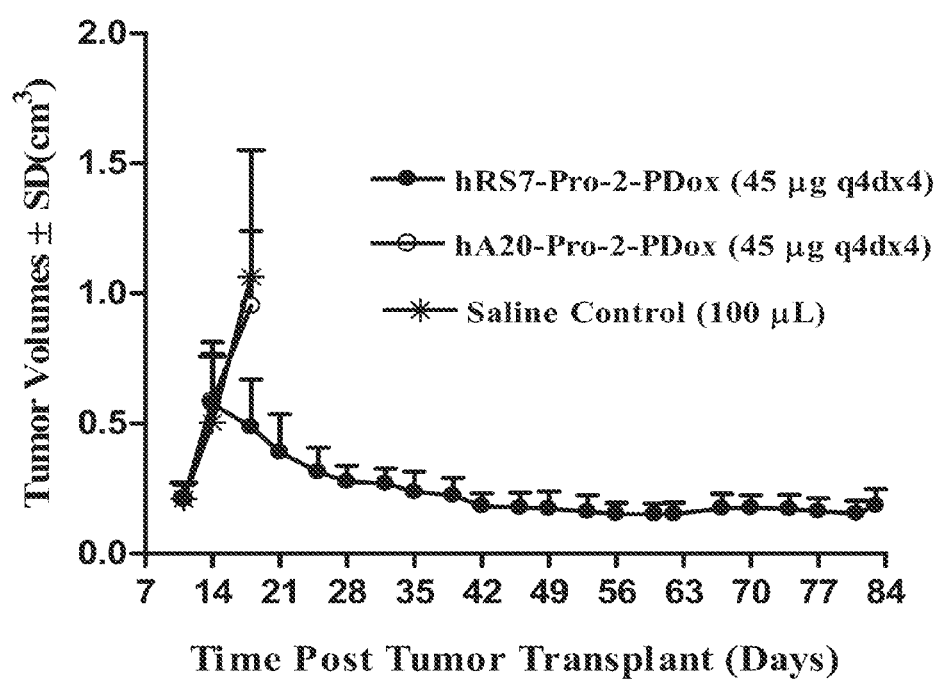
FIG. 5C. Therapy in nude mice bearing s.c. human tumor xenografts using 2.25 mg/kg protein dose (0.064 mg/kg of drug dose) of MAb-pro-2-PDox conjugates twice weekly×2 weeks in nude mice (n=7) with BxPC3 human pancreatic carcinoma xenografts.

Similar results were observed in the established NCI-N87 model (FIG. 5A), where a $2^{nd}$ course of therapy, administered after day 70, was safely tolerated and led to further regressions of residual tumor (FIG. 5A). The internalizing hRS7-SN-38 conjugate, targeting Trop-2, provided better therapeutic responses than a conjugate of a poorly internalizing anti-CEACAM5 antibody, hMN-14 (FIG. 4, FIG. 5). A non-targeted anti-CD20 ADC, hA20-pro-2-PDox, was ineffective, indicating selective therapeutic efficacy (FIG. 4, FIG. 5). Data from a breast cancer xenograft (MDA-MB-468) and a second pancreatic cancer xenograft (FIG. 5B and FIG. 5C, respectively) showed the same pattern, with the anti-Trop-2 ADC significantly more efficacious compared to non-targeting ADC or saline control. In both cases, administration of anti-Trop-2 ADC produced a clear inhibition of tumor growth to the end of the study.

PK and toxicity of hRS7-pro-2-PDox with substitutions of 6.8 or 3.7 drug/IgG—Antibody-drug conjugates (ADCs) carrying as much as 8 ultratoxic drugs/MAb are known to clear faster than unmodified MAb and to increase off-target toxicity, a finding that has led to the current trends to use drug substitutions of <4 (Hamblett et al., 2004, Clin Cancer Res 10:7063-70). ADCs were prepared and evaluated with mean drug/MAb substitution ratios (MSRs) of ~7:1 and ~3:1. Groups of normal mice (n=5) were administered, i.v., single doses of unmodified hRS7 or hRS7-pro-2-PDox with drug substitution of 6.8 or 3.7 (same protein dose), and serum samples were collected at 30 min, 4 h, 24 h, 72 h, and 168 h post-injection. These were analyzed by ELISA for antibody concentration. There were no significant differences in serum concentrations at various times, indicating that these showed similar clearance from the blood. The PK parameters (Cmax, AUC, etc.) were also similar. ADCs with either higher or lower drug substitution had similar tolerability in nude mice, when the administered at the same dose of conjugated drug.

Therapeutic Efficacy at Minimum Effective Dose (MED)—Anti-Trop-2 ADC (hRS7-pro-2-PDox), was evaluated in nude mice bearing NCI-N87 human gastric cancer xenografts by administering a single bolus protein dose of 9 mg/kg, 6.75 mg/kg, 4.5 mg/kg, 2.25 mg/kg, or 1 mg/kg. The therapy was started when the mean tumor volume (mTV) was 0.256 cm$^3$. On day 21, mTV in the saline control group (non-treatment group) was 0.801±0.181 cm$^3$ which was significantly larger than that in mice treated with 9, 6.75, 4.5, or 2.25 mg/kg dose with mTV of 0.211±0.042 cm$^3$, 0.239±0.0.054 cm$^3$, 0.264±0.087 cm$^3$, and 0.567±0.179 cm$^3$, respectively (P<0.0047, one tailed t-test). From these, the minimum effective dose was estimated to be 2.25 mg/kg, while 9 mg/kg represented MTD.

Example 5

Additional Studies With Anti-Trop-2 pro-2-PDox ADC

Figure 6A:
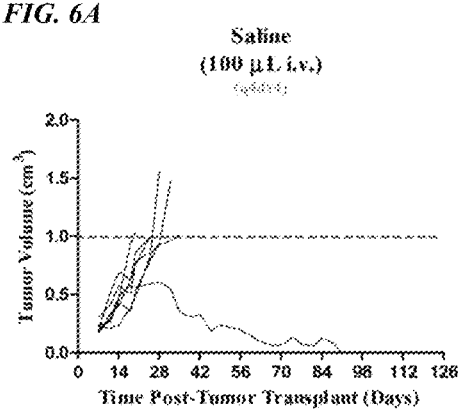
FIG. 6A. In vivo efficacy of pro-2-PDox conjugates in nude mice with NCI-N87 human gastric cancer xenografts. Mice were administered a saline control.
Figure 6B:
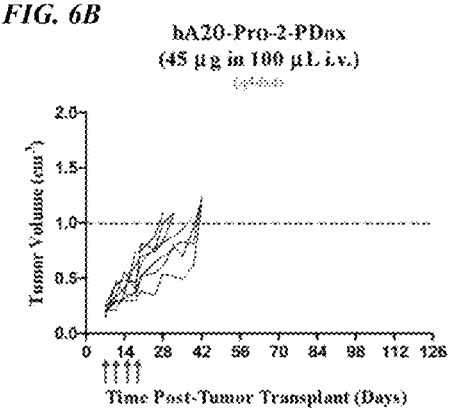
FIG. 6B. In vivo efficacy of pro-2-PDox conjugates in nude mice with NCI-N87 human gastric cancer xenografts. Mice were administered 45 µg of hA20-pro-2-PDox as indicated by arrows.
Figure 6C:
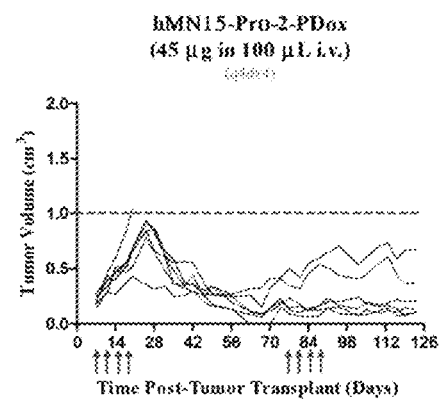
FIG. 6C. In vivo efficacy of pro-2-PDox conjugates in nude mice with NCI-N87 human gastric cancer xenografts. Mice were administered 45 µg of hMN-15-pro-2-PDox as indicated by arrows.
Figure 6D:
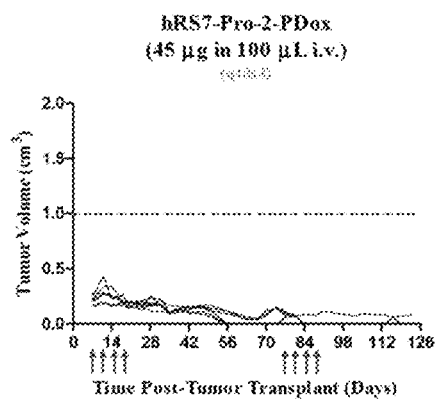
FIG. 6D. In vivo efficacy of pro-2-PDox conjugates in nude mice with NCI-N87 human gastric cancer xenografts. Mice were administered 45 µg of hRS7-pro-2-PDox as indicated by arrows.
Figure 6E:
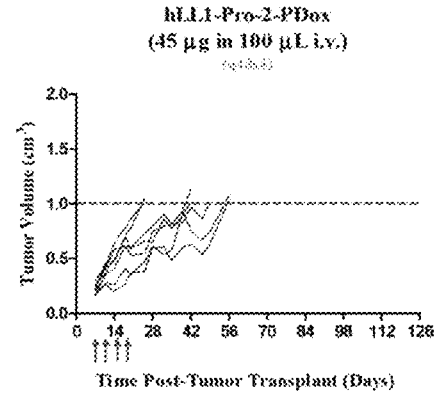
FIG. 6E. In vivo efficacy of pro-2-PDox conjugates in nude mice with NCI-N87 human gastric cancer xenografts. Mice were administered 45 µg of hLL1-pro-2-PDox as indicated by arrows.
Figure 6F:
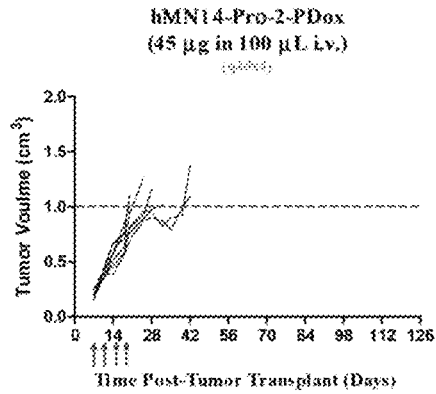
FIG. 6F. In vivo efficacy of pro-2-PDox conjugates in nude mice with NCI-N87 human gastric cancer xenografts. Mice were administered 45 µg of hMN-14-pro-2-PDox as indicated by arrows.

Further in vivo efficacy studies were performed in nude mice implanted with NCI-N87 human gastric cancer xenografts (FIG. 6A-F). One treatment cycle with 4×45 µg of hRS7-pro-2-PDox rapidly regressed all tumors (FIG. 6D). A second treatment cycle was initiated about 2 months after the end of the first cycle, resulting in complete regression of all but one of the hRS7-pro-2-PDox treated animals. The hA20 (anti-CD20), hLL1 (anti-CD22) and hMN-14 (anti-CEACAM5) conjugates had little effect on tumor progression (FIG. 6B, 6E and 6F) compared to saline control (FIG. 6A). Administration of pro-2-PDox-hMN-15 (anti-CEACAM6) resulted in a delayed regression of gastric cancer (FIG. 6C), which was less effective than the hRS7 conjugate (FIG. 6D).

Figure 8A:
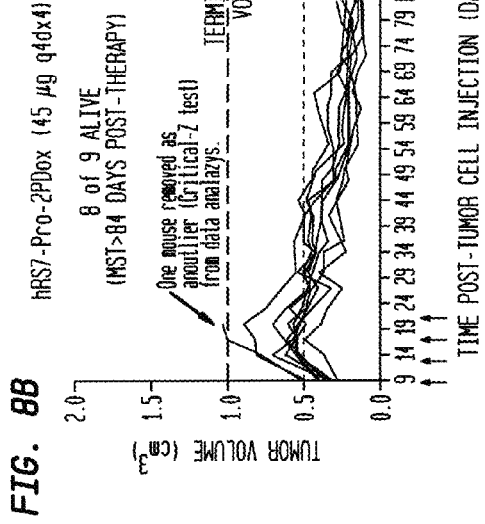
FIG. 8A. Dosing schedule study in mice injected with NCI-N87 human gastric cancer. Mice were administered a saline control.
Figure 8C:
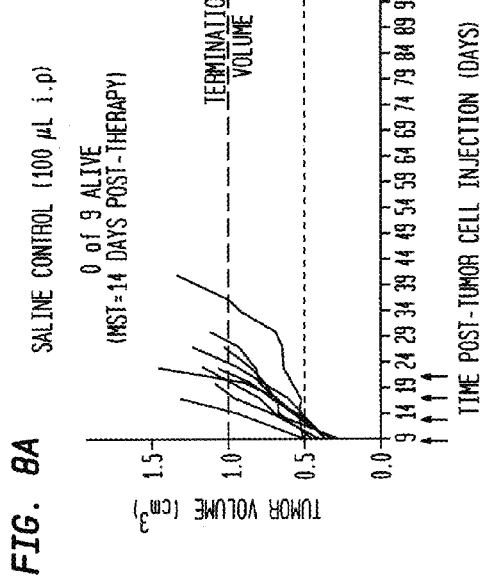
FIG. 8C. Dosing schedule study in mice injected with NCI-N87 human gastric cancer. Mice were administered 90 µg weekly×2 of hRS7-pro-2-PDox.
Figure 8B:
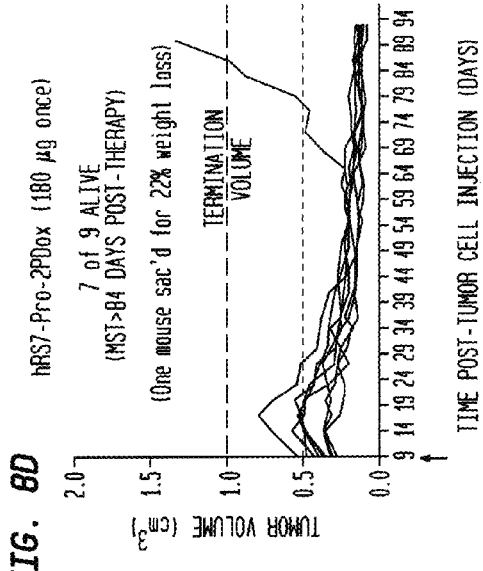
FIG. 8B. Dosing schedule study in mice injected with NCI-N87 human gastric cancer. Mice were administered 45 µg q4d×4 of hRS7-pro-2-PDox.
Figure 8D:
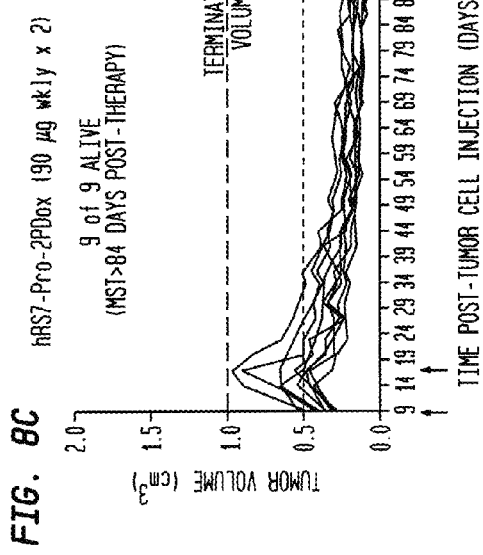
FIG. 8D. Dosing schedule study in mice injected with NCI-N87 human gastric cancer. Mice were administered a single dose of 180 µg hRS7-pro-2-PDox.

The effect of varying dosage schedule of anti-Trop-2 ADC on anti-tumor efficacy was examined (FIG. 7, FIG. 8A-G). The experiment began 9 days after tumor implantation when mean tumor volume for all groups was 0.383 cm$^3$, and ended on day 93 (84 days after initiation of therapy). In this study, administration of anti-Trop-2 ADC as a single dose of 180 µg, two weekly doses of 90 µg, and q4d×4 of 45 µg all resulted in significantly enhanced survival (FIG. 7, FIG. 8B-D). For the saline control, 0 of 9 mice survived (FIG. 8A). For mice receiving 45 q4d×4 of hRS7-pro-2-PDox, 8 of 9 mice were alive at day 94 (FIG. 8B). For mice receiving 90 µg weekly×2 of hRS7-pro-2-PDox, 9 of 9 mice were alive at day 94 (FIG. 8C). For mice receiving a single dose of 180m of hRS7-pro-2-PDox, 7 of 9 mice were alive at day 94 (FIG. 8D).

Figure 8E:
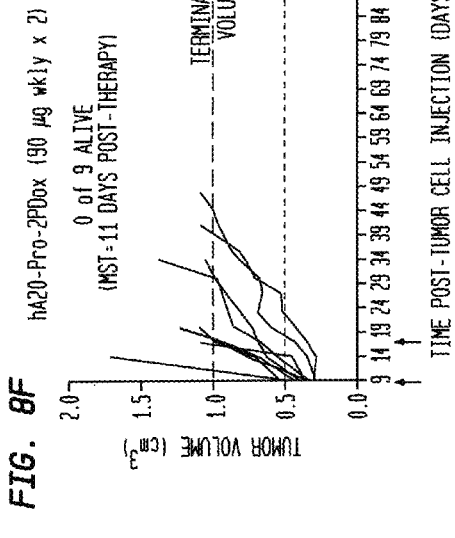
FIG. 8E. Dosing schedule study in mice injected with NCI-N87 human gastric cancer. Mice were administered 45 µg q4d×4 of hA20-pro-2-PDox.
Figure 8F:
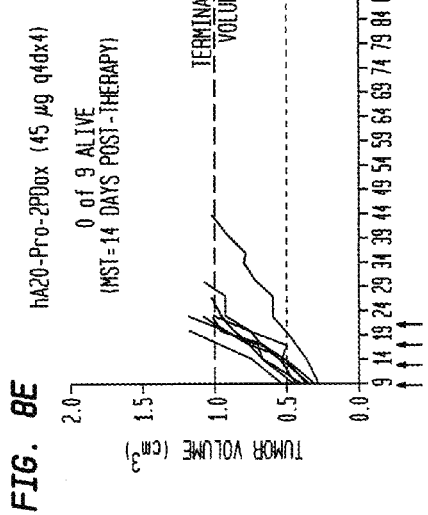
FIG. 8F. Dosing schedule study in mice injected with NCI-N87 human gastric cancer. Mice were administered 90 µg weekly×2 of hA20-pro-2-PDox.
Figure 8G:
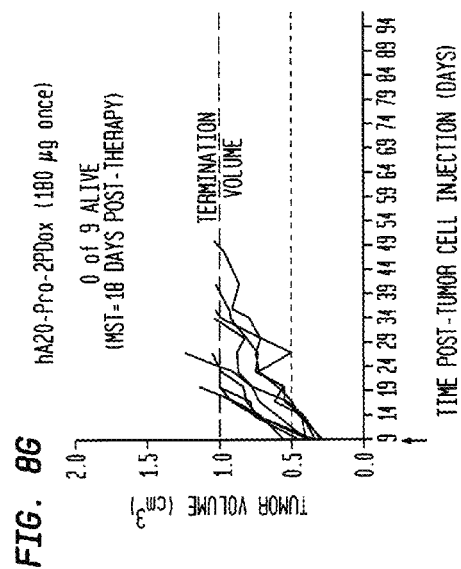
FIG. 8G. Dosing schedule study in mice injected with NCI-N87 human gastric cancer. Mice were administered a single dose of 180 µg hA20-pro-2-PDox.

At the same dosage schedule, the control hA20 conjugate had no effect on survival (FIG. 7, FIG. 8E-F). A toxicity study showed that the three dosage schedules of hRS7-pro-2-PDox resulted in similarly low levels of toxicity (not shown).

The hRS7-pro-2-PDox conjugate was also effective in Capan-1 pancreatic cancer (not shown) and was more effective at inhibiting tumor growth than a hRS7-SN-38 conjugate (not shown). The hPAM4-pro-2-PDox conjugate was also more effective at inhibiting growth of Capan-1 human pancreatic cancer than an hPAM4-SN-38 conjugate (not shown). At 63 days after Capan-1 tumor injection (with therapy starting at 1 days post-innoculation), 0 of 10 mice were alive in the saline control, 10 of 10 mice were alive in mice treated twice weekly×2 weeks with 45 µg of hPAM4-pro-2-PDox, 2 of 10 mice were alive in mice treated twice weekly×2 weeks with 45 µg of hA20-pro-2-PDox, 0 of 10 mice were alive in mice treated twice weekly×4 weeks with 250 µg of hPAM4-SN-38, and 0 of 10 mice were alive in mice treated twice weekly×4 weeks with 250 µg of h20-SN-38.

hRS7-pro-2-PDox was substantially more effective than hRS7-SN-38 at inhibiting growth of PxPC-3 pancreatic cancer (not shown) and was slightly more effective than hRS7-SN-38 at inhibiting growth of MDA-MB-468 breast cancer (not shown).

The effect of different single doses of hRS7-pro-2-PDox on growth of NCI-N87 gastric carcinoma xenografts is shown in FIG. 9. Using a single dose, the maximum effect on tumor growth was observed at 90 µg or higher (FIG. 9).

Survival curves for mice bearing NCI-N87 human gastric carcinoma xenografts and administered a single dose of anti-Trop-2 ADC are shown in FIG. 10. A single dose of 45 µg was the minimum required to see a significant survival benefit compared to saline control (FIG. 10). Mice administered single doses of 90 µg or higher showed 100% survival to the termination of the experiment.

Figure 11:
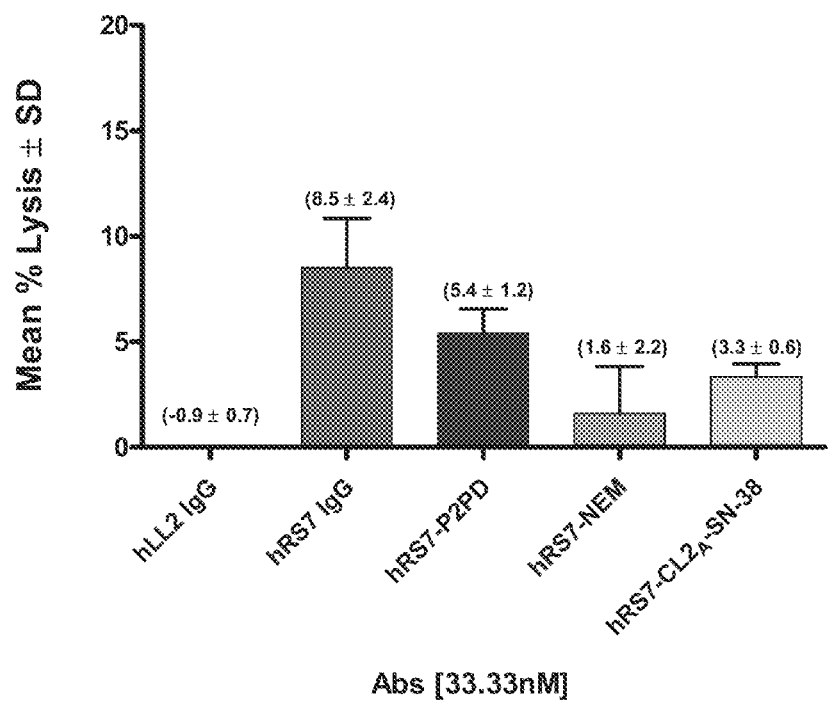
FIG. 11. ADCC of various hRS7-ADCs vs. hRS7 IgG.

The ADCC activity of various hRS7-ADC conjugates was determined in comparison to hRS7 IgG (FIG. 11). PBMCs were purified from blood purchased from the Blood Center of New Jersey. A Trop-2-positive human pancreatic adenocarcinoma cell line (BxPC-3) was used as the target cell line with an effector to target ratio of 100:1. ADCC mediated by hRS7 IgG was compared to hRS7-Pro-2-PDox, hRS7-CL2A-SN-38, and the reduced and capped hRS7-NEM. All were used at 33.3 nM.

Results are shown in FIG. 11. Overall activity was low, but significant. There was 8.5% specific lysis for the hRS7 IgG which was not significantly different from hRS7-Pro-2-PDox. Both were significantly better than hLL2 control and hRS7-NEM and hRS7-SN-38 (P<0.02, two-tailed t-test). There was no difference between hRS7-NEM and hRS7-SN-38.

Example 6

Efficacy of anti-Trop-2-SN-38 ADC Against Diverse Epithelial Cancers In Vivo

Abstract

The purpose of this study was to evaluate the efficacy of an SN-38-anti-Trop-2 (hRS7) ADC against several human solid tumor types, and to assess its tolerability in mice and monkeys, the latter with tissue cross-reactivity to hRS7 similar to humans. Two SN-38 derivatives, CL2-SN-38 and CL2A-SN-38, were conjugated to the anti-Trop-2-humanized antibody, hRS7. The immunoconjugates were characterized in vitro for stability, binding, and cytotoxicity. Efficacy was tested in five different human solid tumor-xenograft models that expressed Trop-2 antigen. Toxicity was assessed in mice and in Cynomolgus monkeys.

The hRS7 conjugates of the two SN-38 derivatives were equivalent in drug substitution (~6), cell binding ($K_d$~1.2 nmol/L), cytotoxicity ($IC_{50}$~2.2 nmol/L), and serum stability in vitro ($t_{1/2}$~20 hours). Exposure of cells to the ADC demonstrated signaling pathways leading to PARP cleavage, but differences versus free SN-38 in p53 and p21 upregulation were noted. Significant antitumor effects were produced by hRS7-SN-38 at nontoxic doses in mice bearing Calu-3 (P≤0.05), Capan-1 (P<0.018), BxPC-3 (P<0.005), and COLO 205 tumors (P<0.033) when compared to non-targeting control ADCs. Mice tolerated a dose of 2×12 mg/kg (SN-38 equivalents) with only short-lived elevations in ALT and AST liver enzyme levels. Cynomolgus monkeys infused with 2×0.96 mg/kg exhibited only transient decreases in blood counts, although, importantly, the values did not fall below normal ranges.

In summary, the anti-Trop-2 hRS7-CL2A-SN-38 ADC provided significant and specific antitumor effects against a range of human solid tumor types. It was well tolerated in monkeys, with tissue Trop-2 expression similar to humans, at clinically relevant doses.

Introduction

Successful irinotecan treatment of patients with solid tumors has been limited, due in large part to the low conversion rate of the CPT-11 prodrug into the active SN-38 metabolite. Others have examined nontargeted forms of SN-38 as a means to bypass the need for this conversion and to deliver SN-38 passively to tumors. We conjugated SN-38 covalently to a humanized anti-Trop-2 antibody, hRS7. This antibody-drug conjugate has specific antitumor effects in a range of s.c. human cancer xenograft models, including non-small cell lung carcinoma, pancreatic, colorectal, and squamous cell lung carcinomas, all at nontoxic doses (e.g., ≤3.2 mg/kg cumulative SN-38 equivalent dose). Trop-2 is widely expressed in many epithelial cancers, but also some normal tissues, and therefore a dose escalation study in Cynomolgus monkeys was performed to assess the clinical safety of this conjugate. Monkeys tolerated 24 mg SN-38 equivalents/kg with only minor, reversible, toxicities. Given its tumor-targeting and safety profile, hRS7-SN-38 provides a significant improvement in the management of solid tumors responsive to irinotecan.

Material and Methods

Cell lines, antibodies, and chemotherapeutics—All human cancer cell lines used in this study were purchased from the American Type Culture Collection. These include Calu-3 (non-small cell lung carcinoma), SK-MES-1 (squamous cell lung carcinoma), COLO 205 (colonic adenocarcinoma), Capan-1 and BxPC-3 (pancreatic adenocarcinomas), and PC-3 (prostatic adenocarcinomas). Humanized RS7 IgG and control humanized anti-CD20 (hA20 IgG, veltuzumab) and anti-CD22 (hLL2 IgG, epratuzumab) antibodies were prepared at Immunomedics, Inc. Irinotecan (20 mg/mL) was obtained from Hospira, Inc.

SN-38 immunoconjugates and in vitro aspects—Synthesis of CL2-SN-38 has been described previously (Moon et al., 2008, J Med Chem 51:6916-26). Its conjugation to hRS7 IgG and serum stability were performed as described (Moon et al., 2008, J Med Chem 51:6916-26; Govindan et al., 2009, Clin Chem Res 15:6052-61). Preparations of CL2A-SN-38 (M.W. 1480) and its hRS7 conjugate, and stability, binding, and cytotoxicity studies, were conducted as described in the preceding Examples.

In vivo therapeutic studies—For all animal studies, the doses of SN-38 immunoconjugates and irinotecan are shown in SN-38 equivalents. Based on a mean SN-38/IgG substitution ratio of 6, a dose of 500 µg ADC to a 20-g mouse (25 mg/kg) contains 0.4 mg/kg of SN-38. Irinotecan doses are likewise shown as SN-38 equivalents (i.e., 40 mg irinotecan/kg is equivalent to 24 mg/kg of SN-38).

NCr female athymic nude (nu/nu) mice, 4 to 8 weeks old, and male Swiss-Webster mice, 10 weeks old, were purchased from Taconic Farms. Tolerability studies were performed in Cynomolgus monkeys (*Macaca fascicularis*; 2.5-4 kg male and female) by SNBL USA, Ltd.

Animals were implanted subcutaneously with different human cancer cell lines. Tumor volume (TV) was determined by measurements in 2 dimensions using calipers, with volumes defined as: L×w²/2, where L is the longest dimension of the tumor and w is the shortest. Tumors ranged in size between 0.10 and 0.47 cm³ when therapy began. Treatment regimens, dosages, and number of animals in each experiment are described in the Results. The lyophilized hRS7-CL2A-SN-38 and control ADC were reconstituted and diluted as required in sterile saline. All reagents were administered intraperitoneally (0.1 mL), except irinotecan, which was administered intravenously. The dosing regimen was influenced by our prior investigations, where the ADC was given every 4 days or twice weekly for varying lengths of time (Moon et al., 2008, J Med Chem 51:6916-26; Govindan et al., 2009, Clin Chem Res 15:6052-61). This dosing frequency reflected a consideration of the conjugate's serum half-life in vitro, to allow a more continuous exposure to the ADC.

Statistics—Growth curves are shown as percent change in initial TV over time. Statistical analysis of tumor growth was based on area under the curve (AUC). Profiles of individual tumor growth were obtained through linear-curve modeling. An f-test was employed to determine equality of variance between groups before statistical analysis of growth curves. A 2-tailed t-test was used to assess statistical significance between the various treatment groups and controls, except for the saline control, where a 1-tailed t-test was used (significance at $P \leq 0.05$). Statistical comparisons of AUC were performed only up to the time that the first animal within a group was euthanized due to progression.

Pharmacokinetics and biodistribution—$^{111}$In-radiolabeled hRS7-CL2A-SN-38 and hRS7 IgG were injected into nude mice bearing s.c. SK-MES-1 tumors (~0.3 cm$^3$). One group was injected intravenously with 20 µCi (250-µg protein) of $^{111}$In-hRS7-CL2A-SN-38, whereas another group received 20 µCi (250-µg protein) of $^{111}$In-hRS7 IgG. At various timepoints mice (5 per timepoint) were anesthetized, bled via intracardiac puncture, and then euthanized. Tumors and various tissues were removed, weighed, and counted by γ scintillation to determine the percentage injected dose per gram tissue (% ID/g). A third group was injected with 250 µg of unlabeled hRS7-CL2A-SN-38 3 days before the administration of $^{111}$In-hRS7-CL2A-SN-38 and likewise necropsied. A 2-tailed t-test was used to compare hRS7-CL2A-SN-38 and hRS7 IgG uptake after determining equality of variance using the f-test. Pharmacokinetic analysis on blood clearance was performed using WinNon-Lin software (Parsight Corp.).

Tolerability in Swiss-Webster mice and Cynomolgus monkeys—Briefly, mice were sorted into 4 groups each to receive 2-mL i.p. injections of either a sodium acetate buffer control or 3 different doses of hRS7-CL2A-SN-38 (4, 8, or 12 mg/kg of SN-38) on days 0 and 3 followed by blood and serum collection, as described in Results. Cynomolgus monkeys (3 male and 3 female; 2.5-4.0 kg) were administered 2 different doses of hRS7-CL2A-SN-38. Dosages, times, and number of monkeys bled for evaluation of possible hematologic toxicities and serum chemistries are described in the Results.

Results

Figure 12A:
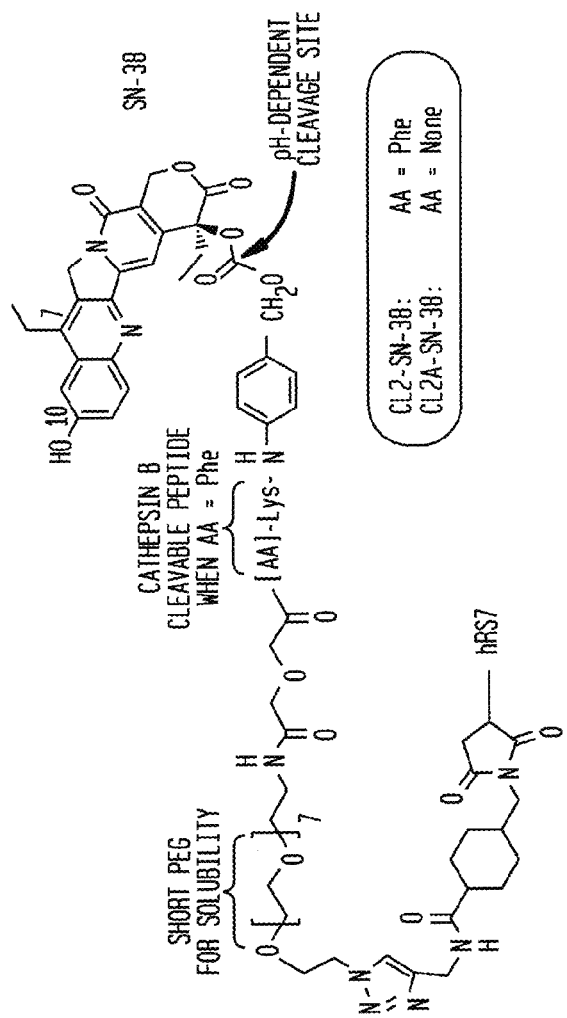
FIG. 12A. Structures of CL2-SN-38 and CL2A-SN-38.

Stability and potency of hRS7-CL2A-SN-38—Two different linkages were used to conjugate SN-38 to hRS7 IgG (FIG. 12A). The first is termed CL2-SN-38 and has been described previously (Moon et al., 2008, J Med Chem 51:6916-26; Govindan et al., 2009, Clin Chem Res 15:6052-61). A change in the synthesis of CL2 to remove the phenylalanine moiety within the linker was used to produce the CL2A linker. This change simplified the synthesis, but did not affect the conjugation outcome (e.g., both CL2-SN-38 and CL2A-SN-38 incorporated ~6 SN-38 per IgG molecule). Side-by-side comparisons found no significant differences in serum stability, antigen binding, or in vitro cytotoxicity. This result was surprising, since the phenylalanine residue in CL2 is part of a designed cleavage site for cathepsin B, a lysosomal protease.

Figure 12B:
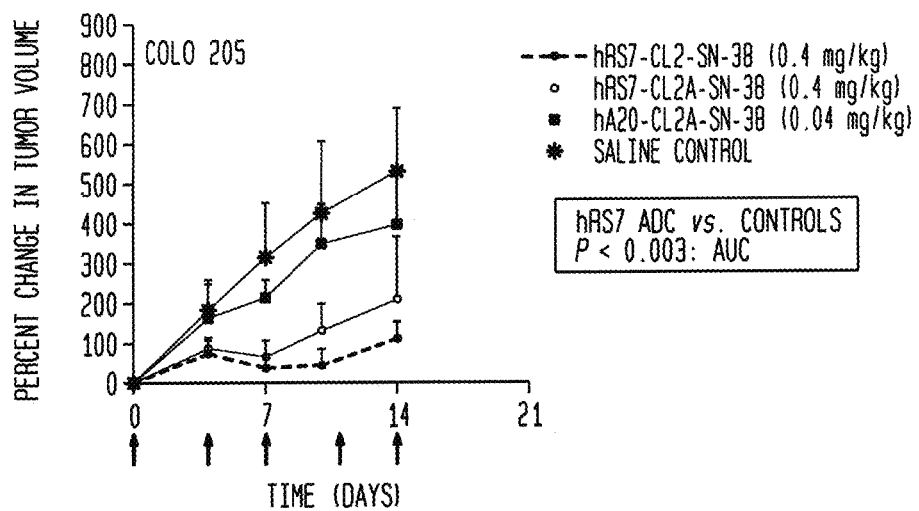
FIG. 12B. Comparative efficacy of anti-Trop-2 ADC linked to CL2 vs. CL2A linkers versus hA20 ADC and saline control, using COLO 205 colonic adenocarcinoma. Animals were treated twice weekly for 4 weeks as indicated by the arrows. COLO 205 mice (N=6) were treated with 0.4 mg/kg ADC and tumors measured twice a week.
Figure 12C:
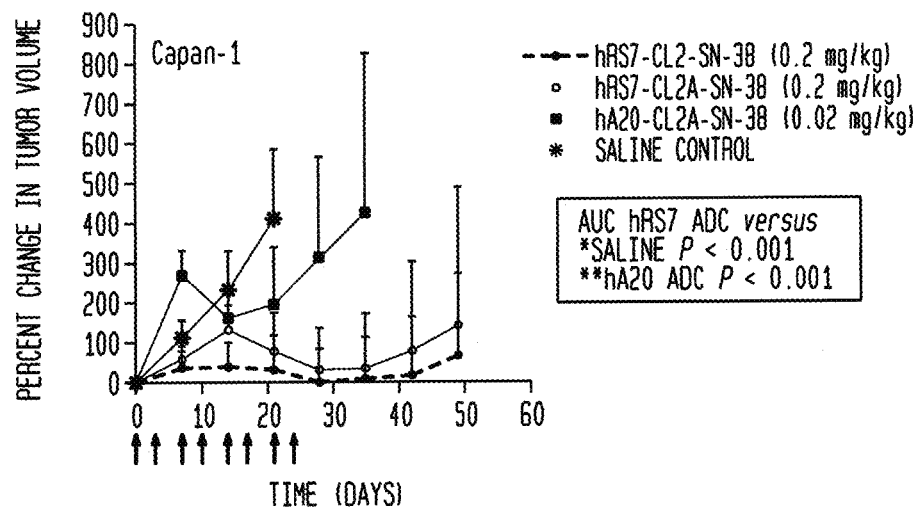
FIG. 12C. Comparative efficacy of anti-Trop-2 ADC linked to CL2 vs. CL2A linkers versus hA20 ADC and saline control, using Capan-1 pancreatic adenocarcinoma. Animals were treated twice weekly for 4 weeks as indicated by the arrows. Capan-1 mice (N=10) were treated with 0.2 mg/kg ADC and tumors measured weekly.

To confirm that the change in the SN-38 linker from CL2 to CL2A did not impact in vivo potency, hRS7-CL2A and hRS7-CL2-SN-38 were compared in mice bearing COLO 205 (FIG. 12B) or Capan-1 tumors (FIG. 12C), using 0.4 mg or 0.2 mg/kg SN-38 twice weekly×4 weeks, respectively, and with starting tumors of 0.25 cm$^3$ size in both studies. Both the hRS7-CL2A and CL2-SN-38 conjugates significantly inhibited tumor growth compared to untreated (AUC$_{14days}$ P<0.002 vs. saline in COLO 205 model; AUC$_{21days}$ P<0.001 vs. saline in Capan-1 model), and a nontargeting anti-CD20 control ADC, hA20-CL2A-SN-38 (AUC$_{14days}$ P<0.003 in COLO-205 model; AUC$_{35days}$: P<0.002 in Capan-1 model). At the end of the study (day 140) in the Capan-1 model, 50% of the mice treated with hRS7-CL2A-SN-38 and 40% of the hRS7-CL2-SN-38 mice were tumor-free, whereas only 20% of the hA20-ADC-treated animals had no visible sign of disease. As demonstrated in FIG. 12, the CL2A linker resulted in a somewhat higher efficacy compared to CL2.

Mechanism of action—In vitro cytotoxicity studies demonstrated that hRS7-CL2A-SN-38 had IC$_{50}$ values in the nmol/L range against several different solid tumor lines (Table 6). The IC. with free SN-38 was lower than the conjugate in all cell lines. Although there was no apparent correlation between Trop-2 expression and sensitivity to hRS7-CL2A-SN-38, the IC$_{50}$ ratio of the ADC versus free SN-38 was lower in the higher Trop-2-expressing cells, most likely reflecting the enhanced ability to internalize the drug when more antigen is present.

SN-38 is known to activate several signaling pathways in cells, leading to apoptosis (e.g., Cusack et al., 2001, Cancer Res 61:3535-40; Liu et al. 2009, Cancer Lett 274:47-53; Lagadec et al., 2008, Br J Cancer 98:335-44). Our initial studies examined the expression of 2 proteins involved in early signaling events (p21$^{Waf1/Cip1}$ and p53) and 1 late apoptotic event [cleavage of poly-ADP-ribose polymerase (PARP)] in vitro (not shown). In BxPC-3, SN-38 led to a 20-fold increase in p21$^{Waf1/Cip1}$ expression (not shown), whereas hRS7-CL2A-SN-38 resulted in only a 10-fold increase (not shown), a finding consistent with the higher activity with free SN-38 in this cell line (Table 6). However, hRS7-CL2A-SN-38 increased p21$^{Waf1/Cip1}$ expression in Calu-3 more than 2-fold over free SN-38 (not shown).

A greater disparity between hRS7-CL2A-SN-38- and free SN-38-mediated signaling events was observed in p53 expression (not shown). In both BxPC-3 and Calu-3, upregulation of p53 with free SN-38 was not evident until 48 hours, whereas hRS7-CL2A-SN-38 upregulated p53 within 24 hours (not shown). In addition, p53 expression in cells exposed to the ADC was higher in both cell lines compared to SN-38 (not shown). Interestingly, although hRS7 IgG had no appreciable effect on p21$^{Waf1/Cip1}$ expression, it did induce the upregulation of p53 in both BxPC-3 and Calu-3, but only after a 48-hour exposure (not shown). In terms of later apoptotic events, cleavage of PARP was evident in both cell lines when incubated with either SN-38 or the conjugate (not shown). The presence of the cleaved PARP was higher at 24 hours in BxPC-3 (not shown), which correlates with high expression of p21 and its lower IC$_{50}$. The higher degree of cleavage with free SN-38 over the ADC was consistent with the cytotoxicity findings.

Figure 13A:
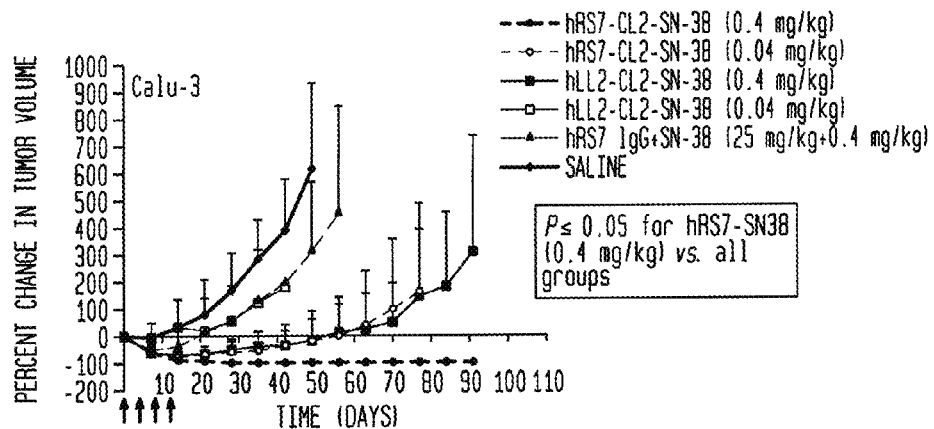
FIG. 13A. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). Mice bearing Calu-3 tumors (N=5-7) were injected with hRS7-CL2-SN-38 every 4 days for a total of 4 injections (q4d×4).

Efficacy of hRS7-SN-38—Because Trop-2 is widely expressed in several human carcinomas, studies were performed in several different human cancer models, which started using the hRS7-CL2-SN-38 linkage, but later, conjugates with the CL2A-linkage were used. Calu-3-bearing nude mice given 0.04 mg SN-38/kg of the hRS7-CL2-SN-38 every 4 days×4 had a significantly improved response compared to animals administered the equivalent amount of non-targeting hLL2-CL2-SN-38 (TV=0.14±0.22 cm$^3$ vs. 0.80±0.91 cm$^3$, respectively; AUC$_{42days}$ P<0.026; FIG. 13A). A dose-response was observed when the dose was increased to 0.4 mg/kg SN-38 (FIG. 13A). At this higher dose level, all mice given the specific hRS7 conjugate were "cured" within 28 days, and remained tumor-free until the end of the study on day 147, whereas tumors regrew in animals treated with the irrelevant ADC (specific vs. irrelevant AUC$_{98days}$: P=0.05). In mice receiving the mixture of hRS7 IgG and SN-38, tumors progressed >4.5-fold by day 56 (TV=1.10±0.88 cm$^3$; AUC$_{56days}$ P<0.006 vs. hRS7-CL2-SN-38) (FIG. 13A).

Figure 13B:
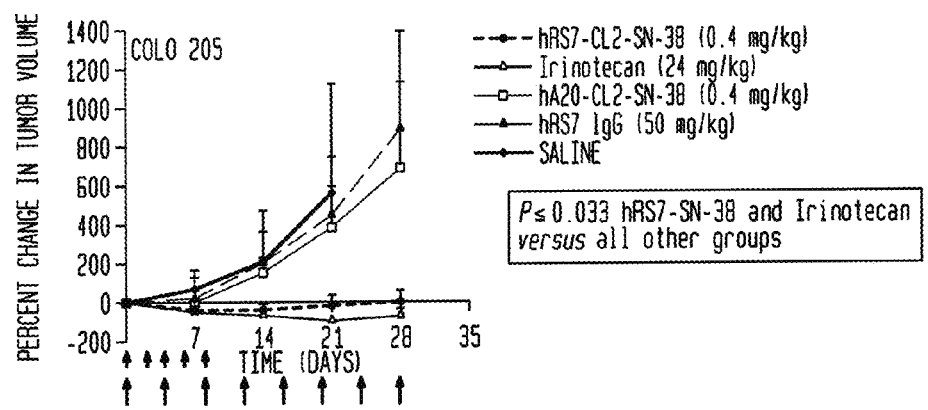
FIG. 13B. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). COLO 205 tumor-bearing mice (N=5) were injected 8 times (q4d×8) with the ADC or every 2 days for a total of 5 injections (q2d×5) with the MTD of irinotecan.
Figure 13C:
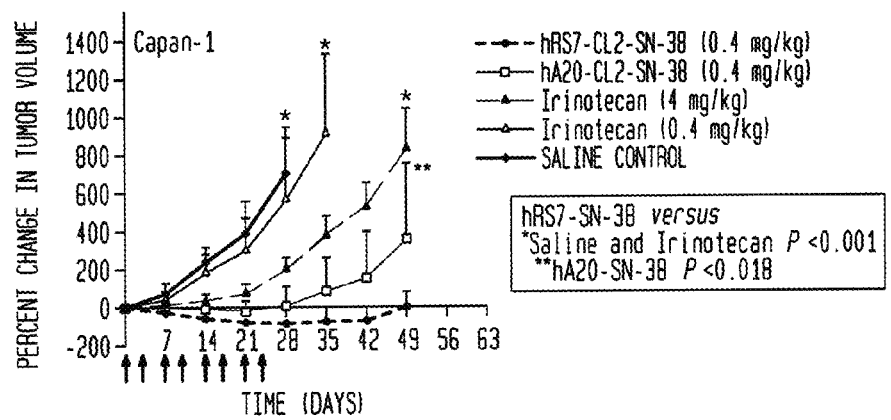
FIG. 13C. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). Capan-1 (N=10) were treated twice weekly for 4 weeks with the agents indicated.
Figure 13D:
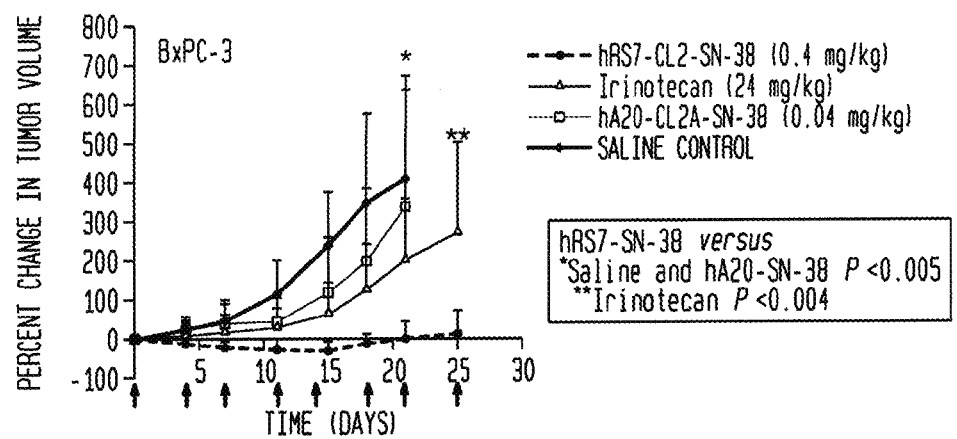
FIG. 13D. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). BxPC-3 tumor-bearing mice (N=10) were treated twice weekly for 4 weeks with the agents indicated.
Figure 13E:
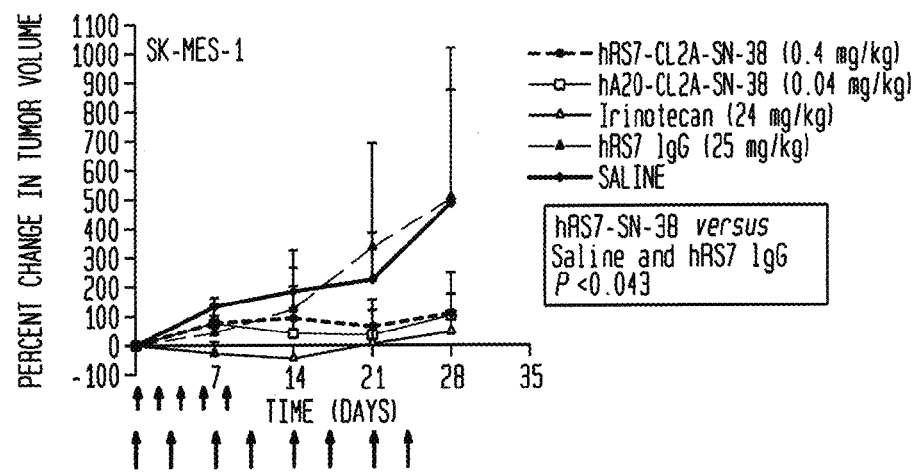
FIG. 13E. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). In addition to ADC given twice weekly for 4 week, SK-MES-1 tumor-bearing (N=8) mice received the MTD of CPT-11 (q2d×5).

Efficacy also was examined in human colonic (COLO 205) and pancreatic (Capan-1) tumor xenografts. In COLO 205 tumor-bearing animals, (FIG. 13B), hRS7-CL2-SN-38 (0.4 mg/kg, q4d×8) prevented tumor growth over the 28-day treatment period with significantly smaller tumors compared to control anti-CD20 ADC (hA20-CL2-SN-38), or hRS7 IgG (TV=0.16±0.09 cm$^3$, 1.19±0.59 cm$^3$, and 1.77±0.93 cm$^3$, respectively; AUC$_{28days}$ P<0.016).

mice bearing BxPC-3 human pancreatic tumors (FIG. 13D), hRS7-CL2A-SN-38 again significantly inhibited tumor growth in comparison to control mice treated with saline or an equivalent amount of nontargeting hA20-CL2A-SN-38 (TV=0.24±0.11 cm$^3$ vs. 1.17±0.45 cm$^3$ and 1.05±0.73 cm$^3$, respectively; AUC$_{day21}$P<0.001), or irinotecan given at a 10-fold higher SN-38 equivalent dose (TV=0.27±0.18 cm$^3$ vs. 0.90±0.62 cm$^3$, respectively; AUC$_{day25}$P<0.004) (FIG. 13D). Interestingly, in mice bearing SK-MES-1 human squamous cell lung tumors treated with 0.4 mg/kg of the ADC (FIG. 13E), tumor growth inhibition was superior to saline or unconjugated hRS7 IgG (TV=0.36±0.25 cm$^3$ vs. 1.02±0.70 cm$^3$ and 1.30±1.08 cm$^3$, respectively; AUC$_{28days}$P<0.043), but nontargeting hA20-CL2A-SN-38 or the MTD of irinotecan provided the same antitumor effects as the specific hRS7-SN-38 conjugate (FIG. 13E).

In all murine studies, the hRS7-SN-38 ADC was well tolerated in terms of body weight loss (not shown).

Biodistribution of hRS7-CL2A-SN-38—The biodistributions of hRS7-CL2A-SN-38 or unconjugated hRS7 IgG were compared in mice bearing SK-MES-1 human squamous cell lung carcinoma xenografts (not shown), using the respective $^{111}$In-labeled substrates. A pharmacokinetic analysis was performed to determine the clearance of hRS7-CL2A-SN-38 relative to unconjugated hRS7 (not shown).

TABLE 6

Expression of Trop-2 in vitro cytotoxicity of SN-38 and hRS7-SN-38 in various solid tumor lines

| | Trop-2 expression via FACS | | Cytotoxicity results | | | | |
| --- | --- | --- | --- | --- | --- | --- | --- |
| Cell line | Median fluorescence (background) | Percent positive | SN-38 IC$_{50}$ (nmol/L) | 95% CI IC$_{50}$ (nmol/L) | hRS7-SN-38 IC$_{50}$ (nmol/L) | 95% CI IC$_{50}$ (nmol/L) | ADC/free SN-38 ratio |
| Calu-3 | 282.2 (4.7) | 99.6% | 7.19 | 5.77-8.95 | 9.97 | 8.12-12.25 | 1.39 |
| COLO 205 | 141.5 (4.5) | 99.5% | 1.02 | 0.66-1.57 | 1.95 | 1.26-3.01 | 1.91 |
| Capan-1 | 100.0 (5.0) | 94.2% | 3.50 | 2.17-5.65 | 6.99 | 5.02-9.72 | 2.00 |
| PC-3 | 46.2 (5.5) | 73.6% | 1.86 | 1.16-2.99 | 4.24 | 2.99-6.01 | 2.28 |
| SK-MES-1 | 44.0 (3.5) | 91.2% | 8.61 | 6.30-11.76 | 23.14 | 17.98-29.78 | 2.69 |
| BxPC-3 | 26.4 (3.1) | 98.3% | 1.44 | 1.04-2.00 | 4.03 | 3.25-4.98 | 2.80 |

The MTD of irinotecan (24 mg SN-38/kg, q2d×5) was as effective as hRS7-CL2-SN-38 in COLO 205 cells, because mouse serum can more efficiently convert irinotecan to SN-38 (Morton et al., 2000, Cancer Res 60:4206-10) than human serum, but the SN-38 dose in irinotecan (2,400 μg cumulative) was 37.5-fold greater than with the conjugate (64 μg total).

Animals bearing Capan-1 (FIG. 13C) showed no significant response to irinotecan alone when given at an SN-38-dose equivalent to the hRS7-CL2-SN-38 conjugate (e.g., on day 35, average tumor size was 0.04±0.05 cm$^3$ in animals given 0.4 mg SN-38/kg hRS7-SN-38 vs. 1.78±0.62 cm$^3$ in irinotecan-treated animals given 0.4 mg/kg SN-38; AUC$_{day35}$ P<0.001; FIG. 13C). When the irinotecan dose was increased 10-fold to 4 mg/kg SN-38, the response improved, but still was not as significant as the conjugate at the 0.4 mg/kg SN-38 dose level (TV=0.17±0.18 cm$^3$ vs. 1.69±0.47 cm', AUC$_{day49}$P<0.001) (FIG. 13C). An equal dose of nontargeting hA20-CL2-SN-38 also had a significant antitumor effect as compared to irinotecan-treated animals, but the specific hRS7 conjugate was significantly better than the irrelevant ADC (TV=0.17±0.18 cm$^3$ vs. 0.80±0.68 cm$^3$, AUC$_{day49}$P<0.018) (FIG. 13C).

Studies with the hRS7-CL2A-SN-38 ADC were then extended to 2 other models of human epithelial cancers. In The ADC cleared faster than the equivalent amount of unconjugated hRS7, with the ADC exhibiting ~40% shorter half-life and mean residence time. Nonetheless, this had a minimal impact on tumor uptake (not shown). Although there were significant differences at the 24- and 48-hour timepoints, by 72 hours (peak uptake) the amounts of both agents in the tumor were similar. Among the normal tissues, hepatic and splenic differences were the most striking (not shown). At 24 hours postinjection, there was >2-fold more hRS7-CL2A-SN-38 in the liver than hRS7 IgG (not shown). Conversely, in the spleen there was 3-fold more parental hRS7 IgG present at peak uptake (48-hour timepoint) than hRS7-CL2A-SN-38 (not shown). Uptake and clearance in the rest of the tissues generally reflected differences in the blood concentration (not shown).

Because twice-weekly doses were given for therapy, tumor uptake in a group of animals that first received a predose of 0.2 mg/kg (250 μg protein) of the hRS7 ADC 3 days before the injection of the $^{111}$In-labeled antibody was examined. Tumor uptake of $^{111}$In-hRS7-CL2A-SN-38 in predosed mice was substantially reduced at every timepoint in comparison to animals that did not receive the predose (e.g., at 72 hours, predosed tumor uptake was 12.5%±3.8% ID/g vs. 25.4%±8.1% ID/g in animals not given the predose;

P=0.0123; not shown). Predosing had no appreciable impact on blood clearance or tissue uptake (not shown). These studies suggest that in some tumor models, tumor accretion of the specific antibody can be reduced by the preceding dose(s), which likely explains why the specificity of a therapeutic response could be diminished with increasing ADC doses and why further dose escalation is not indicated.

Figure 14A:
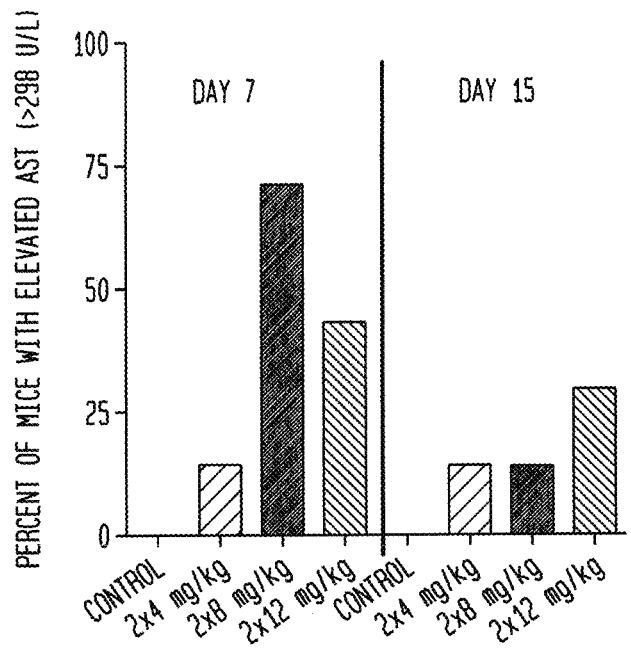
FIG. 14A. Tolerability of hRS7-CL2A-SN-38 in Swiss-Webster mice. Fifty-six Swiss-Webster mice were administered 2 i.p. doses of buffer or the hRS7-CL2A-SN-38 3 days apart (4, 8, or 12 mg/kg of SN-38 per dose; 250, 500, or 750 mg conjugate protein/kg per dose). Seven and 15 days after the last injection, 7 mice from each group were euthanized, with blood counts and serum chemistries performed. Graphs show the percent of animals in each group that had elevated levels of AST.
Figure 14B:
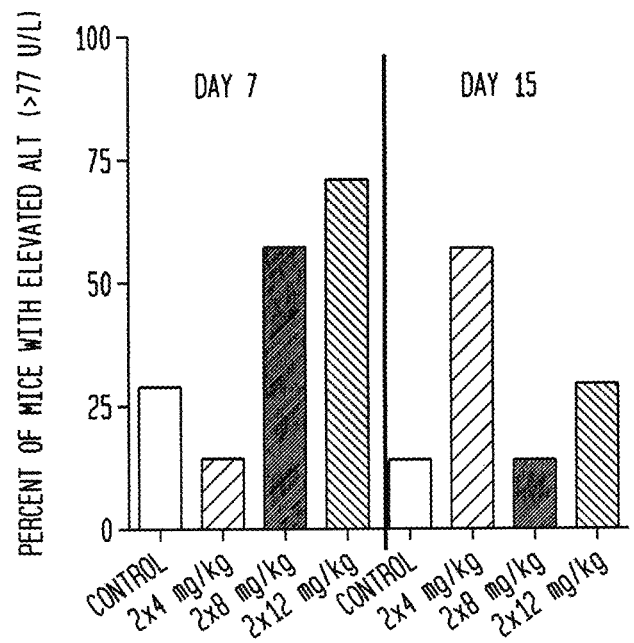
FIG. 14B. Tolerability of hRS7-CL2A-SN-38 in Swiss-Webster mice. Fifty-six Swiss-Webster mice were administered 2 i.p. doses of buffer or the hRS7-CL2A-SN-38 3 days apart (4, 8, or 12 mg/kg of SN-38 per dose; 250, 500, or 750 mg conjugate protein/kg per dose). Seven and 15 days after the last injection, 7 mice from each group were euthanized, with blood counts and serum chemistries performed. Graphs show the percent of animals in each group that had elevated levels of ALT.

Tolerability of hRS7-CL2A-SN-38 in Swiss-Webster mice and Cynomolgus monkeys Swiss-Webster mice tolerated 2 doses over 3 days, each of 4, 8, and 12 mg SN-38/kg of the hRS7-CL2A-SN-38, with minimal transient weight loss (not shown). No hematopoietic toxicity occurred and serum chemistries only revealed elevated aspartate transaminase (AST, FIG. 14A) and alanine transaminase (ALT, FIG. 14B). Seven days after treatment, AST rose above normal levels (>298 U/L) in all 3 treatment groups (FIG. 14A), with the largest proportion of mice being in the 2×8 mg/kg group. However, by 15 days posttreatment, most animals were within the normal range. ALT levels were also above the normal range (>77 U/L) within 7 days of treatment (FIG. 14B) and with evidence of normalization by Day 15. Livers from all these mice did not show histologic evidence of tissue damage (not shown). In terms of renal function, only glucose and chloride levels were somewhat elevated in the treated groups. At 2×8 mg/kg, 5 of 7 mice had slightly elevated glucose levels (range of 273-320 mg/dL, upper end of normal 263 mg/dL) that returned to normal by 15 days postinjection. Similarly, chloride levels were slightly elevated, ranging from 116 to 127 mmol/L (upper end of normal range 115 mmol/L) in the 2 highest dosage groups (57% in the 2×8 mg/kg group and 100% of the mice in the 2×12 mg/kg group), and remained elevated out to 15 days postinjection. This also could be indicative of gastrointestinal toxicity, because most chloride is obtained through absorption by the gut; however, at termination, there was no histologic evidence of tissue damage in any organ system examined (not shown).

Because mice do not express Trop-2 identified by hRS7, a more suitable model was required to determine the potential of the hRS7 conjugate for clinical use. Immunohistology studies revealed binding in multiple tissues in both humans and Cynomolgus monkeys (breast, eye, gastrointestinal tract, kidney, lung, ovary, fallopian tube, pancreas, parathyroid, prostate, salivary gland, skin, thymus, thyroid, tonsil, ureter, urinary bladder, and uterus; not shown). Based on this cross-reactivity, a tolerability study was performed in monkeys.

Figure 14C:
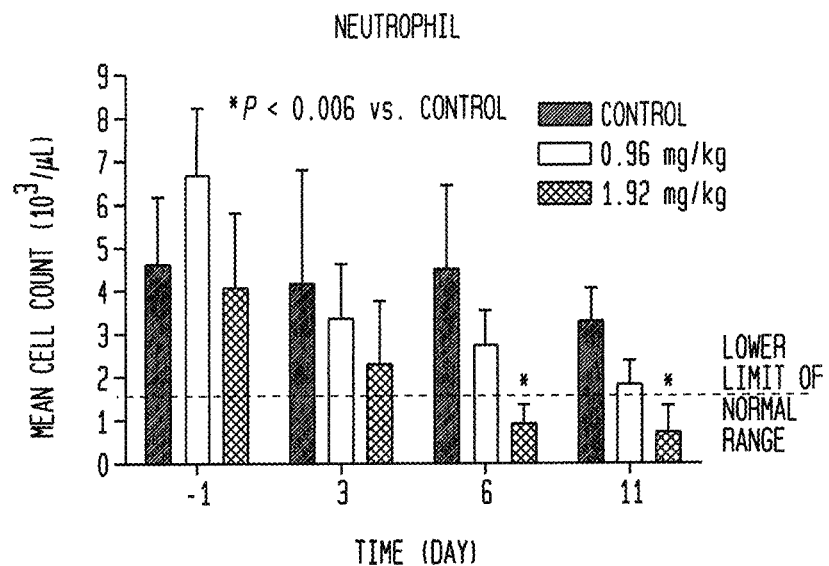
FIG. 14C. Tolerability of hRS7-CL2A-SN-38 in Cynomolgus monkeys. Six monkeys per group were injected twice 3 days apart with buffer (control) or hRS7-CL2A-SN-38 at 0.96 mg/kg or 1.92 mg/kg of SN-38 equivalents per dose (60 and 120 mg/kg conjugate protein). All animals were bled on day-1, 3, and 6. Four monkeys were bled on day 11 in the 0.96 mg/kg group, 3 in the 1.92 mg/kg group. Changes in neutrophil counts in Cynomolgus monkeys.
Figure 14D:
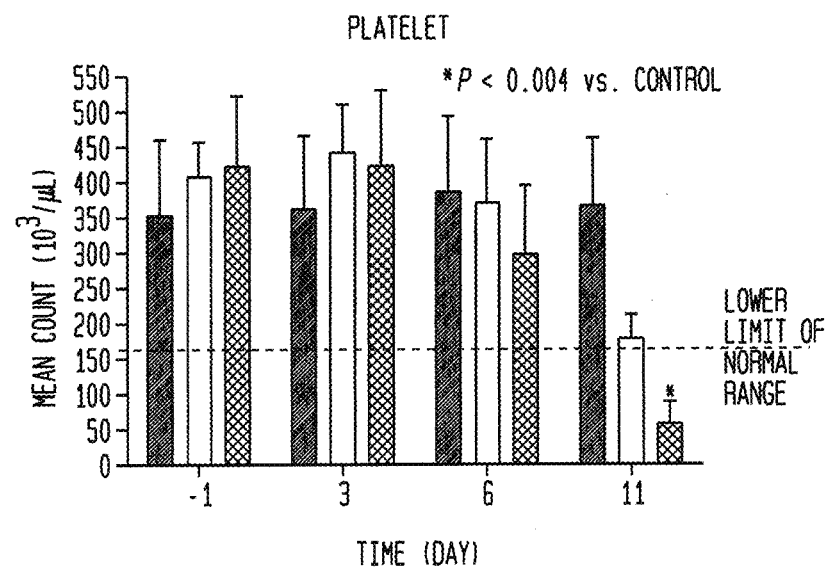
FIG. 14D. Tolerability of hRS7-CL2A-SN-38 in Cynomolgus monkeys. Six monkeys per group were injected twice 3 days apart with buffer (control) or hRS7-CL2A-SN-38 at 0.96 g/kg or 1.92 mg/kg of SN-38 equivalents per dose (60 and 120 mg/kg conjugate protein). All animals were bled on day-1, 3, and 6. Four monkeys were bled on day 11 in the 0.96 mg/kg group, 3 in the 1.92 mg/kg group. Changes in platelet counts in Cynomolgus monkeys.

The group receiving 2×0.96 mg SN-38/kg of hRS7-CL2A-SN-38 had no significant clinical events following the infusion and through the termination of the study. Weight loss did not exceed 7.3% and returned to acclimation weights by day 15. Transient decreases were noted in most of the blood count data (neutrophil and platelet data shown in FIG. 14C and FIG. 14D), but values did not fall below normal ranges. No abnormal values were found in the serum chemistries. Histopathology of the animals necropsied on day 11 (8 days after last injection) showed microscopic changes in hematopoietic organs (thymus, mandibular and mesenteric lymph nodes, spleen, and bone marrow), gastrointestinal organs (stomach, duodenum, jejunum, ileum, cecum, colon, and rectum), female reproductive organs (ovary, uterus, and vagina), and at the injection site. These changes ranged from minimal to moderate and were fully reversed at the end of the recovery period (day 32) in all tissues, except in the thymus and gastrointestinal tract, which were trending towards full recovery at this later timepoint (not shown).

At the 2×1.92 mg SN-38/kg dose level of the conjugate, there was 1 death arising from gastrointestinal complications and bone marrow suppression, and other animals within this group showed similar, but more severe adverse events than the 2×0.96 mg/kg group (not shown). These data indicate that dose-limiting toxicities were identical to that of irinotecan; namely, intestinal and hematologic. Thus, the MTD for hRS7-CL2A-SN-38 lies between 2×0.96 and 1.92 mg SN-38/kg, which represents a human equivalent dose of 2×0.3 to 0.6 mg/kg SN-38.

Discussion

Trop-2 is a protein expressed on many epithelial tumors, including lung, breast, colorectal, pancreas, prostate, and ovarian cancers, making it a potentially important target for delivering cytotoxic agents (Ohmachi et al., 2006, Clin Cancer Res 12:3057-63; Fong et al., 2008, Br J Cancer 99:1290-95; Cubas et al., 2009, Biochim Biophys Acta 1796:309-14). The RS7 antibody internalizes when bound to Trop-2 (Shih et al., 1995, Cancer Res 55:5857s-63s), which enables direct intracellular delivery of cytotoxics.

SN-38 is a potent topoisomerase-I inhibitor, with $IC_{50}$ values in the nanomolar range in several cell lines. It is the active form of the prodrug, irinotecan, that is used for the treatment of colorectal cancer, and which also has activity in lung, breast, and brain cancers. We reasoned that a directly targeted SN-38, in the form of an ADC, would be a significantly improved therapeutic over CPT-11, by overcoming the latter's low and patient-variable bioconversion to active SN-38 (Mathijssen et al., 2001, Clin Cancer Res 7:2182-94).

The Phe-Lys peptide inserted in the original CL2 derivative allowed for possible cleavage via cathepsin B. To simplify the synthetic process, in CL2A the phenylalanine was eliminated, and thus the cathepsin B cleavage site was removed. Interestingly, this product had a better-defined chromatographic profile compared to the broad profile obtained with CL2 (not shown), but more importantly, this change had no impact on the conjugate's binding, stability, or potency in side-by-side testing. These data suggest that SN-38 in CL2 was released from the conjugate primarily by the cleavage at the pH-sensitive benzyl carbonate bond to SN-38's lactone ring and not the cathepsin B cleavage site.

In vitro cytotoxicity of hRS7 ADC against a range of solid tumor cell lines consistently had $IC_{50}$ values in the nmol/L range. However, cells exposed to free SN-38 demonstrated a lower $IC_{50}$ value compared to the ADC. This disparity between free and conjugated SN-38 was also reported for ENZ-2208 (Sapra et al., 2008, Clin Cancer Res 14:1888-96, Zhao et al., 2008, Bioconjug Chem 19:849-59) and NK012 (Koizumi et al., 2006, Cancer Res 66:10048-56). ENZ-2208 utilizes a branched PEG to link about 3.5 to 4 molecules of SN-38 per PEG, whereas NK012 is a micelle nanoparticle containing 20% SN-38 by weight. With our ADC, this disparity (i.e., ratio of potency with free vs. conjugated SN-38) decreased as the Trop-2 expression levels increased in the tumor cells, suggesting an advantage to targeted delivery of the drug. In terms of in vitro serum stability, both the CL2- and CL2A-SN-38 forms of hRS7-SN-38 yielded a $t_{1/2}$, of ~20 hours, which is in contrast to the short $t_{1/2}$ of 12.3 minutes reported for ENZ-2208 (Zhao et al., 2008, Bioconjug Chem 19:849-59), but similar to the 57% release of SN-38 from NK012 under physiological conditions after 24 hours (Koizumi et al., 2006, Cancer Res 66:10048-56).

Treatment of tumor-bearing mice with hRS7-SN-38 (either with CL2-SN-38 or CL2A-SN-38) significantly inhibited tumor growth in 5 different tumor models. In 4 of them, tumor regressions were observed, and in the case of Calu-3, all mice receiving the highest dose of hRS7-SN-38 were tumor-free at the conclusion of study. Unlike in humans, irinotecan is very efficiently converted to SN-38 by a plasma esterase in mice, with a greater than 50% conversion rate, and yielding higher efficacy in mice than in humans (Morton et al., 2000, Cancer Res 60:4206-10; Furman et al., 1999, J Clin Oncol 17:1815-24). When irinotecan was administered at 10-fold higher or equivalent SN-38 levels, hRS7-SN-38 was significantly better in controlling tumor growth. Only when irinotecan was administered at its MTD of 24 mg/kg q2d×5 (37.5-fold more SN-38) did it equal the effectiveness of hRS7-SN-38. In patients, we would expect this advantage to favor hRS7-CL2A-SN-38 even more, because the bioconversion of irinotecan would be substantially lower.

We also showed in some antigen-expressing cell lines, such as SK-MES-1, that using an antigen-binding ADC does not guarantee better therapeutic responses than a nonbinding, irrelevant conjugate. This is not an unusual or unexpected finding. Indeed, the nonbinding SN-38 conjugates mentioned earlier enhance therapeutic activity when compared to irinotecan, and so an irrelevant IgG-SN-38 conjugate is expected to have some activity. This is related to the fact that tumors have immature, leaky vessels that allow the passage of macromolecules better than normal tissues (Jain, 1994, Sci Am 271:58-61). With our conjugate, 50% of the SN-38 will be released in ~13 hours when the pH is lowered to a level mimicking lysosomal levels (e.g., pH 5.3 at 37° C.; data not shown), whereas at the neutral pH of serum, the release rate is reduced nearly 2-fold. If an irrelevant conjugate enters an acidic tumor microenvironment, it is expected to release some SN-38 locally. Other factors, such as tumor physiology and innate sensitivities to the drug, will also play a role in defining this "baseline" activity. However, a specific conjugate with a longer residence time should have enhanced potency over this baseline response as long as there is ample antigen to capture the specific antibody. Biodistribution studies in the SK-MES-1 model also showed that if tumor antigen becomes saturated as a consequence of successive dosing, tumor uptake of the specific conjugate is reduced, which yields therapeutic results similar to that found with an irrelevant conjugate.

Although it is challenging to make direct comparisons between our ADC and the published reports of other SN-38 delivery agents, some general observations can be made. In our therapy studies, the highest individual dose was 0.4 mg/kg of SN-38. In the Calu-3 model, only 4 injections were given for a total cumulative dose of 1.6 mg/kg SN-38 or 32 μg SN-38 in a 20 g mouse. Multiple studies with ENZ-2208 were done using its MTD of 10 mg/kg×5 (Sapra et al., 2008, Clin Cancer Res 14:1888-96; Pastorini et al., 2010, Clin Cancer Res 16:4809-21), and preclinical studies with NK012 involved its MTD of 30 mg/kg×3 (Koizumi et al., 2006, Cancer Res 66:10048-56). Thus, significant antitumor effects were obtained with hRS7-SN-38 at 30-fold and 55-fold less SN-38 equivalents than the reported doses in ENZ-2208 and NK012, respectively. Even with 10-fold less hRS7 ADC (0.04 mg/kg), significant antitumor effects were observed, whereas lower doses of ENZ-2208 were not presented, and when the NK012 dose was lowered 4-fold to 7.5 mg/kg, efficacy was lost (Koizumi et al., 2006, Cancer Res 66:10048-56). Normal mice showed no acute toxicity with a cumulative dose over 1 week of 24 mg/kg SN-38 (1,500 mg/kg of the conjugate), indicating that the MTD was higher. Thus, tumor-bearing animals were effectively treated with 7.5- to 15-fold lower amounts of SN-38 equivalents.

Biodistribution studies revealed the hRS7-CL2A-SN-38 had similar tumor uptake as the parental hRS7 IgG, but cleared substantially faster with 2-fold higher hepatic uptake, which may be due to the hydrophobicity of SN-38. With the ADC being cleared through the liver, hepatic and gastrointestinal toxicities were expected to be dose limiting. Although mice had evidence of increased hepatic transaminases, gastrointestinal toxicity was mild at best, with only transient loss in weight and no abnormalities noted upon histopathologic examination. Interestingly, no hematological toxicity was noted. However, monkeys showed an identical toxicity profile as expected for irinotecan, with gastrointestinal and hematological toxicity being dose-limiting.

Because Trop-2 recognized by hRS7 is not expressed in mice, it was important to perform toxicity studies in monkeys that have a similar tissue expression of Trop-2 as humans. Monkeys tolerated 0.96 mg/kg/dose (~12 mg/m$^2$) with mild and reversible toxicity, which extrapolates to a human dose of ~0.3 mg/kg/dose (~11 mg/m$^2$). In a Phase I clinical trial of NK012, patients with solid tumors tolerated 28 mg/m$^2$ of SN-38 every 3 weeks with Grade 4 neutropenia as dose-limiting toxicity (DLT; Hamaguchi et al., 2010, Clin Cancer Res 16:5058-66). Similarly, Phase I clinical trials with ENZ-2208 revealed dose-limiting febrile neutropenia, with a recommendation to administer 10 mg/m$^2$ every 3 weeks or 16 mg/m$^2$ if patients were administered G-CSF (Kurzrock et al., *AACR-NCI-EORTC International Conference on Molecular Targets and Cancer Therapeutics*; 2009 Nov. 15-19; Boston, Mass.; Poster No C216; Patnaik et al., *AACR-NCI-EORTC International Conference on Molecular Targets and Cancer Therapeutics*; 2009 Nov. 15-19; Boston, Mass.; Poster No C221). Because monkeys tolerated a cumulative human equivalent dose of 22 mg/m$^2$, it appears that even though hRS7 binds to a number of normal tissues, the MTD for a single treatment of the hRS7 ADC could be similar to that of the other nontargeting SN-38 agents. Indeed, the specificity of the anti-Trop-2 antibody did not appear to play a role in defining the DLT, because the toxicity profile was similar to that of irinotecan. More importantly, if antitumor activity can be achieved in humans as in mice that responded with human equivalent dose of just at 0.03 mg SN-38 equivalents/kg/dose, then significant antitumor responses may be realized clinically.

In conclusion, toxicology studies in monkeys, combined with in vivo human cancer xenograft models in mice, have indicated that this ADC targeting Trop-2 is an effective therapeutic in several tumors of different epithelial origin.

Example 7

Anti-Trop-2 ADC Comprising hRS7 and Paclitaxel

A new antibody-drug conjugate (ADC) was made by conjugating paclitaxel (TAXOL®) to the hRS7 anti-human Trop-2 antibody (hRS7-paclitaxel). The final product had a mean drug to antibody substitution ratio of 2.2. This ADC was tested in vitro using two different Trop-2-postive cell lines as targets: BxPC-3 (human pancreatic adenocarcinoma) and MDA-MB-468 (human triple negative breast carcinoma). One day prior to adding the ADC, cells were harvested from tissue culture and plated into 96-well plates at 2000 cells per well. The next day cells were exposed to free paclitaxel ($6.1 \times 10^{-11}$ to $4 \times 10^{-6}$ M) or the drug-equivalent of hRS7-paclitaxel. For comparison, hRS7-SN-38 and free SN-38 were also tested at a range of $3.84 \times 10^{-12}$ to $2.5 \times 10^{-7}$ M. Plates were incubated at 37° C. for 96 h. After this incubation period, an MTS substrate was added to all of the plates and read for color development at half-hour intervals until untreated control wells had an OD$_{492nm}$ reading of approximately 1.0. Growth inhibition was measured as a percent of growth relative to untreated cells using Microsoft Excel and Prism software (non-linear regression to generate sigmoidal dose response curves which yield $IC_{50}$-values).

Figure 15:
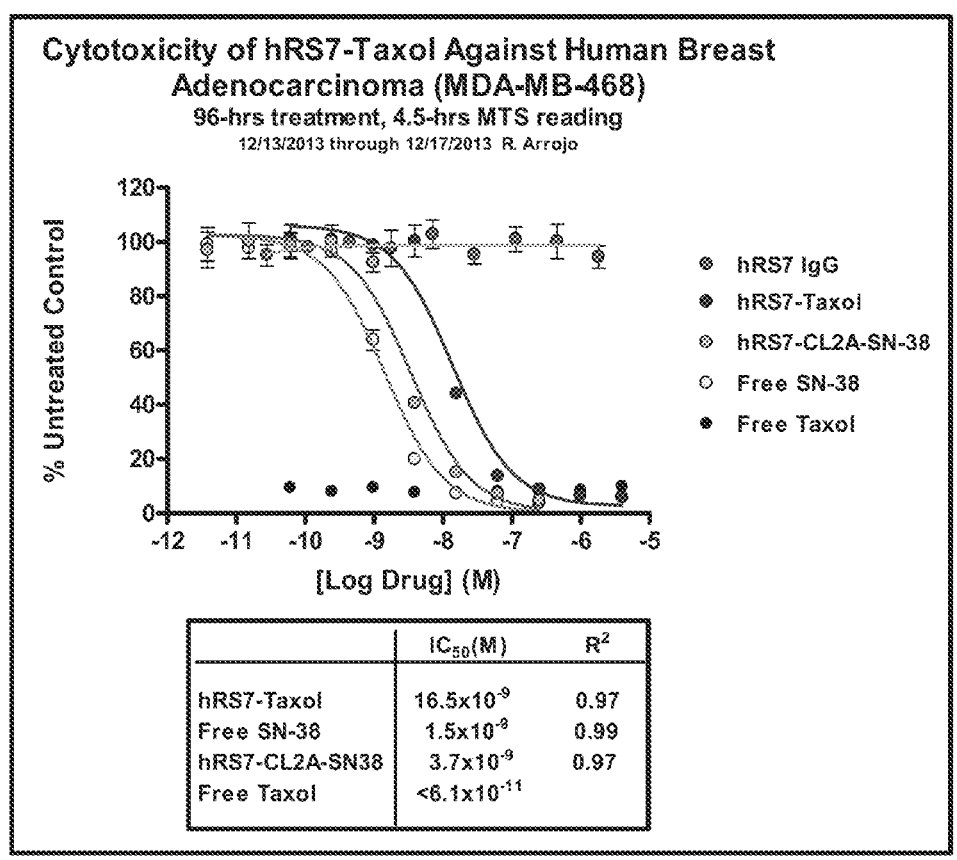
FIG. 15. In vitro efficacy of anti-Trop-2-paclitaxel ADC against MDA-MB-468 human breast adenocarcinoma.
Figure 16:
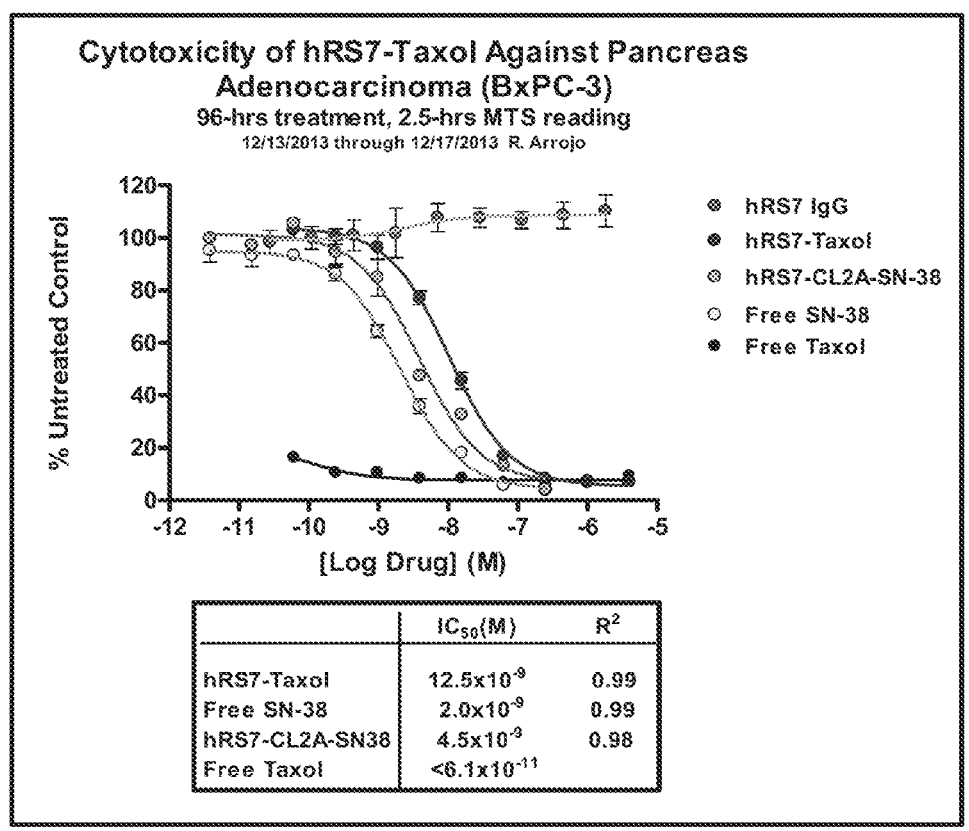
FIG. 16. In vitro efficacy of anti-Trop-2-paclitaxel ADC against BxPC-3 human pancreatic adenocarcinoma.

The hRS7-paclitaxel ADC exhibited cytotoxic activity in the MDA-MB-468 breast cell line (FIG. 15), with an $IC_{50}$-value approximately 4.5-fold higher than hRS7-SN-38. The free paclitaxel was much more potent than the free SN-38 (FIG. 15). While the $IC_{50}$ for free SN-38 was $1.54 \times 10^{-9}$ M, the $IC_{50}$ for free paclitaxel was less than $6.1 \times 10^{-11}$ M. Similar results were obtained for the BxPC-3 pancreatic cell line (FIG. 16) in which the hRS7-paclitaxel ADC had an $IC_{50}$-value approximately 2.8-fold higher than the hRS7-SN-38 ADC. These results show the efficacy of anti-Trop-2 conjugated paclitaxel in vitro, with $IC_{50}$-values in the nanomolar range, similar to the hRS7-SN-38 ADC.

Example 8

Cell Binding Assay of Anti-Trop-2 Antibodies

Two different murine monoclonal antibodies against human Trop-2 were obtained for ADC conjugation. The first, 162-46.2, was purified from a hybridoma (ATCC, HB-187) grown up in roller-bottles. A second antibody, MAB650, was purchased from R&D Systems (Minneapolis, Minn.). For a comparison of binding, the Trop-2 positive human gastric carcinoma, NCI-N87, was used as the target. Cells ($1.5 \times 10^5$/well) were plated into 96-well plates the day before the binding assay. The following morning, a dose/response curve was generated with 162-46.2, MAB650, and murine RS7 (0.03 to 66 nM). These primary antibodies were incubated with the cells for 1.5 h at 4° C. Wells were washed and an anti-mouse-HRP secondary antibody was added to all the wells for 1 h at 4° C. Wells are washed again followed by the addition of a luminescence substrate. Plates were read using Envision plate reader and values are reported as relative luminescent units.

All three antibodies had similar $K_D$-values of 0.57 nM for RS7, 0.52 nM for 162-46.2 and 0.49 nM for MAB650. However, when comparing the maximum binding ($B_{max}$) of 162-46.2 and MAB650 to RS7 they were reduced by 25% and 50%, respectively ($B_{Max}$ 11,250 for RS7, 8,471 for 162-46.2 and 6,018 for MAB650) indicating different binding properties in comparison to RS7.

Example 9

Cytotoxicity of Anti-Trop-2 ADC (MAB650-SN-38)

A novel anti-Trop-2 ADC was made with SN-38 and MAB650, yielding a mean drug to antibody substitution ratio of 6.89. Cytotoxicity assays were performed to compare the MAB650-SN-38 and hRS7-SN-38 ADCs using two different human pancreatic adenocarcinoma cell lines (BxPC-3 and Capan-1) and a human triple negative breast carcinoma cell line (MDA-MB-468) as targets.

One day prior to adding the ADCs, cells were harvested from tissue culture and plated into 96-well plates. The next day cells were exposed to hRS7-SN-38, MAB650-SN-38, and free SN-38 at a drug range of $3.84 \times 10^{-12}$ to $2.5 \times 10^{-7}$ M. Unconjugated MAB650 was used as a control at protein equivalent doses as the MAB650-SN-38. Plates were incubated at 37° C. for 96 h. After this incubation period, an MTS substrate was added to all of the plates and read for color development at half-hour intervals until an $OD_{492nm}$ of approximately 1.0 was reached for the untreated cells. Growth inhibition was measured as a percent of growth relative to untreated cells using Microsoft Excel and Prism software (non-linear regression to generate sigmoidal dose response curves which yield $IC_{50}$-values.

Figure 17B:
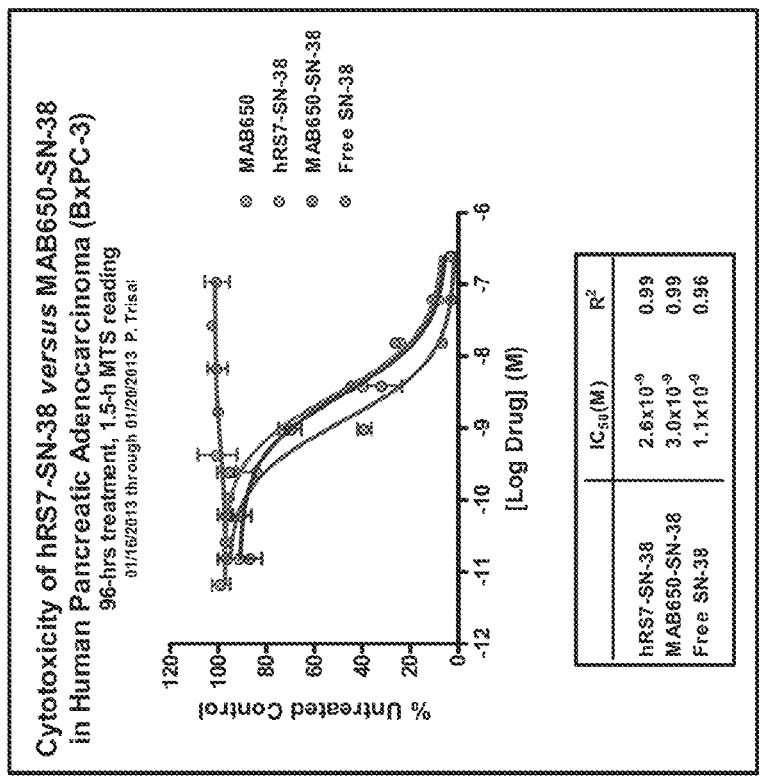
FIG. 17B. Comparison of in vitro efficacy of anti-Trop-2 ADCs (hRS7-SN-38 versus MAB650-SN-38) in BxPC-3 human pancreatic adenocarcinoma.
Figure 17A:
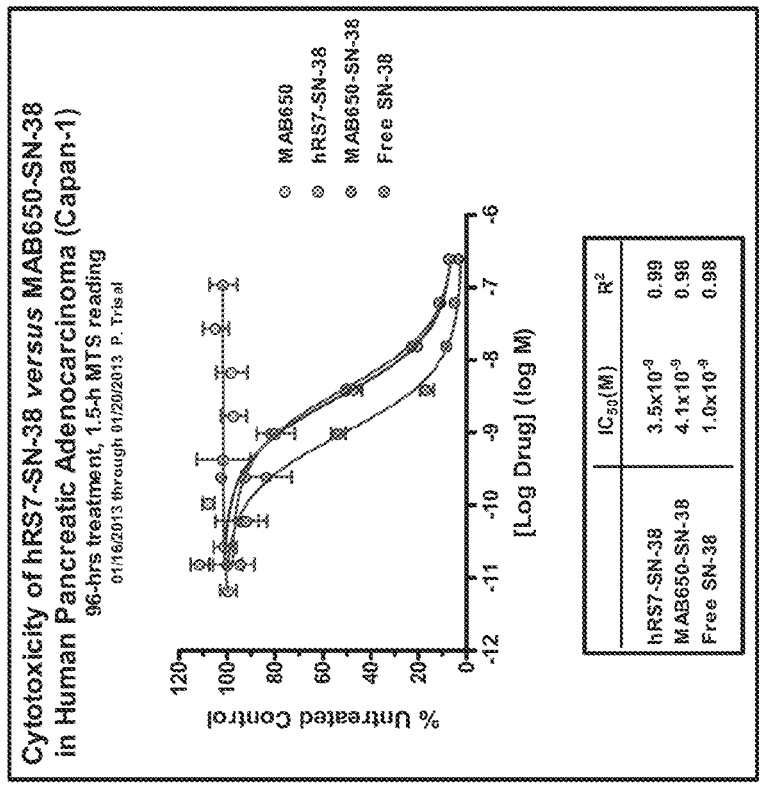
FIG. 17A. Comparison of in vitro efficacy of anti-Trop-2 ADCs (hRS7-SN-38 versus MAB650-SN-38) in Capan-1 human pancreatic adenocarcinoma.
Figure 17C:
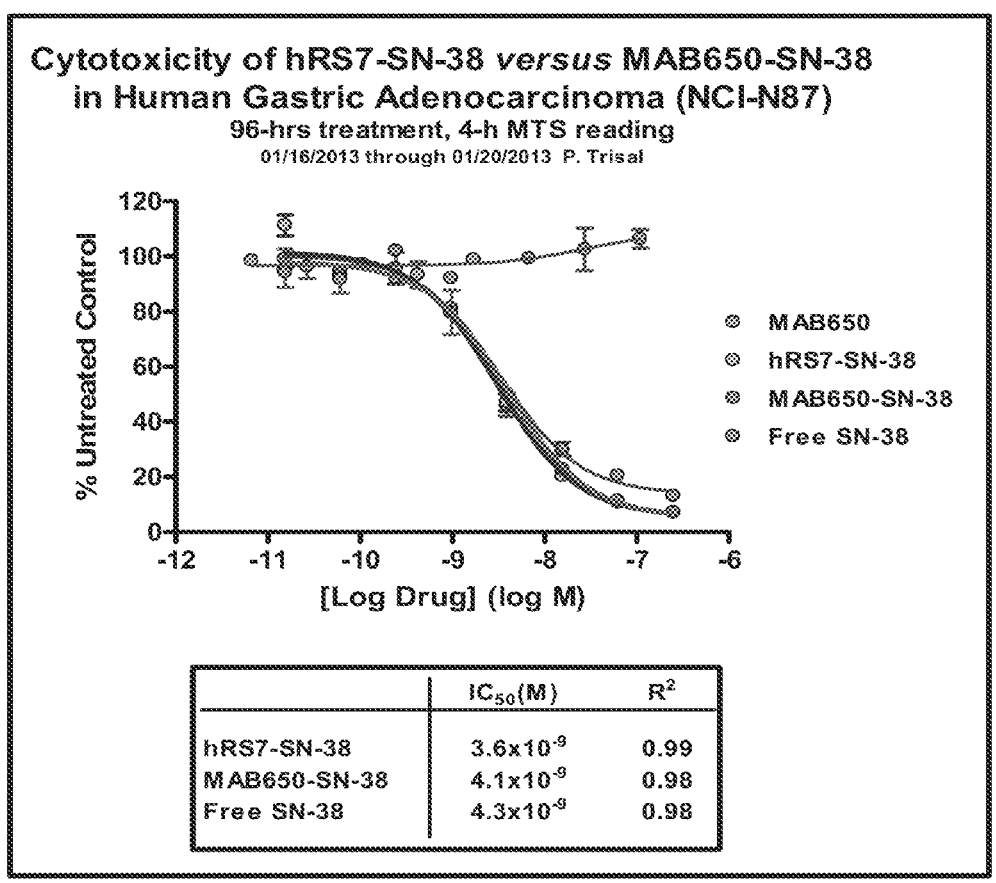
FIG. 17C. Comparison of in vitro efficacy of anti-Trop-2 ADCs (hRS7-SN-38 versus MAB650-SN-38) in NCI-N87 human gastric adenocarcinoma.

As shown in FIG. 17, hRS7-SN-38 and MAB650-SN-38 had similar growth-inhibitory effects with $IC_{50}$-values in the low nM range which is typical for SN-38-ADCs in these cell lines. In the human Capan-1 pancreatic adenocarcinoma cell line (FIG. 17A), the hRS7-SN-38 ADC showed an $IC_{50}$ of 3.5 nM, compared to 4.1 nM for the MAB650-SN-38 ADC and 1.0 nM for free SN-38. In the human BxPC-3 pancreatic adenocarcinoma cell line (FIG. 17B), the hRS7-SN-38 ADC showed an $IC_{50}$ of 2.6 nM, compared to 3.0 nM for the MAB650-SN-38 ADC and 1.0 nM for free SN-38. In the human NCI-N87 gastric adenocarcinoma cell line (FIG. 17C), the hRS7-SN-38 ADC showed an $IC_{50}$ of 3.6 nM, compared to 4.1 nM for the MAB650-SN-38 ADC and 4.3 nM for free SN-38.

In summary, in these in vitro assays, the SN-38 conjugates of two anti-Trop-2 antibodies, hRS7 and MAB650, showed equal efficacies against several tumor cell lines, which was similar to that of free SN-38. Because the targeting function of the anti-Trop-2 antibodies would be a much more significant factor in vivo than in vitro, the data support that anti-Trop-2-SN-38 ADCs as a class would be highly efficacious in vivo, as demonstrated in the Examples above for hRS7-SN-38.

Example 10

Cytotoxicity of Anti-Trop-2 ADC (162-46.2-SN-38)

A novel anti-Trop-2 ADC was made with SN-38 and 162-46.2, yielding a drug to antibody substitution ratio of 6.14. Cytotoxicity assays were performed to compare the 162-46.2-SN-38 and hRS7-SN-38 ADCs using two different Trop-2-positive cell lines as targets, the BxPC-3 human pancreatic adenocarcinoma and the MDA-MB-468 human triple negative breast carcinoma.

One day prior to adding the ADC, cells were harvested from tissue culture and plated into 96-well plates at 2000 cells per well. The next day cells were exposed to hRS7-SN-38, 162-46.2-SN-38, or free SN-38 at a drug range of $3.84 \times 10^{-12}$ to $2.5 \times 10^{-7}$ M. Unconjugated 162-46.2 and hRS7 were used as controls at the same protein equivalent doses as the 162-46.2-SN-38 and hRS7-SN-38, respectively. Plates were incubated at 37° C. for 96 h. After this incubation period, an MTS substrate was added to all of the plates and read for color development at half-hour intervals until untreated control wells had an $OD_{492nm}$ reading of approximately 1.0. Growth inhibition was measured as a percent of growth relative to untreated cells using Microsoft Excel and Prism software (non-linear regression to generate sigmoidal dose response curves which yield $IC_{50}$-values).

Figure 18B:
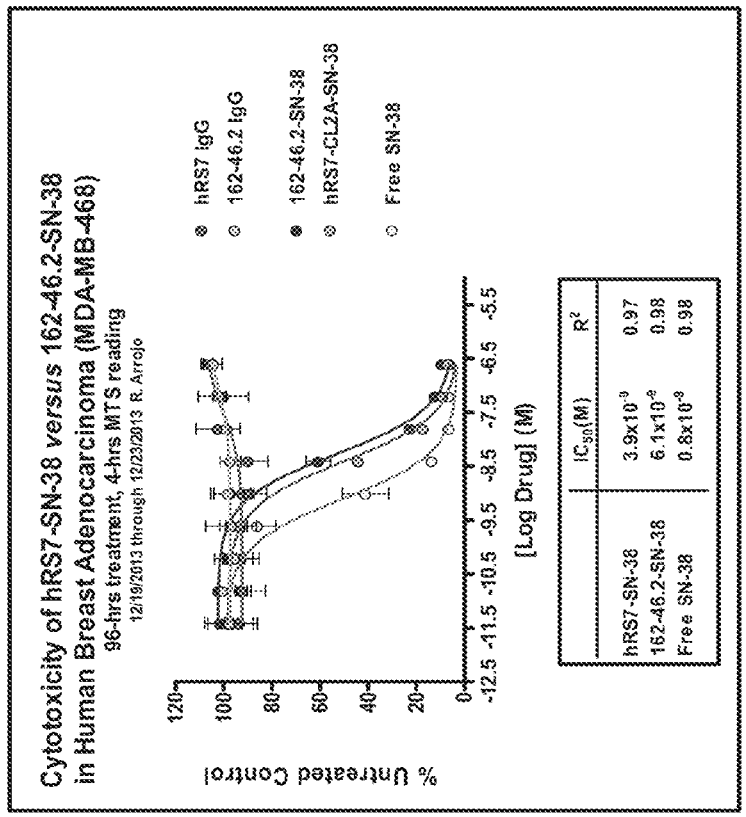
FIG. 18B. Comparison of cytotoxicity of naked or SN-38 conjugated hRS7 vs. 162-46.2 antibodies in MDA-MB-468 human breast adenocarcinoma.
Figure 18A:
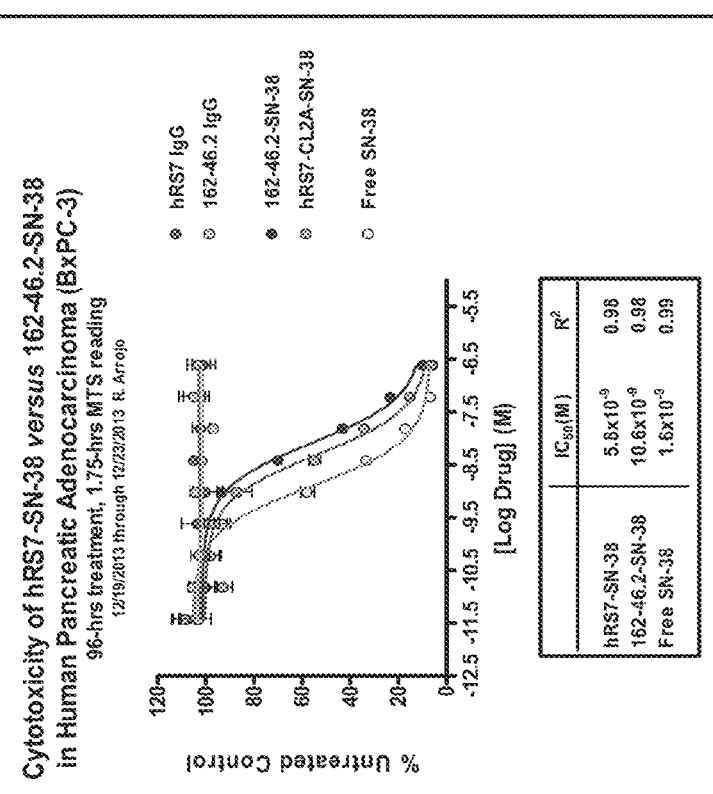
FIG. 18A. Comparison of cytotoxicity of naked or SN-38 conjugated hRS7 vs. 162-46.2 antibodies in BxPC-3 human pancreatic adenocarcinoma.

As shown in FIG. 18A and FIG. 18B, the 162-46.2-SN-38 ADC had a similar $IC_{50}$-values when compared to hRS7-SN-38. When tested against the BxPC-3 human pancreatic adenocarcinoma cell line (FIG. 18A), hRS7-SN-38 had an $10_{50}$ of 5.8 nM, compared to 10.6 nM for 162-46.2-SN-38 and 1.6 nM for free SN-38. When tested against the MDA-MB-468 human breast adenocarcinoma cell line (FIG. 18B), hRS7-SN-38 had an $IC_{50}$ of 3.9 nM, compared to 6.1 nM for 162-46.2-SN-38 and 0.8 nM for free SN-38. The free antibodies alone showed little cytotoxicity to either Trop-2 positive cancer cell line.

In summary, comparing the efficacies in vitro of three different anti-Trop-2 antibodies conjugated to the same cytotoxic drug, all three ADCs exhibited equivalent cytotoxic effects against a variety of Trop-2 positive cancer cell lines. These data support that the class of anti-Trop-2 antibodies, incorporated into drug-conjugated ADCs, are effective anti-cancer therapeutic agents for Trop-2 expressing solid tumors.

Example 11

Clinical Trials With IMMU-132 Anti-Trop-2 ADC Comprising hRS7 Antibody Conjugated to SN-38

Summary

The present Example reports results from a phase I clinical trial and ongoing phase II extension with IMMU-132, an ADC of the internalizing, humanized, hRS7 anti-Trop-2 antibody conjugated by a pH-sensitive linker to SN-38 (mean drug-antibody ratio=7.6). Trop-2 is a type I transmembrane, calcium-transducing, protein expressed at high density ($\sim 1\times 10^5$), frequency, and specificity by many human carcinomas, with limited normal tissue expression. Preclinical studies in nude mice bearing Capan-1 human pancreatic tumor xenografts have revealed IMMU-132 is capable of delivering as much as 120-fold more SN-38 to tumor than derived from a maximally tolerated irinotecan therapy.

The present Example reports the initial Phase I trial of 25 patients who had failed multiple prior therapies (some including topoisomerase-I/II inhibiting drugs), and the ongoing Phase II extension now reporting on 69 patients, including in colorectal (CRC), small-cell and non-small cell lung (SCLC, NSCLC, respectively), triple-negative breast (TNBC), pancreatic (PDC), esophageal, and other cancers.

As discussed in detail below, Trop-2 was not detected in serum, but was strongly expressed ($\geq 2^+$) in most archived tumors. In a 3+3 trial design, IMMU-132 was given on days 1 and 8 in repeated 21-day cycles, starting at 8 mg/kg/dose, then 12 and 18 mg/kg before dose-limiting neutropenia. To optimize cumulative treatment with minimal delays, phase II is focusing on 8 and 10 mg/kg (n=30 and 14, respectively). In 49 patients reporting related AE at this time, neutropenia ≥G3 occurred in 28% (4% G4). Most common non-hematological toxicities initially in these patients have been fatigue (55%; ≥G3=9%), nausea (53%; ≥G3=0%), diarrhea (47%; ≥G3=9%), alopecia (40%), and vomiting (32%; ≥G3=2%). Homozygous UGT1A1*28/*28 was found in 6 patients, 2 of whom had more severe hematological and GI toxicities. In the Phase I and the expansion phases, there are now 48 patients (excluding PDC) who are assessable by RECIST/CT for best response. Seven (15%) of the patients had a partial response (PR), including patients with CRC (N=1), TNBC (N=2), SCLC (N=2), NSCLC (N=1), and esophageal cancers (N=1), and another 27 patients (56%) had stable disease (SD), for a total of 38 patients (79%) with disease response; 8 of 13 CT-assessable PDC patients (62%) had SD, with a median time to progression (TTP) of 12.7 wks compared to 8.0 weeks in their last prior therapy. The TTP for the remaining 48 patients is 12.6+ wks (range 6.0 to 51.4 wks). Plasma CEA and CA19-9 correlated with responses. No anti-hRS7 or anti-SN-38 antibodies were detected despite dosing over months. The conjugate cleared from the serum within 3 days, consistent with in vivo animal studies where 50% of the SN-38 was released daily, with >95% of the SN-38 in the serum being bound to the IgG in a non-glucoronidated form, and at concentrations as much as 100-fold higher than SN-38 reported in patients given irinotecan. These results show that the hRS7-SN-38-containing ADC is therapeutically active in metastatic solid cancers, with manageable diarrhea and neutropenia.

Pharmacokinetics

Two ELISA methods were used to measure the clearance of the IgG (capture with anti-hRS7 idiotype antibody) and the intact conjugate (capture with anti-SN-38 IgG/probe with anti-hRS7 idiotype antibody). SN-38 was measured by HPLC. Total IMMU-132 fraction (intact conjugate) cleared more quickly than the IgG (not shown), reflecting known gradual release of SN-38 from the conjugate. HPLC determination of SN-38 (Unbound and TOTAL) showed >95% the SN-38 in the serum was bound to the IgG. Low concentrations of SN-38G suggest SN-38 bound to the IgG is protected from glucoronidation. Comparison of ELISA for conjugate and SN-38 HPLC revealed both overlap, suggesting the ELISA is a surrogate for monitoring SN-38 clearance.

A summary of the dosing regiment and patient poll is provided in Table 7.

TABLE 7

| Clinical Trial Parameters | |
| --- | --- |
| Dosing regimen | Once weekly for 2 weeks administered every 21 days for up to 8 cycles. In the initial enrollment, the planned dose was delayed and reduced if ≥G2 treatment-related toxicity; protocol was amended to dose delay and reduction only in the event of ≥G3 toxicity. |
| Dose level cohorts | 8, 12, 18 mg/kg; later reduced to an intermediate dose level of 10 mg/kg. |
| Cohort size | Standard Phase I [3 + 3] design; expansion includes 15 patients in select cancers. |
| DLT | G4 ANC ≥ 7 d; ≥G3 febrile neutropenia of any duration; G4 Plt ≥ 5 d; G4 Hgb; Grade 4 N/V/D any duration/G3 N/V/D for >48 h; G3 infusion-related reactions; related ≥G3 non-hematological toxicity. |
| Maximum Acceptable Dose (MAD) | Maximum dose where ≥2/6 patients tolerate $1^{st}$ 21-d cycle w/o delay or reduction or ≥G3 toxicity. |
| Patients | Metastatic colorectal, pancreas, gastric, esophageal, lung (NSCLC, SCLC), triple-negative breast (TNBC), prostate, ovarian, renal, urinary bladder, head/neck, hepatocellular. Refractory/relapsed after standard treatment regimens for metastatic cancer. Prior irinotecan-containing therapy NOT required for enrollment. No bulky lesion >5 cm. Must be 4 weeks beyond any major surgery, and 2 weeks beyond radiation or chemotherapy regimen. Gilbert's disease or known CNS metastatic disease are excluded. |

Clinical Trial Status

A total of 69 patients (including 25 patients in Phase I) with diverse metastatic cancers having a median of 3 prior therapies were reported. Eight patients had clinical progression and withdrew before CT assessment. Thirteen CT-assessable pancreatic cancer patients were separately reported. The median TTP (time to progression) in PDC patients was 11.9 wks (range 2 to 21.4 wks) compared to median 8 wks TTP for the preceding last therapy.

Figure 19:
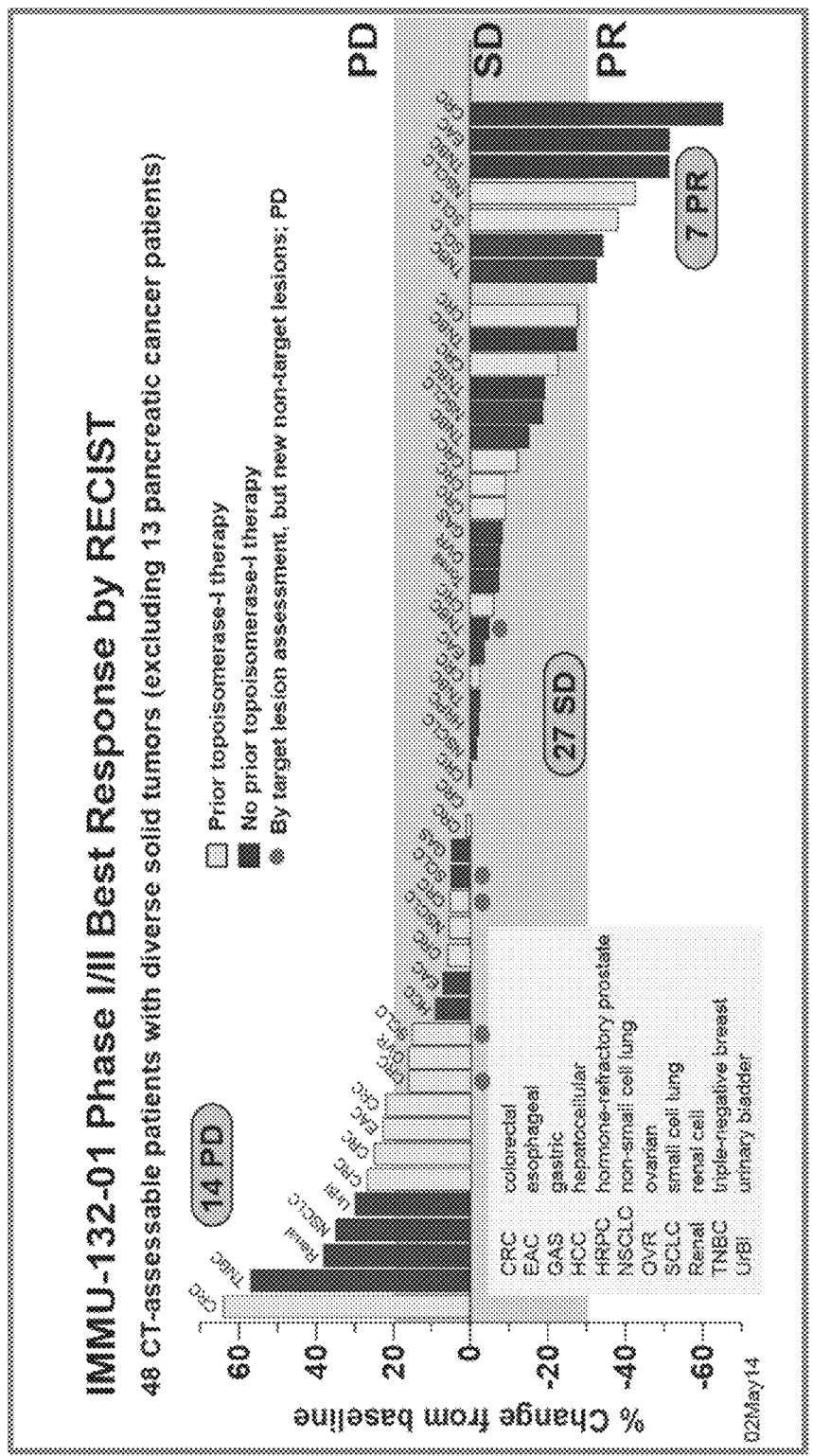
FIG. 19. IMMU-132 phase I/II data for best response by RECIST criteria.
Figure 20:
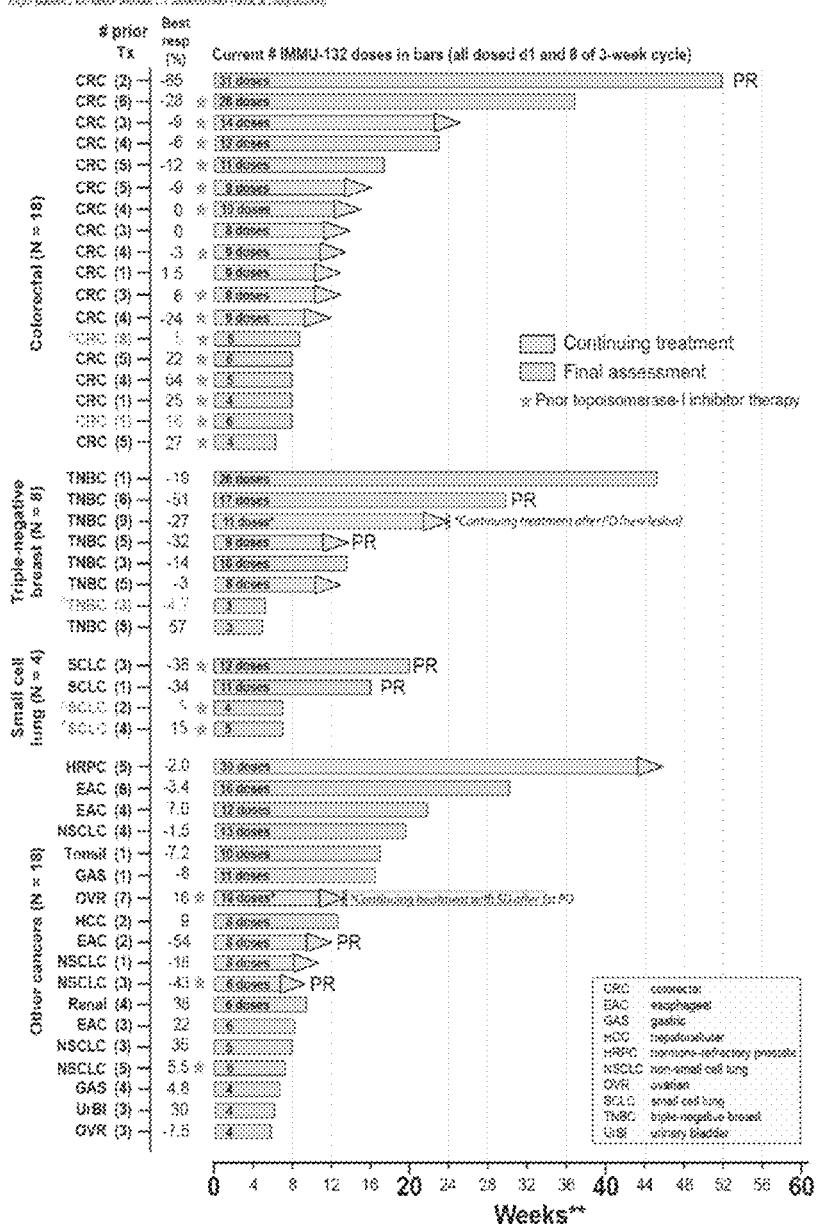
FIG. 20. IMMU-132 phase I/II data for time to progression and best response (RECIST).

A total of 48 patients with diverse cancers had at least 1 CT-assessment from which Best Response (FIG. 19) and Time to Progression (TTP; FIG. 20) were determined. To summarize the Best Response data, of 8 assessable patients with TNBC (triple-negative breast cancer), there were 2 PR (partial response), 4 SD (stable disease) and 2 PD (progressive disease) for a total response [PR+SD] of 6/8 (75%). For SCLC (small cell lung cancer), of 4 assessable patients there were 2 PR, 0 SD and 2 PD for a total response of 2/4 (50%). For CRC (colorectal cancer), of 18 assessable patients there were 1 PR, 11 SD and 6 PD for a total response of 12/18 (67%). For esophageal cancer, of 4 assessable patients there were 1 PR, 2 SD and 1 PD for a total response of 3/4 (75%). For NSCLC (non-small cell lung cancer), of 5 assessable patients there were 1 PR, 3 SD and 1 PD for a total response of 4/5 (80%). Over all patients treated, of 48 assessable patients there were 7 PR, 27 SD and 14 PD for a total response of 34/48 (71%). These results demonstrate that the anti-Trop-2 ADC (hRS7-SN-38) showed significant clinical efficacy against a wide range of solid tumors in human patients.

The reported side effects of therapy (adverse events) are summarized in Table 8. As apparent from the data of Table 8, the therapeutic efficacy of hRS7-SN-38 was achieved at dosages of ADC showing an acceptably low level of adverse side effects.

TABLE 8

Related Adverse Events Listing for IMMU-132-01
Criteria: Total ≥10% or ≥Grade 3

| | N = 47 patients | | |
|---|---|---|---|
| | TOTAL | Grade 3 | Grade 4 |
| Fatigue | 55% | 4 (9%) | 0 |
| Nausea | 53% | 0 | 0 |
| Diarrhea | 47% | 4 (9%) | 0 |
| Neutropenia | 43% | 11 (24%) | 2 (4%) |
| Alopecia | 40% | — | — |
| Vomiting | 32% | 1 (2%) | 0 |
| Anemia | 13% | 2 (4%) | 0 |
| Dysgeusia | 15% | 0 | 0 |
| Pyrexia | 13% | 0 | 0 |
| Abdominal pain | 11% | 0 | 0 |
| Hypokalemia | 11% | 1 (2%) | 0 |
| WBC Decrease | 6% | 1 (2%) | 0 |
| Febrile Neutropenia | 6% | 1 (2%) | 2 (4%) |
| Deep vein thrombosis | 2% | 1 (2%) | 0 |

Grading by CTCAE v 4.0

Exemplary partial responses to the anti-Trop-2 ADC were confirmed by CT data (not shown). As an exemplary PR in CRC, a 62 year-old woman first diagnosed with CRC underwent a primary hemicolectomy. Four months later, she had a hepatic resection for liver metastases and received 7 mos of treatment with FOLFOX and 1 mo 5FU. She presented with multiple lesions primarily in the liver (3+Trop-2 by immunohistology), entering the hRS7-SN-38 trial at a starting dose of 8 mg/kg about 1 year after initial diagnosis. On her first CT assessment, a PR was achieved, with a 37% reduction in target lesions (not shown). The patient continued treatment, achieving a maximum reduction of 65% decrease after 10 months of treatment (not shown) with decrease in CEA from 781 ng/mL to 26.5 ng/mL), before progressing 3 months later.

As an exemplary PR in NSCLC, a 65 year-old male was diagnosed with stage IIIB NSCLC (sq. cell). Initial treatment of caboplatin/etoposide (3 mo) in concert with 7000 cGy XRT resulted in a response lasting 10 mo. He was then started on Tarceva maintenance therapy, which he continued until he was considered for IMMU-132 trial, in addition to undergoing a lumbar laminectomy. He received first dose of IMMU-132 after 5 months of Tarceva, presenting at the time with a 5.6 cm lesion in the right lung with abundant pleural effusion. He had just completed his 6$^{th}$ dose two months later when the first CT showed the primary target lesion reduced to 3.2 cm (not shown).

As an exemplary PR in SCLC, a 65 year-old woman was diagnosed with poorly differentiated SCLC. After receiving carboplatin/etoposide (Topo-II inhibitor) that ended after 2 months with no response, followed with topotecan (Topo-I inhibitor) that ended after 2 months, also with no response, she received local XRT (3000 cGy) that ended 1 month later. However, by the following month progression had continued. The patient started with IMMU-132 the next month (12 mg/kg; reduced to 6.8 mg/kg; Trop-2 expression 3+), and after two months of IMMU-132, a 38% reduction in target lesions, including a substantial reduction in the main lung lesion occurred (not shown). The patient progressed 3 months later after receiving 12 doses.

These results are significant in that they demonstrate that the anti-Trop-2 ADC was efficacious, even in patients who had failed or progressed after multiple previous therapies.

In conclusion, at the dosages used, the primary toxicity was a manageable neutropenia, with few Grade 3 toxicities. IMMU-132 showed evidence of activity (PR and durable SD) in relapsed/refractory patients with triple-negative breast cancer, small cell lung cancer, non-small cell lung cancer, colorectal cancer and esophageal cancer, including patients with a previous history of relapsing on topoisomerase-I inhibitor therapy. These results show efficacy of the anti-Trop-2 ADC in a wide range of cancers that are resistant to existing therapies.

Example 12

Treatment of Triple Negative Breast Cancer With pro-2-PDox-hRS7 ADC pro-2-PDox-hRS7 ADC is prepared as described in the Examples above. Patients with triple-negative breast cancer who had failed at least two standard therapies receive 3 cycles of 70 mg pro-2-PDox-hRS7 injected i.v. every 3 weeks. Objective responses are observed at this dose level of pro-2-PDox-hRS7, with an average decrease in tumor volume of 35%, after two cycles of therapy. All serum samples evaluated for human anti-hRS7 antibody (HAHA) are negative.

Example 13

Treatment of Metastatic Colon Cancer With pro-2-PDox-hRS7 ADC

A 52-year old man with metastatic colon cancer (3-5 cm diameters) to his left and right liver lobes, as well as a 5 cm metastasis to his right lung, and an elevated blood CEA value of 130 ng/mL, is treated with a 150 mg dose of hRS7 anti-Trop-2 conjugated with pro-2-PDox at 4 drug molecules per IgG, administered by slow intravenous infusion every other week for 4 doses. Upon CT evaluation 8 weeks from treatment begin, a 25% reduction of the total mean diameters of the 3 target lesions is measured, thus constituting a good stable disease response by RECIST1.1 criteria. Repeated courses of therapy continue as his neutropenia normalizes.

Example 14

Treatment of Metastatic Pancreatic Cancer With pro-2-PDox-hRS7 ADC

A 62-year old man with metastatic ductal adenocarcinoma of the pancreas, who has relapsed after prior therapies with FOLFIRINOX followed by Nab-taxol (Abraxane®) plus gemcitabine is given hRS7-pro-2-PDox ADC at a dose of 120 mg every other week for 4 courses, and after a 3-week delay, another course of 2 injections 2 weeks apart are given intravenously. The patient shows some nausea and transient diarrhea with the therapy, and also Grade 3 neutropenia after the first course, which recovers before the second course of therapy. CT measurements made at 8 weeks following start of therapy show an 18% shrinkage of the sum of the 3 target lesions in the liver, as compared to the pretreatment baseline measurements, constituting stable disease by RECIST 1.1 criteria. Also, the patient's CA19-9 blood titer is reduced by 55% from a baseline value of 12,400. His general symptoms of weakness, fatigue and abdominal discomfort also improve considerably, including regaining his appetite and a weight increase of 2 kg during the following 6 weeks.

Example 15

Combining Antibody-Targeted Radiation (Radioimmunotherapy) and Anti-Trop-2-SN-38 ADC Improves Pancreatic Cancer Therapy We previously reported effective anti-tumor activity in nude mice bearing human pancreatic tumors with $^{90}$Y-humanized PAM4 IgG (hPAM4; $^{90}$Y-clivatuzumab tetraxetan) that was enhanced when combined with gemcitabine (GEM) (Gold et al., Int J. Cancer 109:618-26, 2004; Clin Cancer Res 9:3929S-37S, 2003). These studies led to clinical testing of fractionated $^{90}$Y-hPAM4 IgG combined with GEM that is showing encouraging objective responses. While GEM is known for its radiosensitizing ability, alone it is not a very effective therapeutic agent for pancreatic cancer and its dose is limited by hematologic toxicity, which is also limiting for $^{90}$Y-hPAM4 IgG.

As discussed in the Examples above, an anti-Trop-2 ADC composed of hRS7 IgG linked to SN-38 shows anti-tumor activity in various solid tumors. This ADC is very well tolerated in mice (e.g., ≥60 mg), yet just 4.0 mg (0.5 mg, twice-weekly×4) is significantly therapeutic. Trop-2 is also expressed in most pancreatic cancers.

The present study examined combinations of $^{90}$Y-hPAM4 IgG with RS7-SN-38 in nude mice bearing 0.35 cm$^3$ subcutaneous xenografts of the human pancreatic cancer cell line, Capan-1. Mice (n=10) were treated with a single dose of $^{90}$Y-hPAM4 IgG alone (130 µCi, i.e., the maximum tolerated dose (MTD) or 75 with RS7-SN-38 alone (as above), or combinations of the 2 agents at the two $^{90}$Y-hPAM4 dose levels, with the first ADC injection given the same day as the $^{90}$Y-hPAM4. All treatments were tolerated, with ≤15% loss in body weight. Objective responses occurred in most animals, but they were more robust in both of the combination groups as compared to each agent given alone. All animals in the 0.13-mCi $^{90}$Y-hPAM4 IgG+ hRS7-SN-38 group achieved a tumor-free state within 4 weeks, while other animals continued to have evidence of persistent disease. These studies provide the first evidence that combined radioimmunotherapy and ADC enhances efficacy at safe doses.

In the ongoing PAM4 clinical trials, a four week clinical treatment cycle is performed. In week 1, subjects are administered a dose of $^{111}$In-hPAM4, followed at least 2 days later by gemcitabine dose. In weeks 2, 3 and 4, subjects are administered a $^{90}$Y-hPAM4 dose, followed at least 2 days later by gemcitabine (200 mg/m$^2$). Escalation started at 3×6.5 mCi/m$^2$. The maximum tolerated dose in front-line pancreatic cancer patients was 3×15 mCi/m$^2$ (hematologic toxicity is dose-limiting). Of 22 CT-assessable patients, the disease control rate (CR+PR+SD) was 68%, with 5 (23%) partial responses and 10 (45%) having stabilization as best response by RECIST criteria.

Preparation of Antibody-Drug Conjugate (ADC)

The SN-38 conjugated hRS7 antibody was prepared as described above and according to previously described protocols (Moon et al. J Med Chem 2008, 51:6916-6926; Govindan et al., Clin Cancer Res 2009. 15:6052-6061). A reactive bifunctional derivative of SN-38 (CL2A-SN-38) was prepared. The formula of CL2A-SN-38 is (maleimido-[x]-Lys-PABOCO-20-O-SN-38, where PAB is p-aminobenzyl and 'x' contains a short PEG). Following reduction of disulfide bonds in the antibody with TCEP, the CL2A-SN-38 was reacted with reduced antibody to generate the SN-38 conjugated RS7.

$^{90}$Y-hPAM4 is prepared as previously described (Gold et al., Clin Cancer Res 2003, 9:3929S-37S; Gold et al., Int J Cancer 2004, 109:618-26).

Combination RAIT+ADC

The Trop-2 antigen is expressed in most epithelial cancers (lung, breast, prostate, ovarian, colorectal, pancreatic) and hRS7-SN-38 conjugates are being examined in various human cancer-mouse xenograft models. Initial clinical trials with $^{90}$Y-hPAM4 IgG plus radiosensitizing amounts of GEM are encouraging, with evidence of tumor shrinkage or stable disease. However, therapy of pancreatic cancer is very challenging. Therefore, a combination therapy was examined to determine whether it would induce a better response. Specifically, administration of hRS7-SN-38 at effective, yet non-toxic doses was combined with RAIT with $^{90}$Y-hPAM4 IgG.

The results demonstrated that the combination of hRS7-SN-38 with $^{90}$Y-hPAM4 was more effective than either treatment alone, or the sum of the individual treatments (not shown). At a dosage of 75 µCi $^{90}$Y-hPAM4, only 1 of 10 mice was tumor-free after 20 weeks of therapy (not shown), the same as observed with hRS7-SN-38 alone (not shown). However, the combination of hRS7-SN-38 with $^{90}$Y-hPAM4 resulted in 4 of 10 mice that were tumor-free after 20 weeks (not shown), and the remaining subjects showed substantial decrease in tumor volume compared with either treatment alone (not shown). At 130 µCi $^{90}$Y-hPAM4 the difference was even more striking, with 9 of 10 animals tumor-free in the combined therapy group compared to 5 of 10 in the RAIT alone group (not shown). These data demonstrate the synergistic effect of the combination of hRS7-SN-38 with $^{90}$Y-hPAM4. RAIT+ADC significantly improved time to progression and increased the frequency of tumor-free treatment. The combination of ADC with hRS7-SN-38 added to the MTD of RAIT with $^{90}$Y-hPAM4 had minimal additional toxicity, indicated by the % weight loss of the animal in response to treatment (not shown).

The effect of different sequential treatments on tumor survival indicated that the optimal effect is obtained when RAIT is administered first, followed by ADC (not shown). In contrast, when ADC is administered first followed by RAIT, there is a decrease in the incidence of tumor-free animals (not shown). Neither unconjugated hPAM4 nor hRS7 antibodies had anti-tumor activity when given alone (not shown).

Example 16

Conjugation of Bifunctional SN-38 Products to Mildly Reduced Antibodies

The anti-CEACAM5 humanized MAb, hMN-14 (also known as labetuzumab), the anti-CD22 humanized MAb, hLL2 (also known as epratuzumab), the anti-CD20 humanized MAb, hA20 (also known as veltuzumab), the anti-EGP-1 humanized MAb, hRS7, and anti-mucin humanized MAb, hPAM4 (also known as clivatuzumab), were conjugated to SN-38 using a CL2A linker. Each antibody was reduced with dithiothreitol (DTT), used in a 50-to-70-fold molar excess, in 40 mM PBS, pH 7.4, containing 5.4 mM EDTA, at 37° C. (bath) for 45 min. The reduced product was purified by size-exclusion chromatography and/or diafiltration, and was buffer-exchanged into a suitable buffer at pH 6.5. The thiol content was determined by Ellman's assay, and was in the 6.5-to-8.5 SH/IgG range. Alternatively, the antibodies were reduced with Tris (2-carboxyethyl) phosphine (TCEP) in phosphate buffer at pH in the range of 5-7, followed by in situ conjugation. The reduced MAb was reacted with ~10-to-15-fold molar excess of CL2A-SN-38 using DMSO at 7-15% v/v as co-solvent, and incubating for 20 min at ambient temperature. The conjugate was purified by centrifuged SEC, passage through a hydrophobic column, and finally by ultrafiltration-diafiltration. The product was assayed for SN-38 by absorbance at 366 nm and correlating with standard values, while the protein concentration was deduced from absorbance at 280 nm, corrected for spillover of SN-38 absorbance at this wavelength. This way, the SN-38/MAb substitution ratios were determined. The purified conjugates were stored as lyophilized formulations in glass vials, capped under vacuum and stored in a −20° C. freezer. SN-38 molar substitution ratios (MSR) obtained for these conjugates were typically in the 5-to-7 range Example 17

Therapy of Advanced Colon Cancer Patient Refractory to Prior Chemo-immunotherapy, Using Only IMMU-130 (Labetuzumab-SN-38)

The patient is a 50-year-old man with a history of stage-IV metastatic colonic cancer, first diagnosed in 2008 and given a colectomy and partial hepatectomy for the primary and metastatic colonic cancers, respectively. He then received chemotherapy, as indicated in FIG. 8, which included irinotecan, oxaliplatin, FOLFIRINOX (5-fluorouracil, leucovorin, irinotecan, oxaliplatin), and bevacizumab, as well as bevacizumab combined with 5-fluorouracil/leucovorin, for almost 2 years. Thereafter, he was given courses of cetuximab, either alone or combined with FOLFIRI (leucovorin, 5-flurouracil, irinotecan) chemotherapy during the next year or more. In 2009, he received radiofrequency ablation therapy to his liver metastasis while under chemo-immunotherapy, and in late 2010 he underwent a wedge resection of his lung metastases, which was repeated a few months later, in early 2011. Despite having chemo-immunotherapy in 2011, new lung metastases appeared at the end of 2011, and in 2012, both lung and liver metastases were visualized. His baseline plasma carcinoembryonic antigen (CEA) titer was 12.5 ng/mL just before undergoing the antibody-drug therapy with IMMU-130. The index lesions chosen by the radiologist for measuring tumor size change by computed tomography were the mid-lobe of the right lung and the liver metastases, both totaling 91 mm as the sum of their longest diameters at the baseline prior to IMMU-130 (anti-CEACAM5-SN-38) therapy.

This patient received doses of 16 mg/kg of IMMU-130 by slow IV infusion every other week for a total of 17 treatment doses. The patient tolerated the therapy well, having only a grade 1 nausea, diarrhea and fatigue after the first treatment, which occurred after treatments 4 and 5, but not therafter, because he received medication for these side-effects. After treatment 3, he did show alopecia (grade 2), which was present during the subsequent therapy. The nausea, diarrhea, and occasional vomiting lasted only 2-3 days, and his fatigue after the first infusion lasted 2 weeks. Otherwise, the patient tolerated the therapy well. Because of the long duration of receiving this humanized (CDR-grafted) antibody conjugated with SN-38, his blood was measured for anti-labetuzumab antibody, and none was detected, even after 16 doses.

The first computed tomography (CT) measurements were made after 4 treatments, and showed a 28.6% change from the sum of the measurements made at baseline, prior to this therapy, in the index lesions. After 8 treatments, this reduction became 40.6%, thus constituting a partial remission according to RECIST criteria. This response was maintained for another 2 months, when his CT measurements indicated that the index lesions were 31.9% less than the baseline measurements, but somewhat higher than the previous decrease of 40.6% measured. Thus, based on careful CT measurements of the index lesions in the lung and liver, this patient, who had failed prior chemotherapy and immunotherapy, including irinotecan (parent molecule of SN-38), showed an objective response to the active metabolite of irinotecan (or camptotechin), SN-38, when targeted via the anti-CEACAM5 humanized antibody, labetuzumab (hMN-14). It was surprising that although irinotecan (CPT-11) acts by releasing SN-38 in vivo, the SN-38 conjugated anti-CEACAM5 antibody proved effective in a colorectal cancer patient by inducing a partial response after the patient earlier failed to respond to his last irinotecan-containing therapy. The patient's plasma CEA titer reduction also corroborated the CT findings: it fell from the baseline level of 12.6 ng/mL to 2.1 ng/mL after the third therapy dose, and was between 1.7 and 3.6 ng/mL between doses 8 and 12. The normal plasma titer of CEA is usually considered to be between 2.5 and 5.0 ng/mL, so this therapy effected a normalization of his CEA titer in the blood.

Example 18

Therapy of a Patient with Advanced Colonic Cancer with IMMU-130

This patient is a 75-year-old woman initially diagnosed with metastatic colonic cancer (Stage IV). She has a right partial hemicolectomy and resection of her small intestine and then receives FOLFOX, FOLFOX+bevacizumab, FOLFIRI+ramucirumab, and FOLFIRI+cetuximab therapies for a year and a half, when she shows progression of disease, with spread of disease to the posterior cul-de-sac, omentum, with ascites in her pelvis and a pleural effusion on the right side of her chest cavity. Her baseline CEA titer just before this therapy is 15 ng/mL. She is given 6 mg/kg IMMU-130 (anti-CEACAM5-SN-38) twice weekly for 2 consecutive weeks, and then one week rest (3-week cycle), for more than 20 doses, which is tolerated very well, without any major hematological or non-hematological toxicities. Within 2 months of therapy, her plasma CEA titer shrinks modestly to 1.3 ng/mL, but at the 8-week evaluation she shows a 21% shrinkage of the index tumor lesions, which increases to a 27% shrinkage at 13 weeks. Surprisingly, the patient's ascites and pleural effusion both decrease (with the latter disappearing) at this time, thus improving the patient's overall status remarkably. The patient continues her investigational therapy.

Example 19

Gastric Cancer Patient with Stage IV Metastatic Disease Treated with IMMU-130

The patient is a 52-year-old male who sought medical attention because of gastric discomfort and pain related to eating for about 6 years, and with weight loss during the past 12 months. Palpation of the stomach area reveals a firm lump which is then gastroscoped, revealing an ulcerous mass at the lower part of his stomach. This is biopsied and diagnosed as a gastric adenocarcinoma. Laboratory testing reveals no specific abnormal changes, except that liver function tests, LDH, and CEA are elevated, the latter being 10.2 ng/mL. The patent then undergoes a total-body PET scan, which discloses, in addition to the gastric tumor, metastatic disease in the left axilla and in the right lobe of the liver (2 small metastases). The patient has his gastric tumor resected, and then has baseline CT measurements of his metastatic tumors. Four weeks after surgery, he receives 3 courses of combination chemotherapy consisting of a regimen of cisplatin and 5-fluorouracil (CF), but does not tolerate this well, so is switched to treatment with docetaxel. It appears that the disease is stabilized for about 4 months, based on CT scans, but then the patient's complaints of further weight loss, abdominal pain, loss of appetite, and extreme fatigue cause repeated CT studies, which show increase in size of the metastases by a sum of 20% and a suspicious lesion at the site of the original gastric resection.

The patient is then given experimental therapy with IMMU-130 (anti-CEACAM5-SN-38) on a weekly schedule of 8 mg/kg. He tolerates this well, but after 3 weeks shows a grade 2 neutropenia and grade 1 diarrhea. His fourth infusion is postponed by one week, and then the weekly infusions are reinstituted, with no evidence of diarrhea or neutropenia for the next 4 injection. The patient then undergoes a CT study to measure his metastatic tumor sizes and to view the original area of gastric resection. The radiologist measures, according to RECIST criteria, a decrease of the sum of the metastatic lesions, compared to baseline prior to IMMU-130 therapy, of 23%. There does not seem to be any clear lesion in the area of the original gastric resection. The patient's CEA titer at this time is 7.2 ng/mL, which is much reduced from the pre-IMMU-130 baseline value of 14.5 ng/mL. The patient continues on weekly IMMU-130 therapy at the same dose of 8.0 mg/kg, and after a total of 13 infusions, his CT studies show that one liver metastasis has disappeared and the sum of all metastatic lesions is decreased by 41%, constituting a partial response by RECIST. The patient's general condition improves and he resumes his usual activities while continuing to receive a maintenance therapy of 8 mg/kg IMMU-130 every third week for another 4 injections. At the last measurement of blood CEA, the value is 4.8 ng/mL, which is within the normal range for a smoker, which is the case for this patient.

Example 20

Therapy of Advanced Metastatic Colon Cancer with Anti-CEACAM5 Immunoconjugate

The patient is a 50-year-old male who fails prior therapies for metastatic colon cancer. The first line of therapy is FOLFIRINOX+AVASTIN (built up in a stepwise manner) starting with IROX (Irinotecan+Oxaliplatin) in the first cycle. After initiating this treatment the patient has a CT that shows decrease in the size of liver metastases. This is followed by surgery to remove tumor tissue. Adjuvant chemotherapy is a continuation of the first line regimen (without the IROX part) that resulted in a transient recurrence-free period. After about a 1 year interval, a CT reveals the recurrence of liver metastases. This leads to the initiation of the second line regimen (FOLFIRI+Cetuximab). Another CT shows a response in liver metastases. Then RF ablation of liver metastases is performed, followed by continuation of adjuvant chemotherapy with FOLFIRINOX+Cetuximab, followed by maintenance Cetuximab for approximately one year. Another CT scan shows no evidence of disease. A further scan shows possible lung nodules, which is confirmed. This leads to a wedge resection of the lung nodules. Subsequently FOLFIRI+Cetuximab is restarted and continued. Later CT scans show both lung and liver metastases.

At the time of administration of the hMN-14-SN-38 immunoconjugate, the patient has advanced metastatic colon cancer, with metastases of both lung and liver, which is unresponsive to irinotecan (camptothecin). The hMN-14-SN-38 immunoconjugate is administered at a dosage of 12 mg/kg, which is repeated every other week. The patient shows a partial response with reduction of metastatic tumors by RECIST criteria.

Of note is that only one patient in this 12 mg/kg (given every other week) cohort shows a grade 2 hematological (neutropenia) and most patients have grade 1 or 2 nausea, vomiting, or alopecia—which are signs of activity of the antibody-drug conjugate, but well tolerated. The effect of the antibody moiety in improved targeting of the camptothecin accounts for the efficacy of the SN-38 moiety in the cancer that had been previously resistant to unconjugated irinotecan.

It will be apparent to those skilled in the art that various modifications and variations can be made to the products, compositions, methods and processes of this invention. Thus, it is intended that the present invention cover such modifications and variations, provided they come within the scope of the appended claims and their equivalents.

What is claimed is:

1. A method of treating cancer comprising administering to a human patient with a Trop-2 positive cancer an immunoconjugate comprising SN-38 conjugated to an anti-Trop-2 antibody or antigen-binding fragment thereof; wherein the cancer is resistant to or relapsed from treatment with irinotecan, wherein the immunoconjugate is administered at a dosage of between 4 mg/kg and 16 mg/kg.

2. The method of claim 1, wherein the dosage is selected from the group consisting of 4 mg/kg, 6 mg/kg, 7 mg/kg, 8 mg/kg, 9 mg/kg, 10 mg/kg, 12 mg/kg, and 16 mg/kg.

3. The method of claim 1, wherein the dosage is between 8 mg/kg to 10 mg/kg.

4. The method of claim 1, wherein the antibody is hRS7 (anti-Trop-2).

5. The method of claim 1, wherein the cancer is a gastrointestinal cancer.

6. The method of claim 5, wherein the cancer is colorectal cancer, esophageal cancer or gastric cancer.

7. The method of claim 1, wherein the cancer is colorectal, lung, stomach, urinary bladder, renal, breast, ovarian, uterine or prostatic cancer.

8. The method of claim 1, wherein the cancer is metastatic.

9. The method of claim 1, wherein the cancer is a solid tumor and the treatment results in a reduction in tumor size of at least 15%, at least 20%, at least 30%, or at least 40%.

10. The method of claim 8, further comprising reducing in size or eliminating the metastases.

11. The method of claim 1, wherein the cancer is refractory to other therapies but responds to the immunoconjugate.

12. The method of claim 1, wherein there is a CL2A linker between the SN-38 and the antibody and the structure of the immunoconjugate is MAb-CL2A-SN-38.

13. The method of claim 1, wherein there are 6 or more SN-38 molecules attached to each antibody molecule.

14. The method of claim 1, wherein there are 6-8 SN-38 molecules attached to each antibody molecule.

15. The method of claim 1, wherein there are 7-8 SN-38 molecules attached to each antibody molecule.

16. The method of claim 1, wherein the antibody is an IgG1 or IgG4 antibody.

17. The method of claim 1, wherein the antibody has an allotype selected from the group consisting of G1m3, G1m3, 1, G1m3,2, G1m3,1,2, nG1m1, nG1m1,2 and Km3 allotypes.

18. The method of claim 1, wherein the immunoconjugate dosage is administered to the human subject once or twice a week on a schedule with a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five weeks off; (vi) four weeks of therapy followed by one, two, three, four or five weeks off; (vii) five weeks of therapy followed by one, two, three, four or five weeks off; and (viii) monthly.

19. The method of claim 18, wherein the cycle is repeated 4, 6, 8, 10, 12, 16 or 20 times.

20. The method of claim 1, wherein the immunoconjugate is administered in combination with one or more therapeutic modalities selected from the group consisting of unconjugated antibodies, radiolabeled antibodies, drug-conjugated antibodies, toxin-conjugated antibodies, gene therapy, chemotherapy, therapeutic peptides, cytokine therapy, oligonucleotides, localized radiation therapy, surgery and interference RNA therapy.

21. The method of claim 20, wherein the drug, toxin or chemotherapeutic agent is selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1,

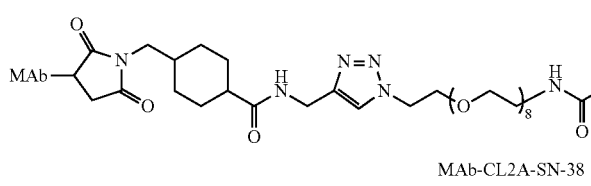

MAb-CL2A-SN-38

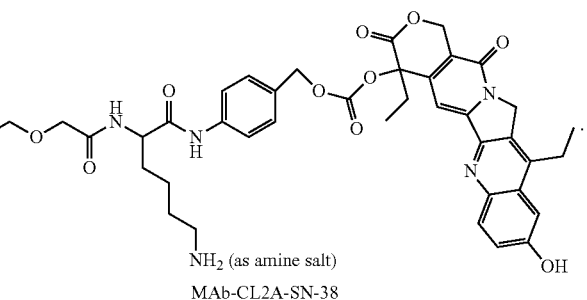

MAb-CL2A-SN-38 busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, crizotinib, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, flavopiridol, floxuridine (FUdR), 3′,5′-O-dioleoyl-FudR (FUdR-dO), fludarabine, flutamide, farnesyl-protein transferase inhibitors, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839.

22. The method of claim 1, wherein the cancer is a metastatic colon cancer and the patient has failed FOLFIRI or FOLFOX chemotherapy prior to administration of the immunoconjugate.

\* \* \* \* \*

UNITED STATES PATENT AND TRADEMARK OFFICE
CERTIFICATE OF CORRECTION

PATENT NO. : 9,492,566 B2
APPLICATION NO. : 14/844772
DATED : November 15, 2016
INVENTOR(S) : Goldenberg et al.

It is certified that error appears in the above-identified patent and that said Letters Patent is hereby corrected as shown below:

In Column 1, below the paragraph ending at Line 16 and above the heading SEQUENCE LISTING, please insert the following heading and text:
--GOVERNMENT SUPPORT
This invention was made with government support under Grant Number CA171388 awarded by the National Institutes of Health. The government has certain rights in the invention.--

Signed and Sealed this
Tenth Day of April, 2018

Andrei Iancu
*Director of the United States Patent and Trademark Office*

SEQUENCE LISTING

<160> NUMBER OF SEQ ID NOS: 114

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Ser Gln Asp Val Ser Ile Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Tyr Arg Tyr Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln His Tyr Ile Thr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Tyr Gly Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Thr Tyr Thr Gly Glu Pro Thr Tyr Thr Asp Asp Phe Lys
1               5                   10                  15

Gly

<210> SEQ ID NO 6
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Gly Gly Phe Gly Ser Ser Tyr Trp Tyr Phe Asp Val
1               5                   10

<210> SEQ ID NO 7
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
            325                 330

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

```
<210> SEQ ID NO 9
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 10
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ile Glu Tyr Leu Ala Lys Gln Ile Val Asp Asn Ala Ile Gln Gln
1               5                   10                  15

Ala

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 13
<211> LENGTH: 50
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 13

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 14
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 16
<211> LENGTH: 51
<212> TYPE: PRT
<213> ORGANISM: Homo sapiens

<400> SEQUENCE: 16

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 17
<211> LENGTH: 54

```
<212> TYPE: PRT
<213> ORGANISM: Homo sapiens

<400> SEQUENCE: 17

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
                20                  25                  30

Pro Met Lys Phe Leu Arg Glu His Phe Glu Lys Leu Glu Lys Glu Glu
            35                  40                  45

Asn Arg Gln Ile Leu Ala
        50

<210> SEQ ID NO 18
<211> LENGTH: 44
<212> TYPE: PRT
<213> ORGANISM: Homo sapiens

<400> SEQUENCE: 18

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
                20                  25                  30

Glu Tyr Phe Thr Arg Leu Arg Glu Ala Arg Gln
            35                  40

<210> SEQ ID NO 19
<211> LENGTH: 44
<212> TYPE: PRT
<213> ORGANISM: Homo sapiens

<400> SEQUENCE: 19

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
                20                  25                  30

Gln His Phe Thr Arg Leu Gln Gln Glu Asn Glu Arg
            35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
            35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 21

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 25

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 29
<211> LENGTH: 44
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 32
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 33
<211> LENGTH: 44
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 33

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 34
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 35
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 36
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 37
<211> LENGTH: 44
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 37

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 38
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 39
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Ile Glu Tyr Leu Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 41

Gln Leu Glu Tyr Leu Ala Lys Gln Ile Val Asp Asn Ala Ile Gln Gln
1               5                   10                  15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Val Glu Tyr Leu Ala Lys Gln Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Asp Tyr Leu Ala Lys Gln Ile Val Asp Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Phe Leu Ala Lys Gln Ile Val Asp Asn Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Thr Leu Ala Lys Gln Ile Val Asp Asn Ala Ile Gln Gln
1               5                   10                  15

Ala

<210> SEQ ID NO 46
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 46

Gln Ile Glu Ser Leu Ala Lys Gln Ile Val Asp Asn Ala Ile Gln Gln
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Ile Ala Lys Gln Ile Val Asp Asn Ala Ile Gln Gln
1               5                   10                  15

Ala

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Val Ala Lys Gln Ile Val Asp Asn Ala Ile Gln Gln
1               5                   10                  15

Ala

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Arg Gln Ile Val Asp Asn Ala Ile Gln Gln
1               5                   10                  15

Ala

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Leu Ala Lys Asn Ile Val Asp Asn Ala Ile Gln Gln
1               5                   10                  15

Ala

<210> SEQ ID NO 51
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 51

Gln Ile Glu Tyr Leu Ala Lys Gln Ile Val Glu Asn Ala Ile Gln Gln
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr Leu Ala Lys Gln Ile Val Asp Gln Ala Ile Gln Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Leu Ala Lys Gln Ile Val Asp Asn Ala Ile Asn Gln
1               5                   10                  15

Ala

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Ile Glu Tyr Leu Ala Lys Gln Ile Val Asp Asn Ala Ile Gln Asn
1               5                   10                  15

Ala

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Ile Glu Tyr Leu Ala Lys Gln Ile Val Asp Asn Ala Ile Gln Gln
1               5                   10                  15

Leu

<210> SEQ ID NO 56
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 56

Gln Ile Glu Tyr Leu Ala Lys Gln Ile Val Asp Asn Ala Ile Gln Gln
1               5                   10                  15

Ile

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ile Glu Tyr Leu Ala Lys Gln Ile Val Asp Asn Ala Ile Gln Gln
1               5                   10                  15

Val

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ile Glu Tyr Val Ala Lys Gln Ile Val Asp Tyr Ala Ile His Gln
1               5                   10                  15

Ala

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Ile Glu Tyr Lys Ala Lys Gln Ile Val Asp His Ala Ile His Gln
1               5                   10                  15

Ala

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Ile Glu Tyr His Ala Lys Gln Ile Val Asp His Ala Ile His Gln
1               5                   10                  15

Ala

<210> SEQ ID NO 61
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ile Glu Tyr Val Ala Lys Gln Ile Val Asp His Ala Ile His Gln
1               5                   10                  15

Ala

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Leu Glu Tyr Gln Ala Gly Leu Leu Val Gln Asn Ala Ile Gln Gln
1               5                   10                  15

Ala Ile

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Leu Ile Glu Thr Ala Ser Ser Leu Val Lys Asn Ala Ile Gln Leu
1               5                   10                  15

Ser Ile

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Ile Glu Glu Ala Ala Ser Arg Ile Val Asp Ala Val Ile Glu Gln
1               5                   10                  15

Val Lys

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Leu Tyr Gln Phe Ala Asp Arg Phe Ser Glu Leu Val Ile Ser Glu
1               5                   10                  15

Ala Leu

<210> SEQ ID NO 66
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Glu Gln Val Ala Asn Gln Leu Ala Asp Gln Ile Ile Lys Glu Ala
1               5                   10                  15

Thr

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Glu Glu Leu Ala Trp Lys Ile Ala Lys Met Ile Trp Ser Asp Val
1               5                   10                  15

Phe

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Leu Val Arg Leu Ser Lys Arg Leu Val Glu Asn Ala Val Leu Lys
1               5                   10                  15

Ala Val

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Ala Glu Glu Val Ser Ala Arg Ile Val Gln Val Val Thr Ala Glu
1               5                   10                  15

Ala Val

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ile Lys Gln Ala Ala Phe Gln Leu Ile Ser Gln Val Ile Leu Glu
1               5                   10                  15

Ala Thr
```

```
<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Ala Trp Lys Ile Ala Lys Met Ile Val Ser Asp Val Met Gln Gln
1               5                   10                  15

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Glu Gln Tyr Ala Asn Gln Leu Ala Asp Gln Ile Ile Lys Glu Ala
1               5                   10                  15

Thr Glu

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Glu Glu Leu Ala Trp Lys Ile Ala Lys Met Ile Trp Ser Asp Val
1               5                   10                  15

Phe Gln Gln Cys
            20

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Ile Glu Tyr Leu Ala Lys Gln Ile Pro Asp Asn Ala Ile Gln Gln
1               5                   10                  15

Ala
```

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 85
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 85

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 86
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Glu Lys Gln Tyr Gln Glu Gln Leu Glu Glu Glu Val Ala Lys Val
1               5                   10                  15

Ile Val Ser Met Ser Ile Ala Phe Ala
            20                  25

<210> SEQ ID NO 88
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 89
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25
```

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Phe Pro Lys Pro Ser Thr Pro Pro Gly Ser Ser Gly Gly Ala Pro
1               5                   10                  15

<210> SEQ ID NO 94
<211> LENGTH: 44
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (1)..(1)
<223> OTHER INFORMATION: Ser or Thr
<220> FEATURE:

-continued

```
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
```

```
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 94

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
            35                  40

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 95

Xaa Xaa Xaa Xaa Xaa Ala Xaa Xaa Ile Val Xaa Xaa Ala Ile Xaa Xaa
1               5                   10                  15

Xaa
```

```
<210> SEQ ID NO 96
<211> LENGTH: 44
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 96

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97
```

```
Trp Thr Ser Thr Arg His Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Tyr Ser Leu Tyr Arg Ser
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Tyr Trp Met Ser
1               5

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Ile His Pro Asp Ser Ser Thr Ile Asn Tyr Ala Pro Ser Leu Lys
1               5                   10                  15

Asp

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Tyr Phe Gly Phe Pro Trp Phe Ala Tyr
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ser Ser Gln Ser Ile Val His Ser Asn Gly Asn Thr Tyr Leu Glu
1               5                   10                  15

<210> SEQ ID NO 103
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Lys Val Ser Asn Arg Phe Ser
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Phe Gln Gly Ser His Val Pro Pro Thr
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Tyr Gly Met Asn
1               5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Ile Asn Thr Tyr Thr Gly Glu Pro Thr Tyr Ala Asp Asp Phe Lys
1               5                   10                  15
Gly

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Gly Trp Met Asp Phe Asn Ser Ser Leu Asp Tyr
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108
```

Ser Ala Ser Ser Arg Val Ser Tyr Ile His
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Thr Ser Thr Leu Ala Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Trp Ser Tyr Asn Pro Pro Thr
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Tyr Tyr Met Ser
1               5

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Ile Ala Asn Lys Ala Asn Gly His Thr Thr Asp Tyr Ser Pro Ser
1               5                   10                  15

Val Lys Gly

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Met Gly Ile Arg Trp Asn Phe Asp Val
1               5                   10

<210> SEQ ID NO 114
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Lys Ala Ser Gln Asp Val Gly Thr Ser Val Ala
1               5                   10
```